US007557122B2

(12) United States Patent
Boubia et al.

(10) Patent No.: US 7,557,122 B2
(45) Date of Patent: Jul. 7, 2009

(54) PYRROLOPYRIDINE COMPOUNDS, METHOD OF MAKING THEM AND USES THEREOF

(75) Inventors: Benaïssa Boubia, Saint Apollinaire (FR); Martine Barth, Asnieres les Dijon (FR); Jean Binet, Fontaine les Dijon (FR); Pierre Dodey, Fontaine les Dijon (FR); Christiane Legendre, Velard sur Ouche (FR); Olivia Poupardin-Olivier, Varois et Chaignot (FR)

(73) Assignee: Laboratoires Fournier S.A., Dijon Cedex (FR)

( * ) Notice: Subject to any disclaimer, the term of this patent is extended or adjusted under 35 U.S.C. 154(b) by 0 days.

(21) Appl. No.: 12/040,336

(22) Filed: Feb. 29, 2008

(65) Prior Publication Data

US 2008/0200495 A1 Aug. 21, 2008

Related U.S. Application Data

(63) Continuation of application No. PCT/FR2006/050827, filed on Aug. 31, 2006.

(60) Provisional application No. 60/713,459, filed on Sep. 1, 2005.

(30) Foreign Application Priority Data

Oct. 14, 2005 (FR) ................................. 05 10482

(51) Int. Cl.
*C07D 471/04* (2006.01)
*A61K 31/4745* (2006.01)
(52) U.S. Cl. ........................ 514/300; 544/105; 546/113; 514/230.5
(58) Field of Classification Search ................. 546/113; 514/300, 230.5; 544/105
See application file for complete search history.

(56) References Cited

U.S. PATENT DOCUMENTS

| 2006/0100230 | A1 | 5/2006 | Bischoff et al. |
| 2007/0117860 | A1 | 5/2007 | Dittrich-Wengenroth et al. |
| 2007/0149514 | A1 | 6/2007 | Woltering et al. |
| 2007/0185183 | A1 | 8/2007 | Siegel et al. |

FOREIGN PATENT DOCUMENTS

| WO | WO 97/28149 A1 | 8/1997 |
| WO | WO 98/25611 A1 | 6/1998 |
| WO | WO 01/60807 A1 | 8/2001 |
| WO | WO 02/071827 A2 | 9/2002 |
| WO | WO 03/044018 A1 | 5/2003 |
| WO | WO 2004/005253 A1 | 1/2004 |
| WO | WO 2004/060871 A1 | 7/2004 |
| WO | WO 2005/009958 A1 | 2/2005 |
| WO | WO 2005/016335 A1 | 2/2005 |
| WO | WO 2005/016881 A1 | 2/2005 |
| WO | WO 2005/056522 A2 | 6/2005 |

OTHER PUBLICATIONS

International Search Report dated Jan. 18, 2007 (three (3) pages).
*Recent Patents Cardiovasc Drug Discov.* Jun. 2006;1(2):193-209, Role of PPAR in cardiovascular diseases. Das SK, Chakrabarti R, Metabolic Disorders Group, Dr. Reddy's Lab, Discovery Research, Bollaram Road, Miyapur, Hyderabad 500049, India. saibal99@yahoo.com.
*Biochem Soc Trans.* Dec. 2006;34(Pt 6):1341-6. PPAR: a new pharmacological target for neuroprotection in stroke and neurodegenerative diseases. Bordet R, Ouk T, Petrault O, Gelé P, Gautier S, Laprais M, Deplanque D, Duriez P, Staels B, Fruchart JC, Bastide M. EA1046 Department of Medical Pharmacology, Faculty of Medicine, Institute of Predictive Medicine and Therapeutic Research, University Lille 2 and Lille University Hospital, 1 place de Verdun, 59045 Lille Cedex, France. email bordet{fourth root}univ-lille2.fr.
*Neurotherapeutics.* Jul 2008;5(3):481-9. PPARgamma agonists as therapeutics for the treatment of Alzheimer's disease. Landreth G, Jiang Q, Mandrekar S, Heneka M. Alzheimer Research Laboratory, Department of Neurosciences, Case Western Reserve University School of Medicine, Cleveland, Ohio 44106, USA. gel2@case.edu.
*Prog Neurobiol.* Aug. 2008;85(4):433-51. Epub May 4, 2008. RAR/RXR and PPAR/RXR signaling in neurological and psychiatric diseases. Van Neerven S, Kampmann E, Mey J. Institute of Biology II, RWTH Aachen, Aachen, Germany.
*J Neurochem.* Jul. 2008;106(2):506-18. Epub Apr. 1, 2008 PPAR: a therapeutic target in Parkinson's disease. Chaturvedi RK, Beal MF. Department of Neurology and Neuroscience. Weill Medical College of Cornell University, New York, New York, USA.
*CNS Drugs.* 2008;22(1):1-14. The role of peroxisome proliferator-activated receptor-gamma (PPARgamma) in Alzheimer's disease: therapeutic implications. Jiang Q, Heneka M, Landreth. GE Department of Neurosciences, Alzheimer Research Laboratory, School of Medicine, Case Western Reserve University, Cleveland, Ohio 44106, USA.
*J Neurochem.* Oct. 2008;107(2):497-509. Epub Aug. 14, 2008. PPARalpha and PPARgamma effectively protect against HIV-induced inflammatory responses in brain endothelial cells. Huang W, Rha GB, Han MJ, Eum SY, András IE, Zhong Y, Hennig B, Toborek M. Molecular Neuroscience and Vascular Biology Laboratory, Department of Neurosurgery, University of Kentucky, Lexington, Kentucky, USA.

*Primary Examiner*—Kahsay T Habte
(74) *Attorney, Agent, or Firm*—Crowell & Moring LLP

(57) ABSTRACT

Pyrrolopyridine compounds corresponding to formula (I):

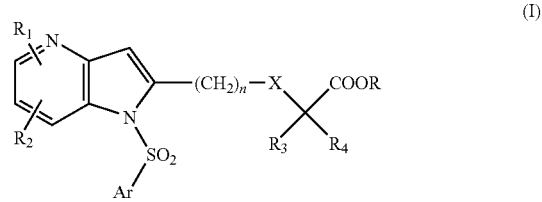

as defined in the claims, pharmaceutically acceptable salts thereof, the process for preparing such compounds, pharmaceutical compositions containing such compounds, and their use as pharmacologically active substances, especially in the treatment of hypertriglyceridemia, hyperlipidemia, hypercholesterolemia, diabetes, endothelial dysfunction, cardiovascular diseases, inflammatory diseases and neurodegenerative diseases.

10 Claims, No Drawings

PYRROLOPYRIDINE COMPOUNDS, METHOD OF MAKING THEM AND USES THEREOF

CROSS REFERENCE TO RELATED APPLICATIONS

This application is a continuation of international patent application No. PCT/FR2006/050827, filed Aug. 31, 2006, designating the United States of America and published in French on Mar. 8, 2007, as WO/2007/026104, the entire disclosure of which is incorporated herein by reference. Priority is claimed based on U.S. provisional patent application No. 60/713,459, filed Sep. 1, 2005 and French patent application no. FR 0510482, filed Oct. 14, 2005.

SPECIFICATION

The present invention relates to novel pyrrolopyridine compounds, to a process for manufacturing them and to their therapeutic use for preventing or treating pathologies involving nuclear receptors of PPAR type.

PRIOR ART

In therapeutics, it is known that cardiovascular system diseases are an important risk factor for health. These diseases are often the consequence of a high level of cholesterol and/or of triglycerides, and it is thus important to keep these levels below values commonly accepted by the medical profession.

In the case of cholesterol, it is in particular necessary to evaluate the amounts of cholesterol associated with various lipoproteins in order to adapt the treatments so as to lower the levels of LDL-cholesterol while at the same time maintaining the levels of HDL-cholesterol. Among the known families of compounds used for regulating these parameters are the statins, which are HMG CoA reductase inhibitors that make it possible essentially to treat excessively high levels of LDL-cholesterol, and compounds of the fibrate family, which act by activating the PPARα (peroxisome proliferator-activated receptor alpha) nuclear receptors and allow the levels of triglycerides and cholesterol to be lowered.

Study of the PPAR nuclear receptors has led to the identification of three subtypes, known as PPARα, PPARγ and PPARδ. These various receptors, by binding to certain specific fragments of DNA, regulate the expression of target genes involved in lipid metabolism regulation mechanisms (see, for example, Current Topics in Medicinal Chemistry, 2003, 3, (14), 1649-1661).
Thus:
PPARα: is expressed essentially in the liver and is involved in fatty acid catabolism by regulating β- and ω-oxidation (J. Lipid. Res. (1996) 37, 907-925);
the PPARγs are expressed mainly in adipose tissue and are involved in glycemia regulation mechanisms;
PPARδ is expressed ubiquitously, but is mainly present in the kidneys, skeletal muscle, the heart and the intestine. Like the other receptors of PPAR type, PPARδ forms a heterodimer with RXR (retinoid X receptor) and is then capable of binding to certain target gene elements of the nucleus and of controlling transcription factors. Among the various studies devoted to this nuclear receptor, it has been demonstrated, for example, that activation of PPARδ makes it possible to increase the level of HDL-cholesterol in db/db mice (FEBS Letters (2000), 473, 333-336) and obese insulin-dependent Rhesus monkeys, and promotes the flow of cholesterol via ApoA1 in human THP-1 cells, (Proc. Nat. Ac. Sci. USA (2001), 98, 5306-5311).

The treatment of type 2 non-insulin-dependent diabetes remains unsatisfactory, despite the arrival on the market of numerous oral hypoglycemiant derivatives for facilitating the secretion of insulin and for promoting its action on the target peripheral tissues. PPARγ agonists are generally described for improving sensitivity to insulin, as has already been observed with the thiazolidinediones (TZD).

Novel PPAR agonists are developed in the treatment of type 2 diabetes and/or dyslipidemia. Among the novel PPAR agonists, several are activators of at least two of the three subtypes PPAR α, δ and γ.

The increase in the frequency of these pathologies calls for the development of novel therapeutic agents that are active in the case of these diseases: compounds having excellent hypoglycemiant and hypolipidemiant activity while avoiding the side effects observed with thiazolidinediones are consequently very useful in the treatment and/or prophylaxis of type 2 non-insulin-dependent diabetes for reducing peripheral insulin resistance and normalizing glycemia.

Following the study of these various nuclear receptors, it appears that compounds that are agonists simultaneously of two, and preferably of three, PPAR receptor subtypes, might have an extremely advantageous pharmacological profile for simultaneously treating pathologies such as hyperlipidemia, hypercholesterolemia and diabetes, and also various cardiovascular system diseases that are the consequence of a metabolic syndrome.

The present invention concerns PPAR receptor activators or modulators. These compounds satisfy the pharmacological criteria mentioned above.

Among the prior art documents mentioning similar compounds, known examples include documents WO 97/28149, WO 04/060871, WO 05/016335 and WO 05/016881, which describe PPARδ receptor agonists, document WO 01/60807, which describes PPARα agonists, or documents WO 05/009958 and WO 05/056522, which propose indole compounds that are active on the PPAR receptors.

Mention will also be made of documents WO 02/071827 and Bioorganic and Med. Chem. Letter Vol. 14 (11) pp. 259-2763 (06/2004), which describe derivatives that are RXR receptor modulators and their therapeutic use for treating pathologies involved in metabolic syndrome.

Moreover, various pyrrolopyridine compounds have been described in the prior art, for instance certain intermediates disclosed in document WO 98/25611, the claimed compounds of which are active against thrombosis.

SUMMARY OF THE INVENTION

The present invention relates to novel pyrrolopyridine derivatives that are PPAR activators, and are chosen from i) the compounds of formula:

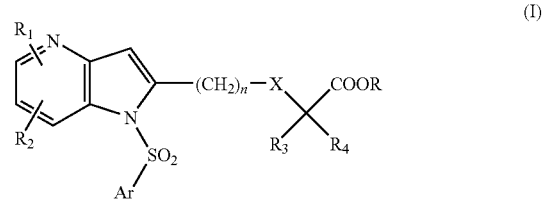

in which:

$R_1$ and $R_2$ each independently represent a hydrogen atom, a halogen atom, a $C_1$-$C_4$ alkyl or $C_1$-$C_4$ alkoxy group or a $CF_3$ group, $R_3$ and $R_4$ each independently represent a hydrogen atom or a $C_1$-$C_4$ alkyl group, R represents a hydrogen atom or a $C_1$-$C_3$ alkyl group, n=1, 2 or 3

X represents a single bond or an oxygen atom,

Ar represents an aromatic or heteroaromatic nucleus chosen from phenyl, pyrazolyl, imidazolyl, thiazolyl, oxazolyl, isoxazolyl, furyl, thienyl, pyrrolyl, pyridyl, biphenyl, naphthyl, 1,2,3,4-tetrahydronaphthyl, isoquinolyl, quinolyl, 1,2,3,4-tetrahydroquinolyl, benzimidazolyl, benzopyrazinyl, indolyl, 2,3-dihydroindolyl, benzofuryl, 2,3-dihydrobenzofuryl, benzothiazolyl, benzothiadiazolyl, benzisoxazolyl, 3,4-dihydro-1,4-benzoxazinyl, 1,3-benzodioxolyl, 2,3-dihydrobenzodioxinyl, imidazothiazolyl and benzoxazolyl groups, optionally substituted with one or more (for example 2 or 3) substituents chosen from halogen atoms and $C_1$-$C_6$ alkyl, $C_1$-$C_4$ alkoxy, trifluoromethyl, trifluoromethoxy, nitro, acetyl, acetylamino and dialkylamino groups, in which each alkyl group contains from 1 to 3 carbon atoms or amino, or oxazolyl, thiazolyl, pyrazolyl, pyrrolidinyl, pyridyl, pyrimidinyl, methylpyrimidinyl or morpholinyl heterocycles, ii) pharmaceutically acceptable salts thereof.

According to a second aspect, the invention relates to the abovementioned compounds for their use as pharmacologically active substances, and also to the pharmaceutical compositions containing from.

In addition, the invention relates to the use of at least one compound of formula (I) or a pharmaceutically acceptable salts thereof as an active principle for the preparation of a medicament intended for a therapeutic use, especially for combating hypercholesterolemia, hyperlipidemia, hypertriglyceridemia, dyslipidemia, insulin resistance, diabetes or obesity, and also cardiovascular diseases that are the consequence of an imbalance of serum lipoproteins. The compounds according to the invention are also useful as active principles for medicaments for preventing or treating diseases associated with endothelial dysfunction, atherosclerosis, myocardial infarction, hypertension, cerebral vascular problems, certain inflammatory diseases, for instance rheumatoid arthritis, and neurodegenerative diseases especially such as Alzheimer's disease or Parkinson's disease.

DETAILED DESCRIPTION

In the present description, the term "$C_1$-$C_n$ alkyl group" (n being an integer) means a linear, branched or partially or totally cyclic hydrocarbon-based chain containing from 1 to n carbon atoms, the cyclic part containing at least 3 carbon atoms. For example, and without limitation, a $C_1$-$C_6$ alkyl group may be a methyl, ethyl, propyl, butyl, pentyl, hexyl, 1-methylethyl, 1-methylpropyl, 2-methylpropyl, 1,1-methylethyl, 1-methylbutyl, 1,1-dimethylpropyl, 1-methylpentyl, 1,1-dimethylbutyl, cyclopropyl, cyclobutyl, cyclopentyl, cyclohexyl or cyclopentylmethyl group. The term "$C_1$-$C_n$ alkoxy group" (n being an integer) means a group RO- in which R represents an alkyl group containing from 1 to n carbon atoms as defined previously. The term "halogen" means a fluorine, chlorine, bromine or iodine atom, fluorine and chlorine atoms being preferred.

The compounds of formula (I) in which R represents a hydrogen atom are carboxylic acids that may be used in the form of free acids or in the form of salts, said salts being obtained by combining the acid with a pharmaceutically acceptable nontoxic mineral or organic base. Among the mineral bases that may be used are, for example, sodium hydroxide, potassium hydroxide, magnesium hydroxide and calcium hydroxide. Among the organic bases that may be used are, for example, amines, amino alcohols, basic amino acids such as lysine or arginine, or compounds bearing a quaternary ammonium function, for instance betaine or choline.

The compounds of formula (I) in which the substituents $R_3$ and $R_4$ are different have an asymmetric center. For these compounds, the invention covers both the racemic compound and each of the optical isomers considered separately.

One particular family of compounds according to the invention comprises the compounds of the abovementioned formula I in which:

$R_1$ and $R_2$ each independently represent a hydrogen atom, a halogen atom or a $CF_3$ group, $R_3$ and $R_4$ each independently represent a hydrogen atom or a $C_1$-$C_4$ alkyl group, R represents a hydrogen atom or a $C_1$-$C_3$ alkyl group, n=1 or 2, X represents a single bond or an oxygen atom, Ar represents an aromatic or heteroaromatic nucleus chosen from phenyl, naphthyl, benzothiazolyl, 3,4-dihydro-1,4-benzoxazinyl, 1,3-benzodioxolyl, 2,3-dihydrobenzodioxinyl and benzoxazolyl groups, optionally substituted with one or more substituents chosen from $C_1$-$C_6$ alkyl, $C_1$-$C_4$ alkoxy and amino groups.

Among the compounds of formula I according to the invention, the preferred compounds are those
in which:

$R_1$ and $R_2$ each independently represent a hydrogen atom, a halogen atom, a $C_1$-$C_4$ alkyl or $C_1$-$C_4$ alkoxy group or a $CF_3$ group, $R_3$ and $R_4$ each independently represent a hydrogen atom or a $C_1$-$C_4$ alkyl group, R represents a hydrogen atom or a $C_1$-$C_3$ alkyl group, n=1, 2 or 3

X represents a single bond or an oxygen atom,

Ar represents an aromatic or heteroaromatic nucleus chosen from phenyl, pyridyl, biphenyl, naphthyl, quinolyl, benzopyrazinyl, indolyl, 2,3-dihydroindolyl, benzofuryl, 2,3-dihydrobenzofuryl, benzothiazolyl, benzothiadiazolyl, benzisoxazolyl, 3,4-dihydro-1,4-benzoxazinyl, 1,3-benzodioxolyl, 2,3-dihydrobenzodioxinyl, imidazothiazolyl and benzoxazolyl groups, optionally substituted with one or more (for example 2 or 3) substituents chosen from halogen atoms and $C_1$-$C_6$ alkyl, $C_1$-$C_4$ alkoxy, trifluoromethyl, trifluoromethoxy, nitro, acetyl, acetylamino and dialkylamino groups, in which each alkyl group contains from 1 to 3 carbon atoms or amino, or oxazolyl, thiazolyl, pyrazolyl, pyrrolidinyl, pyridyl, pyrimidinyl, methylpyrimidinyl or morpholinyl heterocycles.

Among the compounds according to the invention, preferred compounds are also those in which Ar represents a phenyl group. The compounds in which $R_1$ represents a chlorine atom or a trifluoromethyl group are also preferred.

The compounds according to the invention may be prepared according to a first process that consists in:

a) performing a halogenation reaction, preferentially an iodination reaction, of an aminopyridine of formula

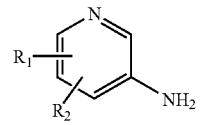

(II)

in which:

$R_1$ and $R_2$ each independently represent a hydrogen atom, a chlorine, bromine or fluorine atom, a $C_1$-$C_4$ alkyl or $C_1$-$C_4$ alkoxy group or a trifluoromethyl group, using a halogenating agent, for instance iodine in the presence of silver sulfate or benzyltrimethylammonium dichloroiodate, in a solvent, such as dichloromethane or an aliphatic alcohol, at room temperature, for 5 to 24 hours to obtain the compound of formula

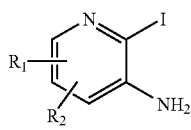
(III)

in which:

$R_1$ and $R_2$ conserve the same meaning as in the starting compounds;

b) reacting, according to the Sonogashira reaction (see, for example: Tet. Lett., 1975, 4467), the compound of formula III with an acetylenic derivative of formula

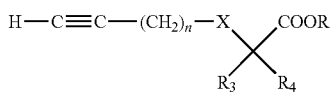
(IV)

in which:

n=1, 2 or 3;

$R_3$ and $R_4$ each independently represent a hydrogen atom or a $C_1$-$C_4$ alkyl group;

R represents a $C_1$-$C_3$ alkyl group;

X represents a single bond or an oxygen atom;

in the presence of cuprous iodide, a palladium-based catalyst, for instance tetrakis(triphenylphosphine)palladium or dichloro-bis(triphenylphosphine)palladium, and an organic base, for instance triethylamine, in a solvent, for instance dimethylformamide (DMF), at a temperature of between 0 and 60° C. for 2 to 24 hours, to obtain the compound of formula

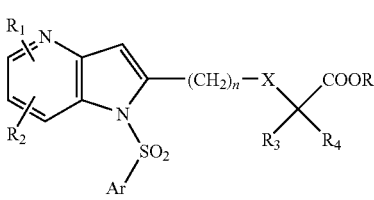
(V)

in which:

$R_1$, $R_2$, n, X, $R_3$, $R_4$ and R conserve the same meaning as in the starting compounds;

c) reacting the compound of formula V with an arylsulfonyl chloride of formula

Ar—SO$_2$—Cl (VI)

in which:

Ar represents an aromatic or heteroaromatic nucleus chosen from phenyl, pyrazolyl, imidazolyl, thiazolyl, oxazolyl, isoxazolyl, furyl, thienyl, pyrrolyl, pyridyl, biphenyl, naphthyl, 1,2,3,4-tetrahydronaphthyl, quinolyl, isoquinolyl, 1,2,3,4-tetrahydroquinolyl, benzimidazolyl, benzopyrazinyl, indolyl, 2,3-dihydroindolyl, benzofuryl, 2,3-dihydrobenzofuryl, benzothiazolyl, benzothiadiazolyl, benzisoxazolyl, 3,4-dihydro-1,4-benzoxazinyl, 1,3-benzodioxolyl, 2,3-dihydrobenzodioxinyl, imidazothiazolyl and benzoxazolyl groups, optionally substituted with one or more (for example 2 or 3) substituents chosen from halogen atoms and $C_1$-$C_6$ alkyl, $C_1$-$C_4$ alkoxy, trifluoromethyl, trifluoromethoxy, nitro, acetyl, acetylamino and dialkylamino or amino groups, or oxazolyl, thiazolyl, pyrazolyl, pyrrolidinyl, pyridyl, pyrimidinyl, methylpyrimidinyl or morpholinyl heterocycles, in the presence of pyridine, optionally in a solvent, such as dichloromethane, at room temperature, for 10 to 120 minutes, to obtain the compound of formula

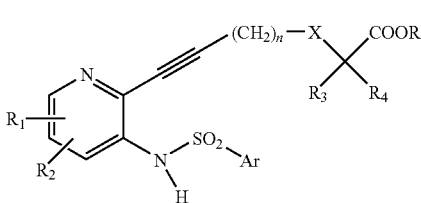
(VII)

in which:

$R_1$, $R_2$, n, X, $R_3$, $R_4$, R and Ar conserve the same meaning as in the starting compounds;

d) performing a cyclization of the compound of formula VII, for example via the action of copper II acetate (see, for example J. Org. Chem., 2004, 69 (4), 1126-1136), in a solvent, such as 1,2-dichloroethane, at a temperature close to the reflux temperature of the solvent, for 4 to 24 hours, to obtain the compound of formula

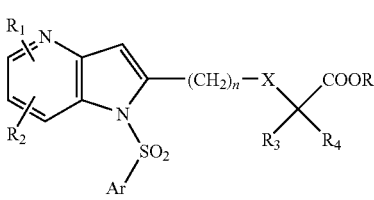
(Ia)

in which:

$R_1$, $R_2$, n, X, $R_3$, $R_4$, R and Ar conserve the same meaning as in the starting compounds;

e) if necessary, hydrolyzing the ester function of the compound of formula Ia, for example via the action of a mineral base, such as sodium hydroxide or lithium hydroxide, according to procedures that are well known to those skilled in the art, to obtain, after acid treatment, the compound of formula I in the form of the free acid:

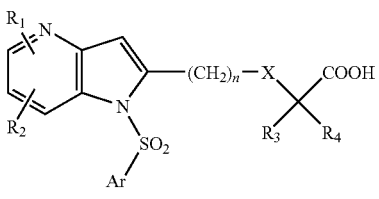
(Ib)

According to the first variant of the preparation process, the compounds of formula I may be obtained via a series of reactions consisting in:

a) reacting the compound of formula (III)

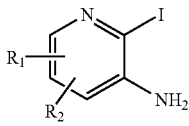
(III)

as obtained above, with an arylsulfonyl chloride of formula

Ar—SO$_2$—Cl    (VI)

in which:

Ar represents an aromatic or heteroaromatic nucleus chosen from phenyl, pyrazolyl, imidazolyl, thiazolyl, oxazolyl, isoxazolyl, furyl, thienyl, pyrrolyl, pyridyl, biphenyl, naphthyl, 1,2,3,4-tetrahydronaphthyl, quinolyl, isoquinolyl, 1,2,3,4-tetrahydroquinolyl, benzimidazolyl, benzopyrazinyl, indolyl, 2,3-dihydroindolyl, benzofuryl, 2,3-dihydrobenzofuryl, benzothiazolyl, benzothiadiazolyl, benzisoxazolyl, 3,4-dihydro-1,4-benzoxazinyl, 1,3-benzodioxolyl, 2,3-dihydrobenzodioxinyl, imidazothiazolyl and benzoxazolyl groups, optionally substituted with one or more (for example 2 or 3) substituents chosen from halogen atoms and $C_1$-$C_6$ alkyl, $C_1$-$C_4$ alkoxy, trifluoromethyl, trifluoromethoxy, nitro, acetyl, acetylamino and dialkylamino or amino groups, or oxazolyl, thiazolyl, pyrazolyl, pyrrolidinyl, pyridyl, pyrimidinyl, methylpyrimidinyl or morpholinyl heterocycles, in a solvent, for instance dimethylformamide, preferably in the presence of an aprotic base, for instance pyridine, at room temperature and for 1 to 12 hours, to obtain the compound of formula (VIII)

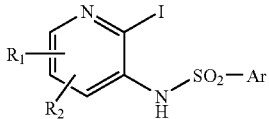
(VIII)

in which:

$R_1$, $R_2$ and Ar conserve the same meaning as in the starting compounds;

b) reacting the compound of formula VIII with an acetylenic derivative of formula

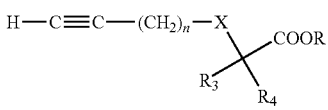
(III)

in which:

n=1, 2 or 3;

$R_3$ and $R_4$ each independently represent a hydrogen atom or a $C_1$-$C_4$ alkyl group;

R represents a $C_1$-$C_3$ alkyl group;

X represents a single bond or an oxygen atom;

under conditions similar to those described for step b) of the above general process, to obtain the compound of formula

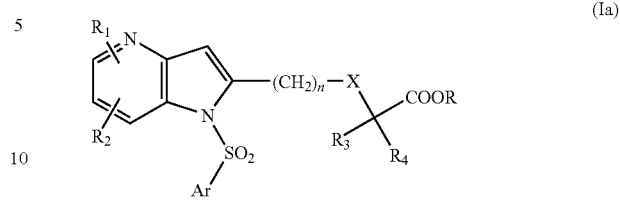
(Ia)

in which $R_1$, $R_2$, n, X, $R_3$, $R_4$, R and Ar conserve the same meaning as in the starting compounds;

c) if necessary, hydrolyzing the ester function of the compound of formula Ia, for example via the action of a mineral base, such as sodium hydroxide or lithium hydroxide, according to procedures that are well known to those skilled in the art, to obtain, after acid treatment, the compound of formula I in the form of the free acid:

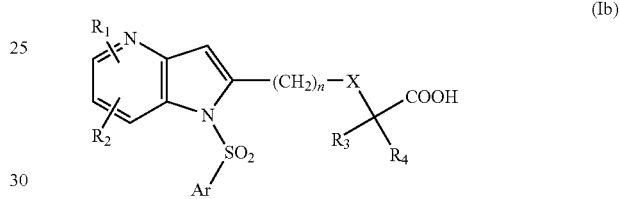
(Ib)

The compounds of the invention in the form of salts of an acid of formula Ib with a mineral or organic base may be obtained conventionally, by using methods that are well known to those skilled in the art, for example by mixing stoichiometric amounts of the acid and the base in a solvent, for instance water or an aqueous-alcoholic mixture, and then freeze-drying the solution obtained.

In some of the reaction steps described above, it is advantageously possible to replace the traditional heating methods with microwave heating using reactors adapted to this mode of reaction. In this case, a person skilled in the art will understand that the "heating" times will be considerably reduced in comparison with the times required for standard heating.

The examples that follow the preparation of compounds according to formula (I) will allow the invention to be understood more clearly.

In these examples, which do not limited the scope of the invention, the term "preparation" denotes examples describing the synthesis of intermediate compounds and the term "examples" are examples describing the synthesis of compounds of formula (I) according to the invention. Among the abbreviations, "mM" means millimoles, THF means tetrahydrofuran, DMF means dimethylformamide, DME means 1,2-dimethoxyethane, DCM means dichloromethane and PdCl$_2$dppf means dichloro-1,1'-bis(diphenylphosphino)-ferrocenepalladium(II).

The melting points are measured on a Köfler block or using a Mettler machine and the nuclear magnetic resonance spectral values are characterized by the chemical shift calculated relative to TMS, by the number of protons associated with the signal and by the shape of the signal (s for singlet, d for doublet, dd for doubled doublet, t for triplet, q for quartet, quint. for quintet and m for multiplet). The working frequency and the solvent used are indicated for each compound. Room temperature is 20° C.±5° C.

PREPARATION I

3-Amino-6-chloro-2-iodopyridine 23.2 g (180.5 mM) of 5-amino-2-chloropyridine are mixed in 70 ml of dichloro-methane (DCM) and 180 ml of methanol, and 21.6 g (216 mM) of calcium carbonate and 75.3 g (226 mM) of benzyltrimethylammonium dichloroiodate are added. The reaction mixture is stirred at room temperature for 16 hours, and then filtered to remove the mineral salts. The filtrate is diluted with water and extracted with DCM. The organic phase obtained is washed with sodium chloride solution, and then with saturated sodium thiosulfate solution, dried over magnesium sulfate and concentrated under reduced pressure. An oil is obtained, which is purified by chromatography on silica gel, eluting with a cyclohexane/ethyl acetate mixture (80/20 and then 70/30; v/v). 13.9 g of the expected product are thus obtained in the form of an orange-colored solid (yield=30%).

m.p.=148° C.

PREPARATION II

3-[Di(benzenesulfonyl)amino]-6-chloro-2-iodopyridine

A mixture of 13.75 g (54 mM) of the compound according to Preparation I and 27.6 ml (216 mM) of benzenesulfonyl chloride in 30 ml of pyridine is stirred for 60 hours at room temperature. The reaction mixture is then diluted with water and extracted several times with ethyl acetate. The organic phase is washed with N hydrochloric acid solution, and then with sodium chloride solution, dried over magnesium sulfate and concentrated under reduced pressure. The expected compound is obtained in the form of a beige-colored solid (yield=96%).

m.p.=231° C.

PREPARATION III

N-(6-Chloro-2-iodo-3-pyridyl)benzenesulfonamide 15.46 g (29 mM) of the compound according to Preparation II are mixed in 170 ml of dioxane and 77 ml of aqueous 3 M potassium hydroxide solution are added. The reaction mixture is stirred under gentle reflux of the solvent for 1 hour, and then concentrated under reduced pressure. A beige-colored solid is obtained, which is suspended in 200 ml of water. The mixture is acidified to pH 4 approximately by adding hydrochloric acid and is then extracted with dichloromethane (DCM). The organic phase is dried over magnesium sulfate and then concentrated under reduced pressure. 10.32 g of the expected product are thus obtained in the form of a beige-colored solid (yield=91%).

m.p.=132° C.

EXAMPLE 1

5-Chloro-1-(phenylsulfonyl)-1H-pyrrolo[3,2-b]pyridine-2-propanoic acid, methyl ester 10.32 g (26.2 mM) of the compound according to Preparation III, 30 ml of dimethylformamide, 460 mg (0.65 mM) of dichlorobis(triphenylphosphine)palladium, 250 mg (1.3 mM) of cuprous iodide and 20 ml of diethylamine are mixed together. 3.5 g (31.25 mM) of methyl 4-pentynoate are then added with stirring, at room temperature, and the reaction mixture is stirred for 1 hour under gentle reflux of the solvent. The reaction mixture is then diluted with water and extracted several times with ethyl acetate. The organic phase is washed with sodium chloride solution, dried over magnesium sulfate and concentrated under reduced pressure. The brown oil obtained is purified by chromatography on silica gel, eluting with a cyclohexane/ethyl acetate mixture (8/2; v/v). 8.02 g of the expected product are thus obtained in the form of a yellow solid (yield: 81%).

m.p.=108-115° C.

EXAMPLE 2

5-Chloro-1-(phenylsulfonyl)-1H-pyrrolo[3,2-b]pyridine-2-propanoic acid 1.5 g (4 mM) of the ester obtained according to Example 1 are mixed in 5 ml of tetrahydrofuran and a solution of 332 mg (7.9 mM) of lithium hydroxide (LiOH.H$_2$O) in 4 ml of water is added. The reaction medium is stirred for 2 hours at room temperature and then acidified to pH 3 with hydrochloric acid and extracted with DCM. The organic phase is dried over magnesium sulfate and concentrated under reduced pressure. A slightly yellow oil is obtained, which crystallizes in the form of a white solid (yield=77%).

m.p.=185-187° C.

PREPARATION IV

3-Amino-2-iodo-6-(trifluoromethyl)pyridine 3.85 g (12.3 mM) of silver sulfate are added, with stirring and at room temperature, to a solution of 2 g (12.3 mM) of 5-amino-2-(trifluoromethyl)pyridine in 100 ml of ethanol. 3.13 g of iodine are then added and the reaction mixture is stirred at room temperature for 24 hours. The solid in suspension in the medium is removed by filtration and the filtrate is concentrated under reduced pressure. The evaporation residue is taken up in 200 ml of dichloromethane and washed with 5% sodium hydroxide solution, and then with water and dried over magnesium sulfate. The solution obtained is concentrated under reduced pressure and 3.42 g of the expected compound are thus obtained in the form of a pink solid (yield=96%).

m.p.=127° C.

PREPARATION V

6-(3-Amino-6-chloro-2-pyridyl)-5-hexynoic acid, methyl ester 5 g (19.6 mM) of the compound according to Preparation I, 20 ml of dimethylformamide, 345 mg (0.49 mM) of dichlorobis(triphenylphosphine)palladium, 187 mg (0.98 mM) of cuprous iodide and 10 ml of diethylamine are mixed together. 2.97 g (23.5 mM) of methyl 5-hexynoate are then added with stirring, at room temperature, and the reaction mixture is stirred for 1 hour under gentle reflux of the solvent. The reaction mixture is then diluted with water and extracted several times with ethyl acetate. The organic phase is washed with sodium chloride solution, dried over magnesium sulfate and concentrated under reduced pressure. The residual oily compound obtained is purified by chromatography on silica gel, eluting with a cyclohexane/ethyl acetate mixture (9/1; v/v). 4.15 g of the expected product are thus obtained in the form of an oil (yield: 84%).

¹H NMR (300 MHz, DMSO) δ: 1.83 (quint., 2H); 2.47 (t, 2H); 2.54 (t, 2H); 3.60 (s, 3H); 5.63 (s, 2H); 7,10 (s, 2H).

PREPARATION VI

6-[3-[(6-Benzothiazolylsulfonyl)amino]-6-chloro-2-pyridyl]-5-hexynoic acid, methyl ester A solution of 1 g (4 mM) of the compound according to Preparation V in 10 ml of pyridine is prepared and 1.1 g (4.7 mM) of 6-benzothiazolesulfonyl chloride are added. The mixture is stirred for 3 hours at room temperature and then diluted with water and extracted with ethyl acetate. The organic phase is washed twice with N hydrochloric acid solution, and then with water, dried over magnesium sulfate and concentrated under reduced pressure. The residual oil is purified by chromatography on silica gel, eluting with a cyclohexane/ethyl acetate mixture (7/3; v/v). 1.07 g of the expected compound are thus obtained in the form of a yellow solid (yield=60%).

m.p.=134° C.

EXAMPLE 3

1-(6-Benzothiazolylsulfonyl)-5-chloro-1H-pyrrolo[3,2-b]pyridine-2-butanoic acid, methyl ester A mixture of 1 g (2.22 mM) of ester according to Preparation VI in 3 ml of 1,2-dichloroethane is prepared in a microwave reactor tube, and 403 mg (2.22 mM) of copper (cupric) acetate are added. The mixture is heated by microwave at 150° C. for 30 minutes, and then cooled, diluted with 6 ml of dichloromethane and filtered through Whatman paper. The filtrate is concentrated under reduced pressure and the crude product is purified by chromatography on silica gel, eluting with a cyclohexane/ethyl acetate mixture (8/2; v/v). 500 mg of the expected compound are thus obtained in the form of a yellow solid (yield=50%).

m.p.=55° C.

EXAMPLE 4

1-(6-Benzothiazolylsulfonyl)-5-chloro-1H-pyrrolo[3,2-b]pyridine-2-butanoic acid

By working in a manner similar to that of Example 2, starting with the compound obtained according to Example 3, the expected product is obtained in the form of a beige-colored solid (yield=95%).

m.p.=178° C.

PREPARATION VII

N-[2-Iodo-6-(trifluoromethyl)-3-pyridyl]benzenesulfonamide 7 g (40 mM) of benzenesulfonyl chloride are gradually added, with stirring and at room temperature, to a solution of 2.88 g (10 mM) of the compound according to Preparation IV in 25 ml of pyridine. The reaction mixture is stirred at room temperature for 24 hours, and then poured into 300 ml of ice-cold N hydrochloric acid. The precipitate obtained is separated out by filtration and washed with water on the filter, and then stirred in a flask with 40 ml of dioxane and 10 ml of aqueous 3 M potassium hydroxide solution, under gentle reflux of the solvent, for 2 hours. This reaction mixture is cooled, diluted with 300 ml of water, acidified to pH 1.5 approximately with concentrated hydrochloric acid, and is then extracted with dichloromethane. The organic phase obtained is washed with water and then dried over magnesium sulfate and concentrated under reduced pressure. 3.7 g of the expected product are thus obtained in the form of a white solid (yield=89%).

m.p.=131° C.

PREPARATION VIII

5-[3-Amino-6-chloro-2-pyridyl]-4-pentynoic acid, methyl ester

By working in a manner similar to that of Preparation V, starting with the methyl ester of 4-pentynoic acid, the expected product is obtained in the form of a yellow solid (yield=77%).

m.p.=96-100° C.

By working in a manner similar to that of Preparation VI, starting with the appropriate sulfonyl chlorides, the following compounds are obtained:

PREPARATION IX

6-[3-[(1,3-Benzodioxol-5-ylsulfonyl)amino]-6-chloro-2-pyridyl]-5-hexynoic acid, methyl ester Brown solid, yield=91%.

m.p.=123° C.

PREPARATION X

6-[3-[(2-Amino-5-benzothiazolylsulfonyl)amino]-6-chloro-2-pyridyl]-5-hexynoic acid, methyl ester White solid, yield=37%.

m.p.=66-72° C.

PREPARATION XI

6-[6-Chloro-3-[(3,5-dimethylphenyl)sulfonylamino]-2-pyridyl]-5-hexynoic acid, methyl ester Orange oil, yield=98%.

¹H NMR (300 MHz, DMSO) δ: 1.74 (quint., 2H); 2.30 (s, 6H); 2.40 (t, 2H); 2.42 (t, 2H); 3.61 (s, 3H); 7.28 (s, 1H); 7.33 (s, 2H); 7.45 (d, 1H); 7.70 (d, 2H); 10.07 (s, 1H).

PREPARATION XII

6-[6-Chloro-3-[(2,5-dimethoxyphenyl)sulfonylamino]-2-pyridyl]-5-hexynoic acid, methyl ester Orange solid, yield=84%.

m.p.=78-82° C.

PREPARATION XIII

6-[6-Chloro-3-[(1-naphtalenyl)sulfonylamino]-2-pyridyl]-5-hexynoic acid, methyl ester Orange solid, yield=98%.

m.p.=117° C.

PREPARATION XIV

6-[6-Chloro-3-[(3,4-dihydro-4-methyl-2H-1,4-benzoxazin-7-yl)sulfonyl-amino]-2-pyridyl]-5-hexynoic acid, methyl ester Brown oil, yield=74%.
$^1$H NMR (300 MHz, DMSO-$d_6$) δ: 1.75 (quint., 2H); 2.41 (m, 4H); 2.78 (s, 3H); 3.28 (m, 2H); 3.61 (s, 3H); 4.27 (m, 2H); 6.78 (d, 1H); 6.88 (s, 1H); 6.89 (d, 1H); 7.44 (d, 1H); 7.71 (d, 1H); 9.80 (s, 1H).

By working in a manner similar to that of Preparation VI, starting with the ester according to Preparation VIII and the Appropriate Sulfonyl Chlorides, the Following Compounds are Obtained:

PREPARATION XV

5-[3-[(5-Benzodioxolylsulfonyl)amino]-6-chloro-2-pyridyl]-4-pentynoic acid, methyl ester Brown solid, yield=92%.
m.p.=133° C.

PREPARATION XVI

5-[3-[(6-Benzothiazolylsulfonyl)amino]-6-chloro-2-pyridyl]-4-pentynoic acid, methyl ester Yellow solid, yield=49%.
m.p.=137° C.

PREPARATION XVII

2-[[3-(3-Amino-6-chloro-2-pyridyl)-2-propynyl]oxy] propanoic acid, ethyl ester

By working in a manner similar to that of Preparation V, starting with the ethyl ester of 2-(2-propynyloxy)propanoic acid, the expected product is obtained in the form of a brown solid (yield=73%).
m.p.=70° C.

PREPARATION XVIII

N-(6-Chloro-2-iodo-3-pyridyl)-3-methoxybenzenesulfonamide

By working in a manner similar to that of Preparation VII, starting with the compound according to Preparation I and 3-methoxybenzenesulfonyl chloride, the expected product is obtained in the form of a white solid (yield=96%).
m.p.=154° C.

PREPARATION XIX

2-[[3-[3-Amino-6-(trifluoromethyl)-2-pyridyl]-2-propynyl]oxy]-2-methylpropanoic acid, methyl ester By working in a manner similar to that of Preparation V, starting with the compound according to Preparation IV and the methyl ester of 2-methyl-2-(2-propynyloxy)propanoic acid, the expected product is obtained in the form of a yellow oil (yield=56%).
$^1$H NMR (250 MHz, DMSO-$d_6$) δ: 7.50 (d, 1H); 7.18 (d, 1H); 6.23 (s, 2H); 4.44 (s, 2H); 3.68 (s, 3H); 1.42 (s, 6H).

PREPARATION XX

2-[[3-[3-Amino-6-(trifluoromethyl)-2-pyridyl]-2-propynyl]oxy]propanoic acid, ethyl ester 800 mg (2.78 mM) of the compound according to Preparation IV, 78 mg (0.28 mM) of tricyclohexylphosphine, 20 ml of dimethylformamide, 97 mg (0.14 mM) of dichlorobis (triphenylphosphine)palladium, 26 mg (0.14 mM) of cuprous iodide and 8 ml of t-butylamine are mixed together. 1.09 g (7 mM) of the ethyl ester of 2-(2-propynyloxy)propanoic acid are then added with stirring, at room temperature, and the reaction mixture is stirred for 20 hours at 45-50° C. The reaction mixture is then cooled, diluted with water and extracted several times with ethyl acetate. The combined organic phases are washed with sodium chloride solution, dried over magnesium sulfate and concentrated under reduced pressure. The crude product obtained is purified by chromatography on silica gel, eluting with a toluene/ethyl acetate mixture (9/1 and then 8/2; v/v). The expected product is thus obtained in the form of an oil (yield: 76%).
$^1$H NMR (300 MHz, DMSO-$d_6$) δ: 7.51 (d, 1H); 7.18 (d, 1H); 6.27 (s, 2H); 4.58 (d, 1H); 4.48 (d, 1H); 4.23 (q, 1H); 4.12 (q, 2H); 1.31 (d, 3H); 1.20 (t, 3H).

PREPARATION XXI

5-[3-Amino-6-(trifluoromethyl)-2-pyridyl]-4-pentynoic acid, methyl ester

By working in a manner similar to that of Preparation V, starting with the compound according to Preparation IV and the methyl ester of 4-pentynoic acid, the expected product is obtained in the form of an ochre-colored solid (yield=81%).
m.p.=90° C.

PREPARATION XXII

6-[3-Amino-6-(trifluoromethyl)-2-pyridyl]-5-hexynoic acid, methyl ester

By working in a manner similar to that of Preparation XXI, starting with the methyl ester of 5-hexynoic acid, the expected product is obtained in the form of a brown solid (yield=94%).
m.p.=49° C.

PREPARATION XXIII 6-(3-Amino-6-chloro-2-pyridyl)-6-heptynoic acid, methyl ester By working in a manner similar to that of Preparation V, starting with the methyl ester of 6-heptynoic acid, the expected product is obtained in the form of a yellow oil (yield=85%).
$^1$H NMR (300 MHz, DMSO-$d_6$) δ: 7.09 (s, 2H); 5.60 (s, 2H); 3.60 (s, 3H); 2.50 (m, 2H); 2.37 (t, 2H); 1.63 (m, 4H).

By working in a manner similar to that of Preparation VII, starting with the compound according to Preparation I and the appropriate sulfonyl chlorides, the following aryl or heteroarylsulfonamides are obtained:

PREPARATION XXIV

N-(6-Chloro-2-iodo-3-pyridyl)-4-ethylbenzenesulfonamide

Yellow solid, yield=88%.
m.p.=141° C.

PREPARATION XXV

N-(6-Chloro-2-iodo-3-pyridyl)-4-methoxybenzenesulfonamide

Brown solid, yield=98%.
m.p.=93° C.

PREPARATION XXVI

N-(6-Chloro-2-iodo-3-pyridyl)-2,3-dichlorobenzenesulfonamide

Beige-colored solid, yield=99%.
m.p.>260° C.

PREPARATION XXVII

N-(6-Chloro-2-iodo-3-pyridyl)-4-(1-methylethyl)benzenesulfonamide

Yellow solid, yield=93%.
m.p.=132° C.

PREPARATION XXVIII

N-(6-Chloro-2-iodo-3-pyridyl)-1-naphthalenesulfonamide

White solid, yield=54%.
m.p.=135° C.

PREPARATION XXIX

N-(6-Chloro-2-iodo-3-pyridyl)-8-quinolinesulfonamide

Pink solid, yield=14%.
m.p.=199° C.

PREPARATION XXX

N-(6-Chloro-2-iodo-3-pyridyl)-2,5-dimethoxybenzenesulfonamide

Beige-colored solid, yield=99%.
m.p.=147° C.

PREPARATION XXXI

N-(6-Chloro-2-iodo-3-pyridyl)-1,3-benzodioxole-5-sulfonamide

White solid, yield=95%.
m.p.=187° C.

PREPARATION XXXII

N-(6-Chloro-2-iodo-3-pyridyl)-2,3-dihydro-1,4-benzodioxine-6-sulfonamide

Yellow solid, yield=94%.
m.p.=122° C.

PREPARATION XXXIII

N-(6-Chloro-2-iodo-3-pyridyl)-2,3-dihydro-5-benzofuransulfonamide

White solid, yield=94%.
m.p.=187° C.

PREPARATION XXXIV

N-(6-Chloro-2-iodo-3-pyridyl)-3,5-dimethylbenzenesulfonamide

Beige-colored solid, yield=99%.
m.p.=138° C.

PREPARATION XXXV

N-(6-Chloro-2-iodo-3-pyridyl)-3,4-dihydro-4-methyl-2H-1,4-benzoxazine-7-sulfonamide White solid, yield=99%.
m.p.=139° C.

PREPARATION XXXVI

N-(2-Bromo-6-methyl-3-pyridyl)benzenesulfonamide

By working in a manner similar to that of Preparation VII, starting with 3-amino-2-bromo-6-methylpyridine, the expected product is obtained in the form of a beige-colored solid (yield=95%).

$^1$H NMR (250 MHz, DMSO-d$_6$) δ: 10.05 (s, 1H); 7.70 (m, 3H); 7.61 (d, 2H); 7.47 (d, 1H); 7.25 (d, 1H); 2.39 (s, 3H).

PREPARATION XXXVII

3-Amino-2-bromo-6-methoxypyridine

A mixture of 1.83 g (14.7 mM) of 5-amino-2-methoxypyridine and 1.21 g (14.7 mM) of sodium acetate in 12 ml of acetic acid is prepared and 0.75 ml (14.7 mM) of bromine is added gently, with stirring and while maintaining at room temperature. The reaction mixture is kept stirring for 30 minutes, at room temperature, and 200 ml of saturated sodium thiosulfate solution are then added. The aqueous phase obtained is extracted twice with ethyl acetate. The combined organic phases are dried over magnesium sulfate and concentrated under reduced pressure. 3 g of the expected compound are obtained in the form of a violet-colored solid (quantitative yield).

$^1$H NMR (250 MHz, DMSO-d$_6$) δ: 7.18 (d, 1H); 6.64 (d, 1H); 4.91 (s, 2H); 3.71 (s, 3H).

PREPARATION XXXVIII (2-Bromo-6-methoxy-3-pyridyl)benzenesulfonamide

By working in a manner similar to that of Preparation VII, starting with 3-amino-2-bromo-6-methoxypyridine, the expected product is obtained in the form of a brown solid (yield=50%).

$^1$H NMR (250 MHz, DMSO-d$_6$) δ: 9.92 (s, 1H); 7.67 (m, 3H); 7.57 (m, 2H); 7.45 (d, 1H); 6.84 (d, 1H); 3.80 (s, 3H).

PREPARATION XXXIX

3-Amino-2-iodo-6-methoxypyridine

By working in a manner similar to that of Preparation IV, starting with 5-amino-2-methoxypyridine, the expected product is obtained in the form of a brown oil (yield=6%).

$^1$H NMR (300 MHz, DMSO-d$_6$) δ: 7.08 (d, 1H); 6.62 (d, 1H); 4.81 (s, 2H); 3.71 (s, 3H).

PREPARATION XL (2-Iodo-6-methoxy-3-pyridyl)benzenesulfonamide

By working in a manner similar to that of Preparation VII, starting with 3-amino-2-iodo-6-methoxypyridine, the expected product is obtained in the form of a brown solid (yield=91%).

$^1$H NMR (250 MHz, DMSO-d$_6$) δ: 9.84 (s, 1H); 7.65 (m, 5H); 7.17 (d, 1H); 6.77 (d, 1H); 3.79 (s, 3H).

PREPARATION XLI

N-(2-Bromo-6-methyl-3-pyridyl)-6-benzothiazole-sulfonamide

By working in a manner similar to that of Preparation VII, starting with 3-amino-2-bromo-6-methylpyridine and 6-benzothiazolesulfonyl chloride, the expected product is obtained in the form of a beige-colored paste (yield=35%).

$^1$H NMR (250 MHz, DMSO-d$_6$) δ: 10.20 (s, 1H); 9.63 (s, 1H); 8.61 (d, 1H); 8.25 (d, 1H); 7.85 (dd, 1H); 7.49 (d, 1H); 7.26 (d, 1H); 2.39 (s, 3H).

PREPARATION XLII

N-(6-Chloro-2-iodo-3-pyridyl)-3-pyridinesulfonamide

By working in a manner similar to that of Preparation XVIII, starting with 3-pyridinesulfonyl chloride, the expected product is obtained in the form of a pasty compound, which is used without further purification for the preparation of the compound according to Example 252.

PREPARATION XLIII

N-(6-Chloro-2-iodo-3-pyridyl)-6-quinolinesulfonamide

By working in a manner similar to that of Preparation XVIII starting with 6-quinolinesulfonyl chloride, the expected product is obtained in the form of a white solid (yield=99%)

m.p.>250° C.

PREPARATION XLIV

N-(2-Iodo-6-chloro-3-pyridyl)-6-benzothiazole-sulfonamide

By working in a manner similar to that of Example 50, starting with 3-amino-2-iodo-6-chloropyridine and 6-benzothiazolesulfonyl chloride, the expected product is obtained in the form of an orange-colored solid (yield=33%).

m.p.=191° C.

PREPARATION XLV 5-(Trifluoromethyl)-1H-pyrrolo[3,2-b]pyridine-2-butanoic acid, methyl ester By working in a manner similar to that of Example 3, starting with the methyl ester according to Preparation XXII, the expected product is obtained in the form of a beige-colored solid (yield=66%).

m.p.=137° C.

PREPARATION XLVI

6-[6-Chloro-3-[[(4-fluoro-3-nitrophenyl)sulfonyl]amino]-2-pyridyl]-5-hexynoic acid, methyl ester By working in a manner similar to that of Preparation VI, starting with 4-fluoro-3-nitrobenzenesulfonyl chloride, the expected product is obtained in the form of a yellow oil (yield=31%).

$^1$H NMR (300 MHz, DMSO-d$_6$) δ: 10.63 (s, 1H); 8.41 (dd, 1H); 8.06 (m, 1H); 7.75 (m, 2H); 7.46 (d, 1H); 3.61 (s, 3H); 2.39 (m, 4H); 1.72 (quint., 2H).

PREPARATION XLVII

6-[3-[[(2,1,3-Benzothiadiazol-4-yl)sulfonyl]amino]-6-chloro-2-pyridyl]-5-hexynoic acid, methyl ester By working in a manner similar to that of Preparation VI, starting with 2,1,3-benzothiadiazole-4-sulfonyl chloride, the expected compound is obtained in the form of a beige-colored solid (yield=64%).

$^1$H NMR (250 MHz, DMSO-d$_6$) δ: 10.36 (s, 1H); 8.40 (d, 1H); 8.18 (d, 1H); 7.84 (m, 2H); 7.48 (d, 1H); 3.62 (s, 3H); 2.26 (t, 2H); 2.01 (t, 2H); 1.47 (quint., 2H).

EXAMPLE 5

2-[[5-Chloro-1-(phenylsulfonyl)-1H-pyrrolo[3,2-b]pyrid-2-yl]-methoxy]propanoic acid, ethyl ester By working in a manner similar to that of Example 1, starting with the ethyl ester of 2-(2-propynyloxy)propanoic acid, the expected compound is obtained in the form of a yellow oil (yield=62%).

$^1$H NMR (300 MHz, DMSO-d$_6$) δ: 1.18 (t, 3H); 1.31 (d, 3H); 4.12 (q, 2H); 4.24 (q, 1H); 4.92 (d, 1H); 5.05 (d, 1H); 6.95 (s, 1H); 7.43 (d, 1H); 7.60 t, 2H); 7.74 (t, 1H); 8.02 (d, 2H); 8.42 (d, 1H).

EXAMPLE 6

2-[[5-Chloro-1-(phenylsulfonyl)-1H-pyrrolo[3,2-b]pyrid-2-yl]-methoxy]propanoic acid By working in a manner similar to that of Example 2, starting with the ester obtained according to Example 5, the expected compound is obtained in the form of a white solid (yield=57%).

m.p.=153-155° C.

EXAMPLE 7

2-[[5-Chloro-1-(phenylsulfonyl)-1H-pyrrolo[3,2-b]pyrid-2-yl]-methoxy]-2-methylpropanoic acid, methyl ester By working in a manner similar to that of Example 1, starting with the methyl ester of 2-methyl-2-(2-propynyloxy)propanoic acid, the expected compound is obtained in the form of a white solid (yield=20%).

m.p.=84-87° C.

EXAMPLE 8

2-[[5-Chloro-1-(phenylsulfonyl)-1H-pyrrolo[3,2-b]pyrid-2-yl]-methoxy]-2-methylpropanoic acid By working in a manner similar to that of Example 2, starting with the ester obtained according to Example 7, the expected compound is obtained in the form of a white solid (yield=57%).
m.p.=183-185° C.

EXAMPLE 9

5-Chloro-1-(phenylsulfonyl)-1H-pyrrolo[3,2-b]pyridine-2-butanoic acid, methyl ester By working in a manner similar to that of Example 1, starting with the methyl ester of 5-hexynoic acid, the expected compound is obtained in the form of a yellow solid (yield=38%).
m.p.=85-90° C.

EXAMPLE 10

5-Chloro-1-(phenylsulfonyl)-1H-pyrrolo[3,2-b]pyridine-2-butanoic acid

By working in a manner similar to that of Example 2, starting with the ester obtained according to Example 9, the expected compound is obtained in the form of a beige-colored solid (yield=38%).
m.p.=160-164° C.

EXAMPLE 11

3-(1-Benzenesulfonyl-5-chloro-1H-pyrrolo[3,2-b]pyrid-2-yl)-2,2-dimethylpropanoic acid, methyl ester By working in a manner similar to that of Example 1, starting with the methyl ester of 2,2-dimethyl-4-pentynoic acid, the expected compound is obtained in the form of a yellow oil (yield=82%).
$^1$H NMR (300 MHz, DMSO-$d_6$) δ: 1.22 (s, 6H); 3.41 (s, 2H); 3.62 (s, 3H); 6.58 (s, 1H); 7.40 (d, 1H); 7.59 (t, 2H); 7.72 (t, 1H); 7.82 (d, 2H); 8.42 (d, 1H).

EXAMPLE 12

3-(1-Benzenesulfonyl-5-chloro-1H-pyrrolo[3,2-b]pyrid-2-yl)-2,2-dimethylpropanoic acid By working in a manner similar to that of Example 2, starting with the ester obtained according to Example 11, the expected compound is obtained in the form of a white solid (yield=18%).
m.p.=208-211° C.

EXAMPLE 13

2-[[1-(Phenylsulfonyl)-5-(trifluoromethyl)-1H-pyrrolo[3,2-b]pyrid-2-yl]-methoxy]propanoic acid, ethyl ester By working in a manner similar to that of Example 1, starting with the compound according to Preparation VII and the ethyl ester of 2-(2-propynyloxy)propanoic acid, the expected compound is obtained in the form of a colorless oil (yield=63%).
$^1$H NMR (300 MHz, DMSO-$d_6$) δ: 1.17 (t, 3H); 1.31 (d, 3H); 4.11 (q, 2H); 4.23 (q, 1H); 4.97 (d, 1H); 5.10 (d, 1H); 7.12 (s, 1H); 7.61 (t, 2H); 7.75 (t, 1H); 7.80 (d, 1H); 8.06 (d, 2H); 8.63 (d, 1H).

EXAMPLE 14

2-[[1-(Phenylsulfonyl)-5-(trifluoromethyl)-1H-pyrrolo[3,2-b]pyrid-2-yl]-methoxy]propanoic acid By working in a manner similar to that of Example 2, starting with the ester obtained according to Example 13, the expected compound is obtained in the form of a white solid (yield=56%).
m.p.=53-57° C.

EXAMPLE 15

2-[[1-(Phenylsulfonyl)-5-(trifluoromethyl)-1H-pyrrolo[3,2-b]pyrid-2-yl]methoxy]-2-methylpropanoic acid, methyl ester By working in a manner similar to that of Example 13, starting with the compound according to Preparation VII and the methyl ester of 2-methyl-2-(2-propynyloxy)propanoic acid, the expected compound is obtained in the form of a yellow oil (yield=30%).
$^1$H NMR (300 MHz, DMSO-$d_6$) δ: 1.44 (s, 6H); 3.65 (s, 3H); 4.93 (s, 2H); 7.10 (s, 1H); 7.63 (t, 2H); 7.76 (t, 1H); 7.83 (d, 1H); 8.05 (d, 2H); 8.64 (d, 1H).

EXAMPLE 16

2-[[1-(Phenylsulfonyl)-5-(trifluoromethyl)-1H-pyrrolo[3,2-b]pyrid-2-yl]methoxy]-2-methylpropanoic acid By working in a manner similar to that of Example 2, starting with the ester obtained according to Example 15, the expected compound is obtained in the form of a beige-colored solid (yield=45%).
m.p.=122-125° C.

EXAMPLE 17

1-(Phenylsulfonyl)-5-(trifluoromethyl)-1H-pyrrolo[3,2-b]pyridine-2-propanoic acid, methyl ester By working in a manner similar to that of Example 13, starting with the methyl ester of 4-pentynoic acid, the expected compound is obtained in the form of a beige-colored solid (yield=91%).
m.p.=119° C.

EXAMPLE 18

1-(Phenylsulfonyl)-5-(trifluoromethyl)-1H-pyrrolo[3,2-b]pyridine-2-propanoic acid By working in a manner similar to that of Example 2, starting with the ester obtained according to Example 17, the expected compound is obtained in the form of a white solid (yield=53%).
m.p.=180° C.

EXAMPLE 19

1-(Phenylsulfonyl)-5-(trifluoromethyl)-1H-pyrrolo[3,2-b]pyridine-2-butanoic acid, methyl ester By working in a manner similar to that of Example 13, starting with the methyl ester of 5-hexynoic acid, the expected compound is obtained in the form of a beige-colored solid (yield=88%).
m.p.=95° C.

EXAMPLE 20

1-(Phenylsulfonyl)-5-(trifluoromethyl)-1H-pyrrolo[3,2-b]pyridine-2-butanoic acid By working in a manner similar to that of Example 2, starting with the ester obtained according to Example 19, the expected compound is obtained in the form of a white solid (yield=58%).
m.p.=168° C.

EXAMPLE 21

1-[(2-Amino-6-benzothiazolyl)sulfonyl]-5-chloro-1H-pyrrolo[3,2-b]pyridine-2-butanoic acid, methyl ester By working in a manner similar to that of Example 3, starting with the compound according to Preparation X, the expected compound is obtained in the form of a yellow solid (yield=63%).
m.p.=85-90° C.

EXAMPLE 22

1-[(2-Amino-6-benzothiazolyl)sulfonyl]-5-chloro-1H-pyrrolo[3,2-b]pyridine-2-butanoic acid By working in a manner similar to that of Example 2, starting with the compound obtained according to Example 21, the expected product is obtained in the form of a white solid (yield=82%).
m.p.>250° C.

EXAMPLE 23

1-(1,3-Benzodioxol-5-ylsulfonyl)-5-chloro-1H-pyrrolo[3,2-b]pyridine-2-butanoic acid, methyl ester By working in a manner similar to that of Example 3, starting with the compound according to Preparation IX, the expected compound is obtained in the form of a yellow solid (yield=74%).
m.p.=120° C.

EXAMPLE 24

1-(1,3-Benzodioxol-5-ylsulfonyl)-5-chloro-1H-pyrrolo[3,2-b]pyridine-2-butanoic acid By working in a manner similar to that of Example 2, starting with the compound obtained according to Example 23, the expected product is obtained in the form of a beige-colored solid (yield=95%).
m.p.=160° C.

EXAMPLE 25

5-Chloro-1-[(3,5-dimethylphenyl)sulfonyl]-1H-pyrrolo[3,2-b]pyridine-2-butanoic acid, methyl ester By working in a manner similar to that of Example 3, starting with the compound according to Preparation XI, the expected compound is obtained in the form of a brown solid (yield=99%).
m.p.=138° C.

EXAMPLE 26

5-Chloro-1-[(3,5-dimethylphenyl)sulfonyl]-1H-pyrrolo[3,2-b]pyridine-2-butanoic acid By working in a manner similar to that of Example 2, starting with the compound obtained according to Example 25, the expected product is obtained in the form of a beige-colored solid (yield=88%).
m.p.=200° C.

EXAMPLE 27

5-Chloro-1-[(2,5-dimethoxyphenyl)sulfonyl]-1H-pyrrolo[3,2-b]pyridine-2-butanoic acid, methyl ester By working in a manner similar to that of Example 3, starting with the compound according to Preparation XII, the expected compound is obtained in the form of a beige-colored solid (yield=94%).
m.p.=102° C.

EXAMPLE 28

5-Chloro-1-[(2,5-dimethoxyphenyl)sulfonyl]-1H-pyrrolo[3,2-b]pyridine-2-butanoic acid By working in a manner similar to that of Example 2, starting with the compound obtained according to Example 27, the expected product is obtained in the form of a white solid (yield=95%).
m.p.=227-231° C.

EXAMPLE 29

5-Chloro-1-(1-naphtalenylsulfonyl)-1H-pyrrolo[3,2-b]pyridine-2-butanoic acid, methyl ester By working in a manner similar to that of Example 3, starting with the compound according to Preparation XIII, the expected compound is obtained in the form of a yellow oil (yield=86%).
$^1$H NMR (300 MHz, DMSO-$d_6$) δ: 1.83 (quint., 2H); 2.34 (t, 2H); 2.88 (t, 2H); 3.52 (s, 3H); 6.83 (s, 1H); 7.39 (d, 1H); 7.71 (m, 4H); 8.14 (m, 1H); 8.30 (m, 1H); 8.37 (m, 2H).

EXAMPLE 30

5-Chloro-1-(1-naphtalenylsulfonyl)-1H-pyrrolo[3,2-b]pyridine-2-butanoic acid

By working in a manner similar to that of Example 2, starting with the compound obtained according to Example 29, the expected product is obtained in the form of a white solid (yield=96%).
m.p.=202-206° C.

EXAMPLE 31

5-Chloro-1-[(3,4-dihydro-4-methyl-2H-1,4-benzox-azin-7-yl)sulfonyl]-1H-pyrrolo[3,2-b]pyridine-2-butanoic acid, methyl ester By working in a manner similar to that of Example 3, starting with the compound according to Preparation XIV, the expected compound is obtained in the form of a white solid (yield=78%).
m.p.=106-110° C.

EXAMPLE 32

5-Chloro-1-[(3,4-dihydro-4-methyl-2H-1,4-benzox-azin-7-yl)sulfonyl]-1H-pyrrolo[3,2-b]pyridine-2-butanoic acid By working in a manner similar to that of Example 2, starting with the compound obtained according to Example 31, the expected product is obtained in the form of a white solid (yield=98%).
m.p.=180-183° C.

EXAMPLE 33

1-(1,3-Benzodioxol-5-ylsulfonyl)-5-chloro-1H-pyrrolo[3,2-b]pyridine-2-propanoic acid, methyl ester By working in a manner similar to that of Example 3, starting with the compound according to Preparation XV, the expected compound is obtained in the form of a yellow oil (yield=76%).
$^1$H NMR (300 MHz, DMSO-$d_6$) δ: 2.84 (t, 2H); 3.31 (t, 2H); 3.47 (t, 2H); 3.62 (s, 3H); 6.16 (s, 2H); 6.72 (s, 1H); 7.09 (d, 1H); 7.37 (d, 1H); 7.38 (s, 1H); 7.51 (dd, 1H); 8.40 (s, 1H).

EXAMPLE 34

1-(1,3-Benzodioxol-5-ylsulfonyl)-5-chloro-1H-pyrrolo[3,2-b]pyridine-2-propanoic acid By working in a manner similar to that of Example 2, starting with the compound obtained according to Example 33, the expected product is obtained in the form of a brown solid (yield=98%).
m.p.=186° C.

EXAMPLE 35

1-(6-Benzothiazolylsulfonyl)-5-chloro-1H-pyrrolo[3,2-b]pyridine-2-propanoic acid, methyl ester By working in a manner similar to that of Example 3, starting with the compound according to Preparation XVI, the expected compound is obtained in the form of a white solid (yield=57%).
m.p.=146° C.

EXAMPLE 36

1-(6-Benzothiazolylsulfonyl)-5-chloro-1H-pyrrolo[3,2-b]pyridine-2-propanoic acid By working in a manner similar to that of Example 2, starting with the compound obtained according to Example 35, the expected product is obtained in the form of a white solid (yield=90%).
m.p.=248° C.

EXAMPLE 37

5-Chloro-1-(phenylsulfonyl)-1H-pyrrolo[3,2-b]pyridine-2-propanoic acid, sodium salt 1.46 g (4 mM) of the acid obtained according to Example 2 are mixed in 12 ml of tetrahydrofuran and 8 ml (4 mM) of a 0.5 N solution of sodium hydroxide in water are added. The reaction medium is stirred for 2 hours at room temperature and then concentrated under reduced pressure. The oily residue is triturated from methanol and the white precipitate formed is separated out by filtration and dried under vacuum. The expected salt is obtained in the form of a pulverulent white solid (yield=98%).
m.p.=200° C.

EXAMPLE 38

2-[[1-(2,1,3-Benzothiadiazol-5-ylsulfonyl)-5-chloro-1H-pyrrolo[3,2-b]pyrid-2-yl]methoxy]propanoic acid, ethyl ester By working in a manner similar to that of Preparation VI, starting with the ester according to Preparation XVII and 2,1,3-benzothiadiazole-5-sulfonyl chloride, the expected compound is obtained in the form of an orange-colored solid (yield=46%).
m.p.=77-79° C.

EXAMPLE 39

2-[[1-(2,1,3-Benzothiadiazol-5-ylsulfonyl)-5-chloro-1H-pyrrolo[3,2-b]pyrid-2-yl]methoxy]propanoic acid By working in a manner similar to that of Example 2, starting with the ester obtained according to Example 38, the expected compound is obtained in the form of a white solid (yield=16%).
m.p.=192-194° C.

EXAMPLE 40

2-[[5-Chloro-1-[(2-methyl-7-benzothiazolyl)sulfonyl]-1H-pyrrolo[3,2-b]pyrid-2-yl]methoxy]propanoic acid, ethyl ester By working in a manner similar to that of Preparation VI, starting with the ester according to Preparation XVII and 2-methyl-7-benzothiazolesulfonyl chloride, the expected compound is obtained in the form of a colorless oil (yield=50%).
$^1$H NMR (300 MHz, DMSO-$d_6$) δ: 8.32 (d, 1H); 8.27 (d, 1H); 7.94 (d, 1H); 7.67 (t, 1H); 7.43 (d, 1H); 7.00 (s, 1H); 5.02 (d, 1H); 4.88 (d, 1H); 4.13 (q, 1H); 4.07 (q, 2H); 2.85 (s, 3H); 1.15 (m, 6H).

EXAMPLE 41

2-[[5-Chloro-1-[(2-methyl-7-benzothiazolyl)sulfonyl]-1H-pyrrolo[3,2-b]pyrid-2-yl]methoxy]propanoic acid By working in a manner similar to that of Example 2, starting with the ester obtained according to Example 40, the expected compound is obtained in the form of a white solid (yield=28%).
m.p.=203-205° C.

EXAMPLE 42

2-[[5-Chloro-1-[(3-methoxyphenyl)sulfonyl]-1H-pyrrolo[3,2-b]pyrid-2-yl]methoxy]-2-methylpropanoic acid, methyl ester By working in a manner similar to that of Example 1, starting with the compound according to Preparation XVIII and the methyl ester of 2-methyl-2-(2-propynyloxy)propanoic acid, the expected compound is obtained in the form of a white solid (yield=33%).
m.p.=153° C.

EXAMPLE 43

2-[[5-Chloro-1-[(3-methoxyphenyl)sulfonyl]-1H-pyrrolo[3,2-b]pyrid-2-yl]methoxy]-2-methylpropanoic acid A solution of 186 mg (0.41 mM) of the ester obtained according to Example 42 in 7.5 ml of acetic acid is prepared and 0.75 ml of concentrated hydrochloric acid is added, with stirring and at room temperature. The reaction medium is maintained under gentle reflux for 18 hours and then concentrated under reduced pressure. The evaporation residue is taken up in water and extracted with dichloromethane. The organic phase is washed with water, dried over magnesium sulfate and concentrated under reduced pressure. The crude product is purified by chromatography on silica gel, eluting with a dichloromethane/methanol mixture (gradient from 99/1 to 90/10, v/v). The expected acid is thus obtained in the form of a beige-colored solid (yield=70%).
m.p.=130° C.

EXAMPLE 44

2-[[1-[(2-Acetylamino-6-benzothiazolyl)sulfonyl]-5-chloro-1H-pyrrolo[3,2-b]pyrid-2-yl]methoxy]propanoic acid, ethyl ester By working in a manner similar to that of Preparation VI, starting with the ester according to Preparation XVII and 2-acetylamino-6-benzothiazolesulfonyl chloride, the expected compound is obtained in the form of a white solid (yield=25%).
m.p.=100-102° C.

EXAMPLE 45

2-[[1-[(2-Acetylamino-6-benzothiazolyl)sulfonyl]-5-chloro-1H-pyrrolo-[3,2-b]pyrid-2-yl]methoxy]propanoic acid By working in a manner similar to that of Example 43, starting with the ester obtained according to Example 44, the expected compound is obtained in the form of a white solid (yield=25%).
m.p.=257-260° C.

EXAMPLE 46

2-[[1-[(2-Amino-6-benzothiazolyl)sulfonyl]-5-chloro-1H-pyrrolo[3,2-b]pyrid-2-yl]methoxy]propanoic acid, ethyl ester By working in a manner similar to that of Preparation VI, starting with the ester according to Preparation XVII and 2-amino-6-benzothiazolesulfonyl chloride, the expected compound is obtained in the form of a yellow solid (yield=25%).
m.p.=86-88° C.

EXAMPLE 47

2-[[1-[(2-Amino-6-benzothiazolyl)sulfonyl]-5-chloro-1H-pyrrolo[3,2-b]pyrid-2-yl]methoxy]propanoic acid By working in a manner similar to that of Example 43, starting with the ester obtained according to Example 46, the expected compound is obtained in the form of a white solid (yield=65%).
m.p.=218-220° C.

EXAMPLE 48

2-[[1-(6-Benzothiazolylsulfonyl)-5-(trifluoromethyl)-1H-pyrrolo[3,2-b]pyrid-2-yl]methoxy]-2-methylpropanoic acid, methyl ester By working in a manner similar to that of Preparation VI, starting with the compound according to Preparation XIX and 6-benzothiazolesulfonyl chloride, the expected compound is obtained in the form of a white solid (yield=13%).
m.p.=124-127° C.

EXAMPLE 49

2-[[1-(6-Benzothiazolylsulfonyl)-5-(trifluoromethyl)-1H-pyrrolo[3,2-b]pyrid-2-yl]methoxy]-2-methylpropanoic acid By working in a manner similar to that of Example 2, starting with the ester obtained according to Example 48, the expected compound is obtained in the form of a white solid (yield=16%).
m.p.=180-182° C.

EXAMPLE 50

2-[[1-(6-Benzothiazolylsulfonyl)-5-chloro-1H-pyrrolo[3,2-b]pyrid-2-yl]-methoxy]propanoic acid, ethyl ester A solution of 350 mg (1.24 mM) of the ester according to Preparation XVII in 8 ml of pyridine is prepared and 550 mg (2.35 mM) of 6-benzothiazolesulfonyl chloride are added, with stirring and at 0° C. The reaction medium is stirred at room temperature for 24 hours and then diluted with ethyl acetate. This organic phase is washed with 2 N hydrochloric acid solution and then with water, dried over magnesium sulfate and concentrated under reduced pressure. The oil obtained is taken up in 10 ml of THF and 2.6 ml (2.6 mM) of tetrabutylammonium fluoride as a 1 M solution in THF are gradually added to this solution cooled to 0° C. The reaction mixture is stirred for 24 hours at 4° C., and then diluted in DCM. The organic phase obtained is washed with N hydrochloric acid solution, and then with water, dried over magnesium sulfate and concentrated under reduced pressure. The crude product is purified by chromatography on silica gel, eluting with a toluene/ethyl acetate mixture (95/5 and then 9/1; v/v). The expected product is thus obtained in the form of a yellow oil (yield=31%).

¹H NMR (250 MHz, DMSO-d₆) δ: 9.68 (s, 1H); 9.11 (d, 1H); 8.50 (d, 1H); 8.23 (d, 1H); 8.10 (dd, 1H); 7.43 (d, 1H); 6.96 (s, 1H); 5.08 (d, 1H); 4.96 (d, 1H); 4.25 (q, 1H); 4.12 (q, 2H); 1.28 (d, 3H); 1.19 (t, 3H).

EXAMPLE 51

2-[[1-(6-Benzothiazolylsulfonyl)-5-chloro-1H-pyrrolo[3,2-b]pyrid-2-yl]-methoxy]propanoic acid By working in a manner similar to that of Example 2, starting with the ester obtained according to Example 50, the expected compound is obtained in the form of a white solid (yield=40%).
m.p.=179° C.

EXAMPLE 52

2-[[1-(6-Benzothiazolylsulfonyl)-5-(trifluoromethyl)-1H-pyrrolo[3,2-b]pyrid-2-yl]methoxy]propanoic acid, ethyl ester A solution of 140 mg (0.443 mM) of the compound according to Preparation XX in 2 ml of pyridine is prepared and 228 mg (0.98 mM) of 6-benzothiazolesulfonyl chloride are added. The reaction mixture is stirred at room temperature for 48 hours and then diluted with ethyl acetate. The organic phase obtained is washed successively with water, with N hydrochloric acid, again with water, with sodium bicarbonate solution and finally with sodium chloride solution. After drying over magnesium sulfate and concentrating, 242 mg of the ethyl ester of 2-[[3-[3-(6-benzothiazolylsulfonylamino)-6-(trifluoromethyl)-2-pyridyl]-2-propynyl]oxy]-propanoic acid are obtained, which product is taken up in 5 ml of DCM in a reactor tube adapted for heating by microwave. 100 mg (0.5 mM) of copper acetate monohydrate are added and this mixture is heated at 150° C. for 15 minutes. The reaction medium is cooled, filtered and concentrated under reduced pressure. After purification by chromatography on a column of silica, eluting with a toluene/ethyl acetate mixture (9/1; v/v), the expected compound is obtained in the form of a beige-colored solid (yield=42%).
m.p.=96° C.

EXAMPLE 53

2-[[1-(6-Benzothiazolylsulfonyl)-5-(trifluoromethyl)-1H-pyrrolo[3,2-b]pyrid-2-yl]methoxy]propanoic acid By working in a manner similar to that of Example 2, starting with the ester obtained according to Example 52, the expected compound is obtained in the form of a beige-colored solid (yield=50%).
m.p.=124° C.

EXAMPLE 54

5-Chloro-1-[(2,5-dimethoxyphenyl)sulfonyl]-1H-pyrrolo[3,2-b]pyridine-2-propanoic acid, methyl ester By working in a manner similar to that of Example 52, starting with the compound according to Preparation VIII and 2,5-dimethoxybenzenesulfonyl chloride, the expected compound is obtained in the form of a beige-colored solid (yield=77%).
m.p.=127° C.

EXAMPLE 55

5-Chloro-1-[(2,5-dimethoxyphenyl)sulfonyl]-1H-pyrrolo[3,2-b]pyridine-2-propanoic acid By working in a manner similar to that of Example 2, starting with the ester obtained according to Example 54, the expected compound is obtained in the form of a white solid (yield=71%).
m.p.=204-209° C.

EXAMPLE 56

1-[(2-Amino-6-benzothiazolyl)sulfonyl]-5-chloro-1H-pyrrolo[3,2-b]pyridine-2-propanoic acid, methyl ester By working in a manner similar to that of Example 52, starting with the ester according to Preparation VIII and 2-amino-6-benzothiazolesulfonyl chloride, the expected compound is obtained in the form of a yellow solid (yield=38%).
m.p.=205-215° C.

EXAMPLE 57

1-[(2-Amino-6-benzothiazolyl)sulfonyl]-5-chloro-1H-pyrrolo[3,2-b]pyridine-2-propanoic acid By working in a manner similar to that of Example 2, starting with the ester obtained according to Example 56, the expected compound is obtained in the form of a beige-colored solid (yield=57%).
m.p.>260° C.

EXAMPLE 58

5-Chloro-1-[(3,5-dimethylphenyl)sulfonyl]-1H-pyrrolo[3,2-b]pyridine-2-propanoic acid, methyl ester By working in a manner similar to that of Example 52, starting with the compound according to Preparation VIII and 3,5-dimethylbenzenesulfonyl chloride, the expected compound is obtained in the form of a white solid (yield=86%).
m.p.=182-185° C.

EXAMPLE 59

5-Chloro-1-[(3,5-dimethylphenyl)sulfonyl]-1H-pyrrolo[3,2-b]pyridine-2-propanoic acid By working in a manner similar to that of Example 2, starting with the ester obtained according to Example 58, the expected compound is obtained in the form of a white solid (yield=99%).
m.p.=181-186° C.

EXAMPLE 60

5-Chloro-1-[(3,4-dihydro-4-methyl-2H-1,4-benzoxazin-7-yl)sulfonyl]-1H-pyrrolo[3,2-b]pyridine-2-propanoic acid, methyl ester By working in a manner similar to that of Example 52, starting with the compound according to Preparation VIII and 3,4-dihydro-4-methyl-2H-1,4-benzoxazine-7-sulfonyl chloride, the expected compound is obtained in the form of a yellow oil (yield=87%).

¹H NMR (300 MHz, DMSO-d$_6$) δ: 8.43 (d, 1H); 7.37 (d, 1H); 7.07 (dd, 1H); 6.94 (d, 1H); 6.81 (d, 1H); 6.69 (s, 1H); 4.25 (m, 2H); 3.62 (s, 3H); 3.26 (m, 4H); 2.86 (m, 2H); 2.82 (s, 3H).

EXAMPLE 61

5-Chloro-1-[(3,4-dihydro-4-methyl-2H-1,4-benzoxazin-7-yl)sulfonyl]-1H-pyrrolo[3,2-b]pyridine-2-propanoic acid By working in a manner similar to that of Example 2, starting with the ester obtained according to Example 60, the expected compound is obtained in the form of a white solid (yield=98%).

m.p.=175-185° C.

EXAMPLE 62

5-Chloro-1-(8-quinolylsulfonyl)-1H-pyrrolo[3,2-b]pyridine-2-propanoic acid, methyl ester By working in a manner similar to that of Example 52, starting with the compound according to Preparation VIII and 8-quinolinesulfonyl chloride, the expected compound is obtained in the form of a white solid (yield=59%).

m.p.=120° C.

EXAMPLE 63

5-Chloro-1-(8-quinolylsulfonyl)-1H-pyrrolo[3,2-b]pyridine-2-propanoic acid

By working in a manner similar to that of Example 2, starting with the ester obtained according to Example 62, the expected compound is obtained in the form of a white solid (yield=98%).

m.p.=183° C.

EXAMPLE 64

5-Chloro-1-(1-naphtalenylsulfonyl)-1H-pyrrolo[3,2-b]pyridine-2-propanoic acid, methyl ester By working in a manner similar to that of Example 52, starting with the compound according to Preparation VIII and 1-naphthalenesulfonyl chloride, the expected compound is obtained in the form of a yellow oil (yield=66%).

¹H NMR (250 MHz, DMSO-d$_6$) δ: 8.34 (m, 3H); 8.15 (m, 1H); 7.69 (m, 4H); 7.39 (d, 1H); 6.81 (s, 1H); 3.56 (s, 3H); 3.12 (t, 2H); 2.74 (t, 2H).

EXAMPLE 65

5-Chloro-1-(1-naphtalenylsulfonyl)-1H-pyrrolo[3,2-b]pyridine-2-propanoic acid

By working in a manner similar to that of Example 2, starting with the ester obtained according to Example 64, the expected compound is obtained in the form of a white solid (yield=86%).

m.p.=93° C.

EXAMPLE 66

1-[(1-Acetyl-2,3-dihydro-1H-indol-5-yl)sulfonyl]-5-chloro-1H-pyrrolo-[3,2-b]pyridine-2-propanoic acid, methyl ester By working in a manner similar to that of Example 52, starting with the compound according to Preparation VIII and 1-acetyl-2,3-dihydro-1H-indole-5-sulfonyl chloride, the expected compound is obtained in the form of a brown solid (yield=93%).

m.p.=66° C.

EXAMPLE 67

1-[(1-Acetyl-2,3-dihydro-1H-indol-5-yl)sulfonyl]-5-chloro-1H-pyrrolo-[3,2-b]pyridine-2-propanoic acid By working in a manner similar to that of Example 2, starting with the ester obtained according to Example 66, the expected compound is obtained in the form of a yellow solid (yield=37%).

m.p.=216° C.

EXAMPLE 68

5-Chloro-1-[3-(trifluoromethoxy)phenylsulfonyl]-1H-pyrrolo[3,2-b]pyridine-2-propanoic acid, methyl ester By working in a manner similar to that of Example 52, starting with the compound according to Preparation VIII and 3-(trifluoromethoxy)benzenesulfonyl chloride, the expected compound is obtained in the form of an orange-colored solid (yield=71%).

m.p.=102° C.

EXAMPLE 69

5-Chloro-1-[3-(trifluoromethoxy)phenylsulfonyl]-1H-pyrrolo[3,2-b]pyridine-2-propanoic acid By working in a manner similar to that of Example 2, starting with the ester obtained according to Example 68, the expected compound is obtained in the form of a yellow solid (yield=9%).

m.p.=146° C.

EXAMPLE 70

1-[(3,5-Dimethylphenyl)sulfonyl]-5-(trifluoromethyl)-1H-pyrrolo[3,2-b]pyridine-2-propanoic acid, methyl ester By working in a manner similar to that of Example 52, starting with the compound according to Preparation XXI and 3,5-dimethylbenzenesulfonyl chloride, the expected compound is obtained in the form of a beige-colored solid (yield=51%).

¹H NMR (250 MHz, DMSO-d$_6$) δ: 8.60 (d, 1H); 7.79 (d, 1H); 7.57 (s, 2H); 7.39 (s, 1H); 6.90 (s, 1H); 3.63 (s, 3H); 3.33 (t, 2H); 2.87 (t, 2H); 2.31 (s, 6H).

EXAMPLE 71

1-[(3,5-Dimethylphenyl)sulfonyl]-5-(trifluoromethyl)-1H-pyrrolo[3,2-b]pyridine-2-propanoic acid By working in a manner similar to that of Example 2, starting with the ester obtained according to Example 70, the expected compound is obtained in the form of a white solid (yield=91%).
m.p.=185-189° C.

EXAMPLE 72

1-(8-Quinolylsulfonyl)-5-(trifluoromethyl)-1H-pyrrolo[3,2-b]pyridine-2-propanoic acid, methyl ester By working in a manner similar to that of Example 52, starting with the compound according to Preparation XXI and 8-quinolinesulfonyl chloride, the expected compound is obtained in the form of a white solid (yield=51%).
$^1$H NMR (300 MHz, DMSO-$d_6$) δ: 8.72 (m, 2H); 8.45 (m, 3H); 7.88 (t, 1H); 7.72 (d, 1H); 7.62 (dd, 1H); 6.76 (s, 1H); 3.60 (s, 3H); 3.54 (t, 2H); 2.88 (t, 2H)

EXAMPLE 73

1-(8-Quinolylsulfonyl)-5-(trifluoromethyl)-1H-pyrrolo[3,2-b]pyridine-2-propanoic acid By working in a manner similar to that of Example 2, starting with the ester obtained according to Example 72, the expected compound is obtained in the form of a white solid (yield=56%).
m.p.=216-217° C.

EXAMPLE 74

1-(1-Naphtalenylsulfonyl)-5-(trifluoromethyl)-1H-pyrrolo[3,2-b]pyridine-2-propanoic acid, methyl ester By working in a manner similar to that of Example 52, starting with the compound according to Preparation XXI and 1-naphthalenesulfonyl chloride, the expected compound is obtained in the form of a beige-colored solid (yield=63%).
$^1$H NMR (250 MHz, DMSO-$d_6$) δ: 8.56 (d, 1H); 8.36 (m, 2H); 8.17 (m, 1H); 7.72 (m, 5H); 6.98 (s, 1H); 3.56 (s, 3H); 3.15 (t, 2H); 2.77 (t, 2H).

EXAMPLE 75

1-(1-Naphtalenylsulfonyl)-5-(trifluoromethyl)-1H-pyrrolo[3,2-b]pyridine-2-propanoic acid By working in a manner similar to that of Example 2, starting with the ester obtained according to Example 74, the expected compound is obtained in the form of a white solid (yield=42%).
m.p.=116-117° C.

EXAMPLE 76

5-Chloro-1-(8-quinolylsulfonyl)-1H-pyrrolo[3,2-b]pyridine-2-butanoic acid, methyl ester By working in a manner similar to that of Example 52, starting with the compound according to Preparation V and 8-quinolinesulfonyl chloride, the expected compound is obtained in the form of a white solid (yield=25%).
m.p.=64° C.

EXAMPLE 77

5-Chloro-1-(8-quinolylsulfonyl)-1H-pyrrolo[3,2-b]pyridine-2-butanoic acid

By working in a manner similar to that of Example 2, starting with the ester obtained according to Example 76, the expected compound is obtained in the form of a white solid (yield=99%).
m.p.=186-189° C.

EXAMPLE 78

5-Chloro-1-[(2,2-difluoro-1,3-benzodioxol-5-yl)sulfonyl]-1H-pyrrolo-[3,2-b]pyridine-2-butanoic acid, methyl ester By working in a manner similar to that of Example 76, starting with 2,2-difluoro-1,3-benzodioxole-5-sulfonyl chloride, the expected compound is obtained in the form of a colorless oil (yield=95%).
$^1$H NMR (250 MHz, DMSO-$d_6$) δ: 8.43 (d, 1H); 8.09 (d, 1H); 7.83 (dd, 1H); 7.60 (d, 1H); 7.38 (d, 1H); 6.77 (s, 1H); 3.59 (s, 3H); 3.07 (t, 2H); 2.45 (t, 2H); 1.97 (m, 2H).

EXAMPLE 79

5-Chloro-1-[(2,2-difluoro-1,3-benzodioxol-5-yl)sulfonyl]-1H-pyrrolo-[3,2-b]pyridine-2-butanoic acid By working in a manner similar to that of Example 2, starting with the ester obtained according to Example 78, the expected compound is obtained in the form of a white solid (yield=78%).
m.p.=216° C.

EXAMPLE 80

5-Chloro-1-[(2-methyl-5-benzothiazolyl)sulfonyl]-1H-pyrrolo[3,2-b]pyridine-2-butanoic acid, methyl ester By working in a manner similar to that of Example 76, starting with 2-methyl-5-benzothiazolesulfonyl chloride, the expected compound is obtained in the form of a beige-colored solid (yield=79%).
m.p.=114° C.

EXAMPLE 81

5-Chloro-1-[(2-methyl-5-benzothiazolyl)sulfonyl]-1H-pyrrolo[3,2-b]pyridine-2-butanoic acid By working in a manner similar to that of Example 2, starting with the ester obtained according to Example 80, the expected compound is obtained in the form of a beige-colored solid (yield=98%).
m.p.=173° C.

EXAMPLE 82

5-Chloro-1-[(2-methyl-6-benzothiazolyl)sulfonyl]-1H-pyrrolo[3,2-b]pyridine-2-butanoic acid, methyl ester By working in a manner similar to that of Example 76, starting with 2-methyl-6-benzothiazolesulfonyl chloride, the expected compound is obtained in the form of a beige-colored solid (yield=69%).
m.p.=117° C.

EXAMPLE 83

5-Chloro-1-[(2-methyl-6-benzothiazolyl)sulfonyl]-1H-pyrrolo[3,2-b]pyridine-2-butanoic acid By working in a manner similar to that of Example 2, starting with the ester obtained according to Example 82, the expected compound is obtained in the form of a yellow solid (yield=99%).
m.p.=184° C.

EXAMPLE 84

5-Chloro-1-[(2-methyl-7-benzothiazolyl)sulfonyl]-1H-pyrrolo[3,2-b]pyridine-2-butanoic acid, methyl ester By working in a manner similar to that of Preparation VI, starting with the compound according to Preparation V and 2-methyl-7-benzothiazolesulfonyl chloride, the expected compound is obtained in the form of a yellow solid (yield=48%).
m.p.=138° C.

EXAMPLE 85

5-Chloro-1-[(2-methyl-7-benzothiazolyl)sulfonyl]-1H-pyrrolo[3,2-b]pyridine-2-butanoic acid By working in a manner similar to that of Example 2, starting with the ester obtained according to Example 84, the expected compound is obtained in the form of a beige-colored solid (yield=90%).
m.p.=225° C.

EXAMPLE 86

5-Chloro-1-[(2,3-dihydro-5-benzofuryl)sulfonyl]-1H-pyrrolo[3,2-b]pyridine-2-butanoic acid, methyl ester By working in a manner similar to that of Example 76, starting with 2,3-dihydro-5-benzofuransulfonyl chloride, the expected compound is obtained in the form of a yellow solid (yield=82%).
m.p.=201° C.

EXAMPLE 87

5-chloro-1-[(2,3-dihydro-5-benzofuryl)sulfonyl]-1H-pyrrolo[3,2-b]pyridine-2-butanoic acid By working in a manner similar to that of Example 2, starting with the ester obtained according to Example 86, the expected compound is obtained in the form of a white solid (yield=98%).
m.p.=225° C.

EXAMPLE 88

5-Chloro-1-[(3,5-dichlorophenyl)sulfonyl]-1H-pyrrolo[3,2-b]pyridine-2-butanoic acid, methyl ester By working in a manner similar to that of Example 76, starting with 3,5-dichlorobenzenesulfonyl chloride, the expected compound is obtained in the form of a white solid (yield=66%).
m.p.=112-114° C.

EXAMPLE 89

5-Chloro-1-[(3,5-dichlorophenyl)sulfonyl]-1H-pyrrolo[3,2-b]pyridine-2-butanoic acid By working in a manner similar to that of Example 2, starting with the ester obtained according to Example 88, the expected compound is obtained in the form of a white solid (yield=28%).
m.p.=164-165° C.

EXAMPLE 90

1-[(2-Acetylamino-6-benzothiazolyl)sulfonyl]-5-chloro-1H-pyrrolo[3,2-b]pyridine-2-butanoic acid, methyl ester By working in a manner similar to that of Example 76, starting with 2-acetylamino-6-benzothiazolesulfonyl chloride, the expected compound is obtained in the form of a yellow solid (yield=35%).
m.p.=274° C.

EXAMPLE 91

1-[(2-Acetylamino-6-benzothiazolyl)sulfonyl]-5-chloro-1H-pyrrolo[3,2-b]pyridine-2-butanoic acid By working in a manner similar to that of Example 2, starting with the ester obtained according to Example 90, the expected compound is obtained in the form of a white solid (yield=87%).
m.p.=270° C.

EXAMPLE 92

1-[(2-Amino-6-benzoxazolyl)sulfonyl]-5-chloro-1H-pyrrolo[3,2-b]pyridine-2-butanoic acid, methyl ester By working in a manner similar to that of Example 76, starting with 2-amino-6-benzoxazolesulfonyl chloride, the expected compound is obtained in the form of a white solid (yield=35%).
m.p.=241° C.

EXAMPLE 93

1-[(2-Amino-6-benzoxazolyl)sulfonyl]-5-chloro-1H-pyrrolo[3,2-b]pyridine-2-butanoic acid By working in a manner similar to that of Example 2, starting with the ester obtained according to Example 92, the expected compound is obtained in the form of a white solid (yield=96%).
m.p.=273° C.

EXAMPLE 94

5-Chloro-1-[(2-fluorophenyl)sulfonyl]-1H-pyrrolo[3,2-b]pyridine-2-butanoic acid, methyl ester By working in a manner similar to that of Example 76, starting with 2-fluorobenzenesulfonyl chloride, the expected compound is obtained in the form of a brown solid (yield=87%).
m.p.=83° C.

EXAMPLE 95

5-Chloro-1-[(2-fluorophenyl)sulfonyl]-1H-pyrrolo[3,2-b]pyridine-2-butanoic acid

By working in a manner similar to that of Example 2, starting with the ester obtained according to Example 94, the expected compound is obtained in the form of a beige-colored solid (yield=92%).
m.p.=176° C.

EXAMPLE 96

5-Chloro-1-[[2-(trifluoromethyl)phenyl]sulfonyl]-1H-pyrrolo[3,2-b]pyridine-2-butanoic acid, methyl ester By working in a manner similar to that of Preparation VI, starting with the compound according to Preparation V and 2-(trifluoromethyl)benzenesulfonyl chloride, the expected compound is obtained in the form of a yellow solid (yield=39%).
m.p.=127° C.

EXAMPLE 97

5-Chloro-1-[[2-(trifluoromethyl)phenyl]sulfonyl]-1H-pyrrolo[3,2-b]pyridine-2-butanoic acid By working in a manner similar to that of Example 2, starting with the ester obtained according to Example 96, the expected compound is obtained in the form of a yellow solid (yield=89%).
m.p.=171° C.

EXAMPLE 98

1-([1,1'-Biphenyl]-3-ylsulfonyl)-5-chloro-1H-pyrrolo[3,2-b]pyridine-2-butanoic acid, methyl ester By working in a manner similar to that of Preparation VI, starting with the compound according to Preparation V and [1,1'-biphenyl]-3-sulfonyl chloride, the expected compound is obtained in the form of a white solid (yield=68%).
$^1$H NMR (300 MHz, DMSO-$d_6$) δ: 8.49 (d, 1H); 8.03 (m, 2H); 7.78 (d, 1H); 7.66 (m, 3H); 7.47 (m, 3H); 7.39 (d, 1H); 6.79 (s, 1H); 3.55 (s, 3H); 3.11 (t, 2H); 2.44 (t, 2H); 2.01 (m, 2H).

EXAMPLE 99

1-([1,1'-Biphenyl]-3-ylsulfonyl)-5-chloro-1H-pyrrolo[3,2-b]pyridine-2-butanoic acid By working in a manner similar to that of Example 2, starting with the ester obtained according to Example 98, the expected compound is obtained in the form of a white solid (yield=23%).
m.p.=147-149° C.

EXAMPLE 100

5-Chloro-1-[(4-fluorophenyl)sulfonyl]-1H-pyrrolo[3,2-b]pyridine-2-butanoic acid, methyl ester By working in a manner similar to that of Preparation VI, starting with the compound according to Preparation V and 4-fluorobenzenesulfonyl chloride, the expected compound is obtained in the form of a yellow solid (yield=29%).
m.p.=119° C.

EXAMPLE 101

5-Chloro-1-[(4-fluorophenyl)sulfonyl]-1H-pyrrolo[3,2-b]pyridine-2-butanoic acid

By working in a manner similar to that of Example 2, starting with the ester obtained according to Example 100, the expected compound is obtained in the form of a beige-colored solid (yield=66%).
m.p.=180° C.

EXAMPLE 102

5-Chloro-1-[(3-fluorophenyl)sulfonyl]-1H-pyrrolo[3,2-b]pyridine-2-butanoic acid, methyl ester By working in a manner similar to that of Example 76, starting with 3-fluorobenzenesulfonyl chloride, the expected compound is obtained in the form of a brown solid (yield=76%).
m.p.=104° C.

EXAMPLE 103

5-Chloro-1-[(3-fluorophenyl)sulfonyl]-1H-pyrrolo[3,2-b]pyridine-2-butanoic acid

By working in a manner similar to that of Example 2, starting with the ester obtained according to Example 102, the expected compound is obtained in the form of a beige-colored solid (yield=75%).
m.p.=163° C.

EXAMPLE 104

1-[(1-Acetyl-2,3-dihydro-1H-indol-5-yl)sulfonyl]-5-chloro-1H-pyrrolo[3,2-b]pyridine-2-butanoic acid, methyl ester By working in a manner similar to that of Example 76, starting with 1-acetyl-2,3-dihydro-1H-indole-5-sulfonyl chloride, the expected compound is obtained in the form of a beige-colored solid (yield=91%).
m.p.=123° C.

EXAMPLE 105

1-[(1-Acetyl-2,3-dihydro-1H-indol-5-yl)sulfonyl]-5-chloro-1H-pyrrolo[3,2-b]pyridine-2-butanoic acid By working in a manner similar to that of Example 2, starting with the ester obtained according to Example 104, the expected compound is obtained in the form of a beige-colored solid (yield=54%).
m.p.=226° C.

EXAMPLE 106

5-Chloro-1-[(6-chloroimidazo[2,1-b]thiazol-5-yl)
sulfonyl]-1H-pyrrolo-[3,2-b]pyridine-2-butanoic
acid, methyl ester By working in a manner similar to that of Example 76, starting with 6-chloroimidazo[2,1-b]thiazole-5-sulfonyl chloride, the expected compound is obtained in the form of a colorless oil (yield=70%).

$^1$H NMR (250 MHz, DMSO-$d_6$) δ: 8.55 (s, 1H); 8.43 (d, 1H); 7.95 (m, 5H); 7.39 (d, 1H); 6.78 (s, 1H); 3.58 (s, 3H); 3.07 (t, 2H); 2.44 (t, 2H); 1.97 (m, 2H).

EXAMPLE 107

5-Chloro-1-[(6-chloroimidazo[2,1-b]thiazol-5-yl)
sulfonyl]-1H-pyrrolo-[3,2-b]pyridine-2-butanoic acid By working in a manner similar to that of Example 2, starting with the ester obtained according to Example 106, the expected compound is obtained in the form of a white solid (yield=99%).

m.p.=186° C.

EXAMPLE 108

5-Chloro-1-[[4-(1H-pyrazol-1-yl)phenyl]sulfonyl]-
1H-pyrrolo[3,2-b]pyridine-2-butanoic acid, methyl
ester By working in a manner similar to that of Preparation VI, starting with the compound according to Preparation V and 4-(1H-pyrazol-1-yl)benzenesulfonyl chloride, the expected compound is obtained in the form of a white solid (yield=10%).

m.p.=122-124° C.

EXAMPLE 109

5-Chloro-1-[[4-(1H-pyrazol-1-yl)phenyl]sulfonyl]-
1H-pyrrolo[3,2-b]pyridine-2-butanoic acid By working in a manner similar to that of Example 2, starting with the ester obtained according to Example 108, the expected compound is obtained in the form of a white solid (yield=58%).

m.p.=196-207° C.

EXAMPLE 110

5-Chloro-1-[[3-(trifluoromethyl)phenyl]sulfonyl]-
1H-pyrrolo[3,2-b]pyridine-2-butanoic acid, methyl
ester By working in a manner similar to that of Preparation VI, starting with the compound according to Preparation V and 3-(trifluoromethyl)benzenesulfonyl chloride, the expected compound is obtained in the form of a yellow solid (yield=11%).

m.p.=97° C.

EXAMPLE 111

5-Chloro-1-[[3-(trifluoromethyl)phenyl]sulfonyl]-
1H-pyrrolo[3,2-b]pyridine-2-butanoic acid By working in a manner similar to that of Example 2, starting with the ester obtained according to Example 110, the expected compound is obtained in the form of a yellow solid (yield=41%).

m.p.=188° C.

EXAMPLE 112

5-Chloro-1-[[4-(trifluoromethyl)phenyl]sulfonyl]-
1H-pyrrolo[3,2-b]pyridine-2-butanoic acid, methyl
ester By working in a manner similar to that of Preparation VI, starting with the compound according to Preparation V and 4-(trifluoromethyl)benzenesulfonyl chloride, the expected compound is obtained in the form of a beige-colored solid (yield=27%).

m.p.=99° C.

EXAMPLE 113

5-chloro-1-[[4-(trifluoromethyl)phenyl]sulfonyl]-
1H-pyrrolo[3,2-b]pyridine-2-butanoic acid By working in a manner similar to that of Example 2, starting with the ester obtained according to Example 112, the expected compound is obtained in the form of a white solid (yield=27%).

m.p.=185° C.

EXAMPLE 114

5-Chloro-1-[[4-(5-oxazolyl)phenyl]sulfonyl]-1H-
pyrrolo[3,2-b]pyridine-2-butanoic acid, methyl ester By working in a manner similar to that of Example 76, starting with 4-(5-oxazolyl)benzenesulfonyl chloride, the expected compound is obtained in the form of a colorless oil (yield=50%).

$^1$H NMR (250 MHz, DMSO-$d_6$) δ: 8.55 (s, 1H); 8.43 (d, 1H); 7.95 (m, 5H); 7.39 (d, 1H); 6.78 (s, 1H); 3.58 (s, 3H); 3.07 (t, 2H); 2.44 (t, 2H); 1.97 (m, 2H).

EXAMPLE 115

5-Chloro-1-[[4-(5-oxazolyl)phenyl]sulfonyl]-1H-
pyrrolo[3,2-b]pyridine-2-butanoic acid By working in a manner similar to that of Example 2, starting with the ester obtained according to Example 114, the expected compound is obtained in the form of a white solid (yield=27%).

m.p.=169-176° C.

EXAMPLE 116

1-[[3,5-Bis(trifluoromethyl)phenyl]sulfonyl]-5-
chloro-1H-pyrrolo[3,2-b]pyridine-2-butanoic acid,
methyl ester By working in a manner similar to that of Example 76, starting with 3,5-bis(trifluoromethyl)benzenesulfonyl chloride, the expected compound is obtained in the form of a white solid (yield=62%).

m.p.=134-144° C.

EXAMPLE 117

1-[[3,5-Bis(trifluoromethyl)phenyl]sulfonyl]-5-chloro-1H-pyrrolo[3,2-b]pyridine-2-butanoic acid By working in a manner similar to that of Example 2, starting with the ester obtained according to Example 116, the expected compound is obtained in the form of a beige-colored solid (yield=6%).
m.p.=155-164° C.

EXAMPLE 118

5-Chloro-1-[(4-chloro-3-methylphenyl)sulfonyl]-1H-pyrrolo[3,2-b]pyridine-2-butanoic acid, methyl ester By working in a manner similar to that of Example 76, starting with 4-chloro-3-methylbenzenesulfonyl chloride, the expected compound is obtained in the form of a white solid (yield=78%).
m.p.=111-114° C.

EXAMPLE 119

5-Chloro-1-[(4-chloro-3-methylphenyl)sulfonyl]-1H-pyrrolo[3,2-b]pyridine-2-butanoic acid By working in a manner similar to that of Example 2, starting with the ester obtained according to Example 118, the expected compound is obtained in the form of a white solid (yield=42%).
m.p.=175-183° C.

EXAMPLE 120

1-([1,1'-Biphenyl]-4-ylsulfonyl)-5-chloro-1H-pyrrolo[3,2-b]pyridine-2-butanoic acid, methyl ester By working in a manner similar to that of Example 76, starting with [1,1'-biphenyl]-4-sulfonyl chloride, the expected compound is obtained in the form of a white solid (yield=85%).
m.p.=122-124° C.

EXAMPLE 121

1-([1,1'-Biphenyl]-4-ylsulfonyl)-5-chloro-1H-pyrrolo[3,2-b]pyridine-2-butanoic acid By working in a manner similar to that of Example 2, starting with the ester obtained according to Example 120, the expected compound is obtained in the form of a white solid (yield=55%).
m.p.=186-190° C.

EXAMPLE 122

5-Chloro-1-[(3,4-difluorophenyl)sulfonyl]-1H-pyrrolo[3,2-b]pyridine-2-butanoic acid, methyl ester By working in a manner similar to that of Example 76, starting with 3,4-difluorobenzenesulfonyl chloride, the expected compound is obtained in the form of a white solid (yield=61%).
m.p.=96-98° C.

EXAMPLE 123

5-Chloro-1-[(3,4-difluorophenyl)sulfonyl]-1H-pyrrolo[3,2-b]pyridine-2-butanoic acid By working in a manner similar to that of Example 2, starting with the ester obtained according to Example 122, the expected compound is obtained in the form of a beige-colored solid (yield=59%).
m.p.=180-190° C.

EXAMPLE 124

5-Chloro-1-[3-(trifluoromethoxy)phenylsulfonyl]-1H-pyrrolo[3,2-b]pyridine-2-butanoic acid, methyl ester By working in a manner similar to that of Example 76, starting with 3-(trifluoromethoxy)benzenesulfonyl chloride, the expected compound is obtained in the form of a brown oil (yield=84%).
$^1$H NMR (300 MHz, DMSO-$d_6$) δ: 8.44 (d, 1H); 7.89 (m, 2H); 7.77 (m, 2H); 7.39 (d, 1H); 6.80 (s, 1H); 3.58 (s, 3H); 3.06 (t, 2H); 2.44 (t, 2H); 1.96 (quint., 2H).

EXAMPLE 125

5-Chloro-1-[3-(trifluoromethoxy)phenylsulfonyl]-1H-pyrrolo[3,2-b]pyridine-2-butanoic acid By working in a manner similar to that of Example 2, starting with the ester obtained according to Example 124, the expected compound is obtained in the form of a beige-colored solid (yield=37%).
m.p.=176° C.

EXAMPLE 126

1-(1,2,3-Benzothiadiazol-5-ylsulfonyl)-5-chloro-1H-pyrrolo[3,2-b]pyridine-2-butanoic acid, methyl ester By working in a manner similar to that of Preparation VI, starting with the compound according to Preparation V and 1,2,3-benzothiadiazole-5-sulfonyl chloride, the expected compound is obtained in the form of a beige-colored solid (yield=9%).
m.p.=219° C.

EXAMPLE 127

1-(1,2,3-Benzothiadiazol-5-ylsulfonyl)-5-chloro-1H-pyrrolo[3,2-b]pyridine-2-butanoic acid By working in a manner similar to that of Example 2, starting with the ester obtained according to Example 126, the expected compound is obtained in the form of a white solid (yield=58%).
m.p.=227° C.

EXAMPLE 128

5-Chloro-1-[4-(trifluoromethoxy)phenylsulfonyl]-1H-pyrrolo[3,2-b]pyridine-2-butanoic acid, methyl ester By working in a manner similar to that of Example 76, starting with 4-(trifluoromethoxy)benzenesulfonyl chloride, the expected compound is obtained in the form of a white solid (yield=52%).
m.p.=109° C.

EXAMPLE 129

5-Chloro-1-[4-(trifluoromethoxy)phenylsulfonyl]-1H-pyrrolo[3,2-b]pyridine-2-butanoic acid By working in a manner similar to that of Example 2, starting with the ester obtained according to Example 128, the expected compound is obtained in the form of a white solid (yield=88%).
m.p.=168° C.

EXAMPLE 130

5-Chloro-1-[(3-chlorophenyl)sulfonyl]-1H-pyrrolo[3,2-b]pyridine-2-butanoic acid, methyl ester By working in a manner similar to that of Example 76, starting with 3-chlorobenzenesulfonyl chloride, the expected compound is obtained in the form of a white solid (yield=14%).
m.p.=107° C.

EXAMPLE 131

5-Chloro-1-[(3-chlorophenyl)sulfonyl]-1H-pyrrolo[3,2-b]pyridine-2-butanoic acid

By working in a manner similar to that of Example 2, starting with the ester obtained according to Example 130, the expected compound is obtained in the form of a beige-colored solid (yield=83%).
m.p.=174° C.

EXAMPLE 132

5-Chloro-1-[(4-chlorophenyl)sulfonyl]-1H-pyrrolo[3,2-b]pyridine-2-butanoic acid, methyl ester By working in a manner similar to that of Example 76, starting with 4-chlorobenzenesulfonyl chloride, the expected compound is obtained in the form of a beige-colored solid (yield=35%).
m.p.=108° C.

EXAMPLE 133

5-Chloro-1-[(4-chlorophenyl)sulfonyl]-1H-pyrrolo[3,2-b]pyridine-2-butanoic acid

By working in a manner similar to that of Example 2, starting with the ester obtained according to Example 132, the expected compound is obtained in the form of a beige-colored solid (yield=81%).
m.p.=174° C.

EXAMPLE 134

5-Chloro-1-[(3-methoxyphenyl)sulfonyl]-1H-pyrrolo[3,2-b]pyridine-2-butanoic acid, methyl ester By working in a manner similar to that of Example 76, starting with 3-methoxybenzenesulfonyl chloride, the expected compound is obtained in the form of a yellow solid (yield=45%).
m.p.=90° C.

EXAMPLE 135

5-Chloro-1-[(3-methoxyphenyl)sulfonyl]-1H-pyrrolo[3,2-b]pyridine-2-butanoic acid By working in a manner similar to that of Example 2, starting with the ester obtained according to Example 134, the expected compound is obtained in the form of a beige-colored solid (yield=94%).
m.p.=139° C.

EXAMPLE 136

5-Chloro-1-[(4-methoxyphenyl)sulfonyl]-1H-pyrrolo[3,2-b]pyridine-2-butanoic acid, methyl ester By working in a manner similar to that of Example 76, starting with 4-methoxybenzenesulfonyl chloride, the expected compound is obtained in the form of a beige-colored solid (yield=66%).
m.p.=96° C.

EXAMPLE 137

5-Chloro-1-[(4-methoxyphenyl)sulfonyl]-1H-pyrrolo[3,2-b]pyridine-2-butanoic acid By working in a manner similar to that of Example 2, starting with the ester obtained according to Example 136, the expected compound is obtained in the form of a white solid (yield=78%).
m.p.=189° C.

EXAMPLE 138

5-Chloro-1-[(4-methylphenyl)sulfonyl]-1H-pyrrolo[3,2-b]pyridine-2-butanoic acid, methyl ester By working in a manner similar to that of Example 76, starting with 4-methylbenzenesulfonyl chloride, the expected compound is obtained in the form of a gray solid (yield=37%).
m.p.=106° C.

EXAMPLE 139

5-Chloro-1-[(4-methylphenyl)sulfonyl]-1H-pyrrolo[3,2-b]pyridine-2-butanoic acid

By working in a manner similar to that of Example 2, starting with the ester obtained according to Example 138, the expected compound is obtained in the form of a white solid (yield=87%).
m.p.=172° C.

EXAMPLE 140

5-Chloro-1-[[4-(1-methylethyl)phenyl]sulfonyl]-1H-pyrrolo[3,2-b]pyridine-2-butanoic acid, methyl ester By working in a manner similar to that of Example 76, starting with 4-(1-methylethyl)benzenesulfonyl chloride, the expected compound is obtained in the form of a white solid (yield=51%).
m.p.=75° C.

EXAMPLE 141

5-Chloro-1-[[4-(1-methylethyl)phenyl]sulfonyl]-1H-pyrrolo[3,2-b]pyridine-2-butanoic acid By working in a manner similar to that of Example 2, starting with the ester obtained according to Example 140, the expected compound is obtained in the form of a white solid (yield=88%).
m.p.=155° C.

EXAMPLE 142

5-Chloro-1-[[3-(2-methyl-4-pyrimidinyl)phenyl]sulfonyl]-1H-pyrrolo-[3,2-b]pyridine-2-butanoic acid, methyl ester By working in a manner similar to that of Example 76, starting with 3-(2-methyl-4-pyrimidinyl)benzenesulfonyl chloride, the expected compound is obtained in the form of a yellow solid (yield=78%).
m.p.=140-144° C.

EXAMPLE 143

5-Chloro-1-[[3-(2-methyl-4-pyrimidinyl)phenyl]sulfonyl]-1H-pyrrolo-[3,2-b]pyridine-2-butanoic acid By working in a manner similar to that of Example 2, starting with the ester obtained according to Example 142, the expected compound is obtained in the form of a white solid (yield=38%).
m.p.=178-188° C.

EXAMPLE 144

1-(1,2-Benzisoxazol-5-ylsulfonyl)-5-chloro-1H-pyrrolo[3,2-b]pyridine-2-butanoic acid, methyl ester By working in a manner similar to that of Preparation VI, starting with the compound according to Preparation V and 1,2-benzisoxazole-5-sulfonyl chloride, the expected compound is obtained in the form of a beige-colored solid (yield=7%).
$^1$H NMR (250 MHz, DMSO-$d_6$) δ: 8.42 (d, 1H); 8.32 (d, 1H); 7.98 (dd, 1H); 7.36 (d, 1H); 7.10 (d, 1H); 6.75 (s, 1H); 3.58 (s, 3H); 3.05 (t, 2H); 2.45 (t, 2H); 1.95 (quint., 2H).

EXAMPLE 145

1-(1,2-Benzisoxazol-5-ylsulfonyl)-5-chloro-1H-pyrrolo[3,2-b]pyridine-2-butanoic acid By working in a manner similar to that of Example 2, starting with the ester obtained according to Example 144, the expected compound is obtained in the form of a yellow solid (yield=33%).
m.p.=226° C.

EXAMPLE 146

5-Chloro-1-[2-(trifluoromethoxy)phenylsulfonyl]-1H-pyrrolo[3,2-b]pyridine-2-butanoic acid, methyl ester By working in a manner similar to that of Preparation VI, starting with the compound according to Preparation V and 2-(trifluoromethoxy)benzenesulfonyl chloride, the expected compound is obtained in the form of a pasty white solid.

EXAMPLE 147

5-Chloro-1-[2-(trifluoromethoxy)phenylsulfonyl]-1H-pyrrolo[3,2-b]pyridine-2-butanoic acid By working in a manner similar to that of Example 2, starting with the ester obtained according to Example 146, the expected compound is obtained in the form of a white solid (yield=50%).
m.p.=138° C.

EXAMPLE 148

5-Chloro-1-[(3,5-difluorophenyl)sulfonyl]-1H-pyrrolo[3,2-b]pyridine-2-butanoic acid, methyl ester By working in a manner similar to that of Example 76, starting with 3,5-difluorobenzenesulfonyl chloride, the expected compound is obtained in the form of a beige-colored solid (yield=83%).
m.p.=90° C.

EXAMPLE 149

5-Chloro-1-[(3,4-difluorophenyl)sulfonyl]-1H-pyrrolo[3,2-b]pyridine-2-butanoic acid By working in a manner similar to that of Example 2, starting with the ester obtained according to Example 148, the expected compound is obtained in the form of a gray solid (yield=24%).
$^1$H NMR (300 MHz, DMSO-$d_6$) δ: 12.11 (s, 1H); 8.44 (d, 1H); 7.75 (m, 3H); 7.38 (d, 1H); 6.80 (s, 1H); 3.08 (t, 2H); 2.37 (m, 2H); 1.94 (m, 2H).

EXAMPLE 150

5-Chloro-1-[(2,5-dichlorophenyl)sulfonyl]-1H-pyrrolo[3,2-b]pyridine-2-butanoic acid, methyl ester By working in a manner similar to that of Example 76, starting with 2,5-dichlorobenzenesulfonyl chloride, the expected compound is obtained in the form of a beige-colored solid (yield=65%).
m.p.=95-105° C.

EXAMPLE 151

5-Chloro-1-[(2,5-dichlorophenyl)sulfonyl]-1H-pyrrolo[3,2-b]pyridine-2-butanoic acid By working in a manner similar to that of Example 2, starting with the ester obtained according to Example 150, the expected compound is obtained in the form of a gray solid (yield=43%).
m.p.=86-89° C.

EXAMPLE 152

5-Chloro-1-[(2-chlorophenyl)sulfonyl]-1H-pyrrolo[3,2-b]pyridine-2-butanoic acid, methyl ester By working in a manner similar to that of Example 76, starting with 2-chlorobenzenesulfonyl chloride, the expected compound is obtained, which is reacted directly to obtain the acid.

EXAMPLE 153

5-Chloro-1-[(2-chlorophenyl)sulfonyl]-1H-pyrrolo[3,2-b]pyridine-2-butanoic acid

By working in a manner similar to that of Example 2, starting with the ester obtained according to Example 152, the expected compound is obtained in the form of a beige-colored solid (yield=48%).

m.p.=139° C.

EXAMPLE 154

5-Chloro-1-[(2-methylphenyl)sulfonyl]-1H-pyrrolo[3,2-b]pyridine-2-butanoic acid, methyl ester By working in a manner similar to that of Example 76, starting with 2-methylbenzenesulfonyl chloride, the expected compound is obtained, which is reacted directly to obtain the corresponding acid.

EXAMPLE 155

5-Chloro-1-[(2-methylphenyl)sulfonyl]-1H-pyrrolo[3,2-b]pyridine-2-butanoic acid

By working in a manner similar to that of Example 2, starting with the ester obtained according to Example 154, the expected compound is obtained in the form of a white solid (yield=66%).

m.p.=161° C.

EXAMPLE 156

5-Chloro-1-[(3-methylphenyl)sulfonyl]-1H-pyrrolo[3,2-b]pyridine-2-butanoic acid, methyl ester By working in a manner similar to that of Example 76, starting with 3-methylbenzenesulfonyl chloride, the expected compound is obtained, which is reacted directly to obtain the corresponding acid.

EXAMPLE 157

5-Chloro-1-[(3-methylphenyl)sulfonyl]-1H-pyrrolo[3,2-b]pyridine-2-butanoic acid

By working in a manner similar to that of Example 2, starting with the ester obtained according to Example 156, the expected compound is obtained in the form of a white solid (yield=38%).

m.p.=165° C.

EXAMPLE 158

5-Chloro-1-[(2,6-difluorophenyl)sulfonyl]-1H-pyrrolo[3,2-b]pyridine-2-butanoic acid, methyl ester By working in a manner similar to that of Example 76, starting with 2,6-difluorobenzenesulfonyl chloride, the expected compound is obtained in the form of a white solid (yield=76%).

m.p.=107-109° C.

EXAMPLE 159

5-Chloro-1-[(2,6-difluorophenyl)sulfonyl]-1H-pyrrolo[3,2-b]pyridine-2-butanoic acid By working in a manner similar to that of Example 2, starting with the ester obtained according to Example 158, the expected compound is obtained in the form of a white solid (yield=38%).

m.p.=192-195° C.

EXAMPLE 160

5-Chloro-1-[(2,4,6-trifluorophenyl)sulfonyl]-1H-pyrrolo[3,2-b]pyridine-2-butanoic acid, methyl ester By working in a manner similar to that of Example 76, starting with 2,4,6-trifluorobenzenesulfonyl chloride, the expected compound is obtained in the form of a white solid (yield=71%).

$^1$H NMR (250 MHz, DMSO-$d_6$) δ: 8.20 (d, 1H); 7.56 (m, 2H); 7.41 (d, 1H); 6.84 (s, 1H); 3.57 (s, 3H); 2.94 (t, 2H); 2.41 (t, 2H); 1.94 (quint., 2H).

EXAMPLE 161

5-Chloro-1-[(2,4,6-trifluorophenyl)sulfonyl]-1H-pyrrolo[3,2-b]pyridine-2-butanoic acid By working in a manner similar to that of Example 2, starting with the ester obtained according to Example 160, the expected compound is obtained in the form of a beige-colored solid (yield=27%).

m.p.=135-150° C.

EXAMPLE 162

5-Chloro-1-[(2,5-dimethylphenyl)sulfonyl]-1H-pyrrolo[3,2-b]pyridine-2-butanoic acid, methyl ester By working in a manner similar to that of Example 76, starting with 2,5-dimethylbenzenesulfonyl chloride, the expected compound is obtained in the form of a white solid (yield=87%).

m.p.=92-103° C.

EXAMPLE 163

5-Chloro-1-[(2,5-dimethylphenyl)sulfonyl]-1H-pyrrolo[3,2-b]pyridine-2-butanoic acid By working in a manner similar to that of Example 2, starting with the ester obtained according to Example 162, the expected compound is obtained in the form of a yellow solid (yield=72%).

m.p.=106-117° C.

EXAMPLE 164

5-Chloro-1-[(3,5-dimethoxyphenyl)sulfonyl]-1H-pyrrolo[3,2-b]pyridine-2-butanoic acid, methyl ester By working in a manner similar to that of Example 76, starting with 3,5-dimethoxybenzenesulfonyl chloride, the expected compound is obtained in the form of a beige-colored solid (yield=75%).
m.p.=109-111° C.

EXAMPLE 165

5-Chloro-1-[(3,5-dimethoxyphenyl)sulfonyl]-1H-pyrrolo[3,2-b]pyridine-2-butanoic acid By working in a manner similar to that of Example 2, starting with the ester obtained according to Example 164, the expected compound is obtained in the form of a white solid (yield=27%).
m.p.=136-138° C.

EXAMPLE 166

5-Chloro-1-[4-(1-methylethoxy)phenylsulfonyl]-1H-pyrrolo[3,2-b]pyridine-2-butanoic acid, methyl ester By working in a manner similar to that of Example 76, starting with 4-(1-methylethoxy)benzenesulfonyl chloride, the expected compound is obtained in the form of a colorless oil (yield=88%).
$^1$H NMR (250 MHz, DMSO-$d_6$) δ: 8.41 (d, 1H); 7.77 (d, 2H); 7.38 (d, 1H); 7.05 (d, 2H); 6.73 (s, 1H); 4.70 (sept., 1H); 3.59 (s, 3H); 3.04 (t, 2H); 2.43 (t, 2H); 1.95 (quint., 2H); 1.24 (d, 6H).

EXAMPLE 167

5-Chloro-1-[4-(1-methylethoxy)phenylsulfonyl]-1H-pyrrolo[3,2-b]pyridine-2-butanoic acid By working in a manner similar to that of Example 2, starting with the ester obtained according to Example 166, the expected compound is obtained in the form of a white solid (yield=97%).
m.p.=171° C.

EXAMPLE 168

5-Chloro-1-[(2-methoxyphenyl)sulfonyl]-1H-pyrrolo[3,2-b]pyridine-2-butanoic acid, methyl ester By working in a manner similar to that of Preparation VI, starting with the compound according to Preparation V and 2-methoxybenzenesulfonyl chloride, the expected compound is obtained in the form of a beige-colored solid (yield=41%).
m.p.=115° C.

EXAMPLE 169

5-Chloro-1-[(2-methoxyphenyl)sulfonyl]-1H-pyrrolo[3,2-b]pyridine-2-butanoic acid By working in a manner similar to that of Example 2, starting with the ester obtained according to Example 168, the expected compound is obtained in the form of a white solid (yield=89%).
m.p.=197° C.

EXAMPLE 170

5-Chloro-1-[(2-chloro-3-methylphenyl)sulfonyl]-1H-pyrrolo[3,2-b]pyridine-2-butanoic acid, methyl ester By working in a manner similar to that of Example 76, starting with 2-chloro-3-methylbenzenesulfonyl chloride, the expected compound is obtained in the form of a green oil (yield=57%).
$^1$H NMR (250 MHz, DMSO-$d_6$) δ: 8.18 (d, 1H); 7.87 (d, 1H); 7.79 (d, 1H); 7.55 (t, 1H); 7.34 (d, 1H); 6.81 (s, 1H); 3.55 (s, 3H); 2.86 (t, 2H); 2.35 (m, 5H); 1.85 (quint., 2H).

EXAMPLE 171

5-Chloro-1-[(2-chloro-3-methylphenyl)sulfonyl]-1H-pyrrolo[3,2-b]pyridine-2-butanoic acid By working in a manner similar to that of Example 2, starting with the ester obtained according to Example 170, the expected compound is obtained in the form of a white solid (yield=16%).
m.p.=171-174° C.

EXAMPLE 172

5-Chloro-1-[(2,4-difluorophenyl)sulfonyl]-1H-pyrrolo[3,2-b]pyridine-2-butanoic acid, methyl ester By working in a manner similar to that of Example 76, starting with 2,4-difluorobenzenesulfonyl chloride, the expected compound is obtained in the form of a yellow oil (yield=82%).
$^1$H NMR (250 MHz, DMSO-$d_6$) δ: 8.26 (d, 1H); 8.17 (m, 1H); 7.59 (m, 1H); 7.40 (m, 2H); 6.81 (s, 1H); 3.57 (s, 3H); 2.94 (t, 2H); 2.40 (t, 2H); 1.89 (quint., 2H).

EXAMPLE 173

5-Chloro-1-[(2,4-difluorophenyl)sulfonyl]-1H-pyrrolo[3,2-b]pyridine-2-butanoic acid By working in a manner similar to that of Example 2, starting with the ester obtained according to Example 172, the expected compound is obtained in the form of a white solid (yield=8%).
m.p.=172-177° C.

EXAMPLE 174

5-Chloro-1-[(2-chloro-4-methoxyphenyl)sulfonyl]-1H-pyrrolo[3,2-b]pyridine-2-butanoic acid, methyl ester By working in a manner similar to that of Example 76, starting with 2-chloro-4-methoxybenzenesulfonyl chloride, the expected compound is obtained in the form of a white solid (yield=75%).
m.p.=116-118° C.

EXAMPLE 175

5-Chloro-1-[(2-chloro-4-methoxyphenyl)sulfonyl]-1H-pyrrolo[3,2-b]pyridine-2-butanoic acid By working in a manner similar to that of Example 2, starting with the ester obtained according to Example 174, the expected compound is obtained in the form of a white solid (yield=78%).

m.p.=154-156° C.

EXAMPLE 176

5-Chloro-1-[[4-(4-thiazolyl)phenyl]sulfonyl]-1H-pyrrolo[3,2-b]pyridine-2-butanoic acid, methyl ester By working in a manner similar to that of Example 76, starting with 4-(4-thiazolyl)benzenesulfonyl chloride, the expected compound is obtained in the form of a white paste (yield=78%).

$^1$H NMR (300 MHz, DMSO-$d_6$) δ: 9.23 (d, 1H); 8.43 (m, 2H); 8.18 (d, 2H); 7.95 (d, 2H); 7.40 (d, 1H); 6.77 (s, 1H); 3.58 (s, 3H); 3.09 (t, 2H); 2.45 (t, 2H); 1.98 (quint., 2H).

EXAMPLE 177

5-Chloro-1-[[4-(4-thiazolyl)phenyl]sulfonyl]-1H-pyrrolo[3,2-b]pyridine-2-butanoic acid By working in a manner similar to that of Example 2, starting with the ester obtained according to Example 176, the expected compound is obtained in the form of a white solid (yield=62%).

m.p.=211-217° C.

EXAMPLE 178

5-Chloro-1-[[4-(1,1-dimethylethyl)phenyl]sulfonyl]-1H-pyrrolo[3,2-b]pyridine-2-butanoic acid, methyl ester By working in a manner similar to that of Example 76, starting with 4-(1,1-dimethylethyl)benzenesulfonyl chloride, the expected compound is obtained in the form of a white solid (yield=98%).

m.p.=107° C.

EXAMPLE 179

5-Chloro-1-[[4-(1,1-dimethylethyl)phenyl]sulfonyl]-1H-pyrrolo[3,2-b]pyridine-2-butanoic acid By working in a manner similar to that of Example 2, starting with the ester obtained according to Example 178, the expected compound is obtained in the form of a white solid (yield=89%).

m.p.=168° C.

EXAMPLE 180

5-Chloro-1-[(2,3-dihydro-1,4-benzodioxin-6-yl)sulfonyl]-1H-pyrrolo-[3,2-b]pyridine-2-butanoic acid, methyl ester By working in a manner similar to that of Preparation VI, starting with the compound according to Preparation V and 2,3-dihydro-1,4-benzodioxine-6-sulfonyl chloride, the expected compound is obtained in the form of a brown oil (yield=23%).

$^1$H NMR (300 MHz, DMSO-$d_6$) δ: 8.41 (d, 1H); 7.35 (m, 3H); 7.03 (d, 1H); 6.74 (s, 1H); 4.28 (m, 4H); 3.59 (s, 3H); 3.05 (t, 2H); 2.44 (t, 2H); 1.94 (quint., 2H).

EXAMPLE 181

5-Chloro-1-[(2,3-dihydro-1,4-benzodioxin-6-yl)sulfonyl]-1H-pyrrolo-[3,2-b]pyridine-2-butanoic acid By working in a manner similar to that of Example 2, starting with the ester obtained according to Example 180, the expected compound is obtained in the form of a white solid (yield=95%).

m.p.=166° C.

EXAMPLE 182

5-Chloro-1-[(2-pyridyl)sulfonyl]-1H-pyrrolo[3,2-b]pyridine-2-butanoic acid, methyl ester By working in a manner similar to that of Example 76, starting with 2-pyridinesulfonyl chloride, the expected compound is obtained in the form of a colorless oil (yield=50%).

$^1$H NMR (250 MHz, DMSO-$d_6$) δ: 8.61 (d, 1H); 8.24 (m, 3H); 7.74 (m, 1H); 7.34 (d, 1H); 6.77 (s, 1H); 3.58 (s, 3H); 3.08 (t, 2H); 2.41 (t, 2H); 1.94 (quint., 2H).

EXAMPLE 183

5-Chloro-1-[(2-pyridyl)sulfonyl]-1H-pyrrolo[3,2-b]pyridine-2-butanoic acid

By working in a manner similar to that of Example 2, starting with the ester obtained according to Example 182, the expected compound is obtained in the form of a white solid (yield=30%).

m.p.=187° C.

EXAMPLE 184

5-Chloro-1-[[3-(1-methylethyl)phenyl]sulfonyl]-1H-pyrrolo[3,2-b]pyridine-2-butanoic acid, methyl ester By working in a manner similar to that of Example 76, starting with 3-(1-methylethyl)benzenesulfonyl chloride, the expected compound is obtained in the form of a brown solid (yield=73%).

m.p.=92° C.

EXAMPLE 185

5-Chloro-1-[[3-(1-methylethyl)phenyl]sulfonyl]-1H-pyrrolo[3,2-b]pyridine-2-butanoic acid By working in a manner similar to that of Example 2, starting with the ester obtained according to Example 184, the expected compound is obtained in the form of a white solid (yield=37%).

m.p.=119° C.

EXAMPLE 186

5-Chloro-1-[(4-methyl-1-naphthalenyl)sulfonyl]-1H-pyrrolo[3,2-b]pyridine-2-butanoic acid, methyl ester By working in a manner similar to that of Example 76, starting with 4-methyl-1-naphthalenesulfonyl chloride, the expected compound is obtained in the form of a white solid (yield=85%).

m.p.=118-120° C.

EXAMPLE 187

5-chloro-1-[(4-methyl-1-naphthalenyl)sulfonyl]-1H-pyrrolo[3,2-b]pyridine-2-butanoic acid By working in a manner similar to that of Example 2, starting with the ester obtained according to Example 186, the expected compound is obtained in the form of a beige-colored solid (yield=13%).

m.p.=199-204° C.

EXAMPLE 188

1-[(3,5-Dimethylphenyl)sulfonyl]-5-(trifluoromethyl)-1H-pyrrolo[3,2-b]pyridine-2-butanoic acid, methyl ester By working in a manner similar to that of Example 52, starting with the compound according to Preparation XXII and 3,5-dimethylbenzenesulfonyl chloride, the expected compound is obtained in the form of a white solid (yield=51%).

m.p.=156-160° C.

EXAMPLE 189

1-[(3,5-Dimethylphenyl)sulfonyl]-5-(trifluoromethyl)-1H-pyrrolo[3,2-b]pyridine-2-butanoic acid By working in a manner similar to that of Example 2, starting with the ester obtained according to Example 188, the expected compound is obtained in the form of a white solid (yield=33%).

m.p.=227-231° C.

EXAMPLE 190

5-Chloro-1-[(2,4-dichlorophenyl)sulfonyl]-1H-pyrrolo[3,2-b]pyridine-2-butanoic acid, methyl ester By working in a manner similar to that of Example 76, starting with 2,4-dichlorobenzenesulfonyl chloride, the expected compound is obtained in the form of a white solid (yield=22%).

m.p.=100-101° C.

EXAMPLE 191

5-Chloro-1-[(2,4-dichlorophenyl)sulfonyl]-1H-pyrrolo[3,2-b]pyridine-2-butanoic acid By working in a manner similar to that of Example 2, starting with the ester obtained according to Example 190, the expected compound is obtained in the form of a white solid (yield=96%).

m.p.=154-155° C.

EXAMPLE 192

5-Chloro-1-[(2,3-dichlorophenyl)sulfonyl]-1H-pyrrolo[3,2-b]pyridine-2-butanoic acid, methyl ester By working in a manner similar to that of Example 76, starting with 2,3-dichlorobenzenesulfonyl chloride, the expected compound is obtained in the form of a pink oil (yield=40%).

$^1$H NMR (250 MHz, CDCl$_3$) δ: 8.18 (d, 1H); 7.83 (d, 1H); 7.74 (d, 1H); 7.41 (t, 1H); 7.18 (d, 1H); 6.61 (s, 1H); 3.66 (s, 3H); 2.90 (t, 2H); 2.39 (t, 2H); 2.03 (quint., 2H).

EXAMPLE 193

5-Chloro-1-[(2,3-dichlorophenyl)sulfonyl]-1H-pyrrolo[3,2-b]pyridine-2-butanoic acid By working in a manner similar to that of Example 2, starting with the ester obtained according to Example 192, the expected compound is obtained in the form of a white solid (yield=79%).

m.p.=173-174° C.

EXAMPLE 194

5-Chloro-1-[(3-chloro-2-methylphenyl)sulfonyl]-1H-pyrrolo[3,2-b]pyridine-2-butanoic acid, methyl ester By working in a manner similar to that of Example 76, starting with 3-chloro-2-methylbenzenesulfonyl chloride, the expected compound is obtained in the form of a colorless paste (yield=84%).

$^1$H NMR (250 MHz, CDCl$_3$) δ: 8.21 (d, 1H); 7.61 (d, 1H); 6.98 (m, 2H); 6.95 (d, 1H); 6.65 (s, 1H); 3.66 (s, 3H); 2.87 (t, 2H); 2.55 (s, 3H); 2.38 (t, 2H); 2.02 (quint., 2H).

EXAMPLE 195

5-Chloro-1-[(3-chloro-2-methylphenyl)sulfonyl]-1H-pyrrolo[3,2-b]pyridine-2-butanoic acid By working in a manner similar to that of Example 2, starting with the ester obtained according to Example 194, the expected compound is obtained in the form of a white solid (yield=93%).

m.p.=127-128° C.

EXAMPLE 196

5-Chloro-1-[(4-methoxy-2-methylphenyl)sulfonyl]-1H-pyrrolo[3,2-b]pyridine-2-butanoic acid, methyl ester By working in a manner similar to that of Example 76, starting with 4-methoxy-2-methylbenzenesulfonyl chloride, the expected compound is obtained in the form of a white paste (yield=38%).

$^1$H NMR (250 MHz, DMSO-d$_6$) δ: 8.23 (d, 1H); 7.71 (d, 1H); 7.35 (d, 1H); 6.98 (m, 2H); 6.78 (s, 1H); 3.82 (s, 3H); 3.55 (s, 3H); 2.81 (t, 2H); 2.33 (t, 2H); 2.22 (s, 3H); 1.83 (quint., 2H)).

EXAMPLE 197

5-Chloro-1-[(4-methoxy-2-methylphenyl)sulfonyl]-1H-pyrrolo[3,2-b]pyridine-2-butanoic acid By working in a manner similar to that of Example 2, starting with the ester obtained according to Example 196, the expected compound is obtained in the form of a beige-colored solid (yield=40%).

m.p.=134-140° C.

EXAMPLE 198

1-[(1-Naphthalenyl)sulfonyl]-5-(trifluoromethyl)-1H-pyrrolo[3,2-b]pyridine-2-butanoic acid, methyl ester By working in a manner similar to that of Example 188, starting with 1-naphthalenesulfonyl chloride, the expected compound is obtained in the form of a colorless oil (yield=49%).

$^1$H NMR (250 MHz, DMSO-$d_6$) δ: 8.57 (d, 1H); 8.36 (m, 2H); 8.15 (m, 1H); 7.82 (m, 2H); 7.69 (m, 3H); 7.00 (s, 1H); 3.52 (s, 3H); 2.92 (t, 2H); 2.35 (t, 2H); 1.88 (quint., 2H).

EXAMPLE 199

1-[(1-Naphthalenyl)sulfonyl]-5-(trifluoromethyl)-1H-pyrrolo[3,2-b]pyridine-2-butanoic acid By working in a manner similar to that of Example 2, starting with the ester obtained according to Example 198, the expected compound is obtained in the form of a beige-colored solid (yield=97%).

m.p.=195° C.

EXAMPLE 200

1-(1,3-Benzodioxol-5-ylsulfonyl)-5-(trifluoromethyl)-1H-pyrrolo[3,2-b]pyridine-2-butanoic acid, methyl ester By working in a manner similar to that of Example 188, starting with 1,3-benzodioxole-5-sulfonyl chloride, the expected compound is obtained in the form of a colorless oil (yield=45%).

$^1$H NMR (250 MHz, DMSO-$d_6$) δ: 8.82 (d, 1H); 7.78 (d, 1H); 7.54 (dd, 1H); 7.42 (d, 1H); 7.08 (d, 1H); 6.91 (s, 1H); 6.15 (s, 2H); 3.59 (s, 3H); 3.11 (t, 2H); 2.47 (t, 2H); 1.96 (quint., 2H).

EXAMPLE 201

1-(1,3-Benzodioxol-5-ylsulfonyl)-5-(trifluoromethyl)-1H-pyrrolo[3,2-b]pyridine-2-butanoic acid By working in a manner similar to that of Example 2, starting with the ester obtained according to Example 200, the expected compound is obtained in the form of a white solid (yield=44%).

m.p.=161° C.

EXAMPLE 202

1-[(3,4-Dihydro-4-methyl-2H-1,4-benzoxazin-7-yl)sulfonyl]-5-(trifluoromethyl)-1H-pyrrolo[3,2-b]pyridine-2-butanoic acid, methyl ester By working in a manner similar to that of Example 188, starting with 3,4-dihydro-4-methyl-2H-1,4-benzoxazine-7-sulfonyl chloride, the expected compound is obtained in the form of a beige-colored solid (yield=27%).

m.p.=118° C.

EXAMPLE 203

1-[(3,4-Dihydro-4-methyl-2H-1,4-benzoxazin-7-yl)sulfonyl]-5-(trifluoromethyl)-1H-pyrrolo[3,2-b]pyridine-2-butanoic acid By working in a manner similar to that of Example 2, starting with the ester obtained according to Example 202, the expected compound is obtained in the form of a pink solid (yield=39%).

m.p.=134° C.

EXAMPLE 204

1-[(2-Methyl-7-benzothiazolyl)sulfonyl]-5-(trifluoromethyl)-1H-pyrrolo[3,2-b]pyridine-2-butanoic acid, methyl ester By working in a manner similar to that of Example 188, starting with 2-methyl-7-benzothiazolesulfonyl chloride, the expected compound is obtained in the form of a yellow oil (yield=9%).

$^1$H NMR (250 MHz, DMSO-$d_6$) δ: 8.60 (d, 1H); 8.30 (d, 1H); 7.91 (d, 1H); 7.83 (d, 1H); 7.70 (t, 1H); 6.98 (s, 1H); 3.54 (s, 3H); 2.99 (t, 2H); 2.83 (s, 3H); 2.38 (t, 2H); 1.90 (quint., 2H).

EXAMPLE 205

1-[(2-Methyl-7-benzothiazolyl)sulfonyl]-5-(trifluoromethyl)-1H-pyrrolo[3,2-b]pyridine-2-butanoic acid By working in a manner similar to that of Example 2, starting with the ester obtained according to Example 204, the expected compound is obtained in the form of a beige-colored solid (yield=48%).

m.p.=187° C.

EXAMPLE 206

5-(Trifluoromethyl)-1-[(2,3-dihydro-1,4-benzodioxin-6-yl)sulfonyl]-1H-pyrrolo[3,2-b]pyridine-2-butanoic acid, methyl ester By working in a manner similar to that of Preparation VI, starting with the compound according to Preparation XXII and 2,3-dihydro-1,4-benzodioxine-6-sulfonyl chloride, the expected compound is obtained in the form of a colorless oil (yield=13%).

$^1$H NMR (300 MHz, DMSO-$d_6$) δ: 8.63 (d, 1H); 7.79 (d, 1H); 7.39 (m, 2H); 7.04 (d, 1H); 6.92 (s, 1H); 4.28 (m, 4H); 3.60 (s, 3H); 3.10 (t, 2H); 2.47 (t, 2H); 1.99 (quint., 2H).

EXAMPLE 207

5-(Trifluoromethyl)-1-[(2,3-dihydro-1,4-benzo-dioxin-6-yl)sulfonyl]-1H-pyrrolo[3,2-b]pyridine-2-butanoic acid By working in a manner similar to that of Example 2, starting with the ester obtained according to Example 206, the expected compound is obtained in the form of a white solid (yield=88%).

m.p.=158° C.

EXAMPLE 208

1-(6-Benzothiazolylsulfonyl)-5-chloro-1H-pyrrolo[3,2-b]pyridine-2-pentanoic acid, methyl ester By working in a manner similar to that of Preparation VI, starting with the compound according to Preparation XXIII and benzothiazole-6-sulfonyl chloride, the expected compound is obtained in the form of a colorless paste (yield=36%).

$^1$H NMR (250 MHz, DMSO-d$_6$) δ: 9.68 (s, 1H); 9.02 (d, 1H); 8.46 (d, 1H); 8.23 (d, 1H); 7.92 (dd, 1H); 7.39 (d, 1H); 6.75 (s, 1H); 3.58 (s, 3H); 3.06 (t, 2H); 2.34 (t, 2H); 1.66 (m, 4H).

EXAMPLE 209

1-(6-Benzothiazolylsulfonyl)-5-chloro-1H-pyrrolo[3,2-b]pyridine-2-pentanoic acid By working in a manner similar to that of Example 2, starting with the ester obtained according to Example 208, the expected compound is obtained in the form of a gray solid (yield=43%).

m.p.=169° C.

EXAMPLE 210

2-[[5-Chloro-1-[(4-ethylphenyl)sulfonyl]-1H-pyrrolo[3,2-b]pyrid-2-yl]methoxy]-2-methylpropanoic acid, methyl ester By working in a manner similar to that of Example 42, starting with the compound according to Preparation XXIV, the expected compound is obtained in the form of a yellow oil (yield=74%).

$^1$H NMR (300 MHz, DMSO-d$_6$) δ: 8.42 (d, 1H); 7.92 (d, 2H); 7.45 (d, 1H); 7.42 (d, 2H); 6.90 (s, 1H); 4.87 (s, 2H); 3.66 (s, 3H): 2.65 (q, 2H); 1.45 (s, 6H); 1.13 (t, 3H).

EXAMPLE 211

2-[[5-Chloro-1-[(4-ethylphenyl)sulfonyl]-1H-pyrrolo[3,2-b]pyrid-2-yl]methoxy]-2-methylpropanoic acid By working in a manner similar to that of Example 43, starting with the ester obtained according to Example 210, the expected compound is obtained in the form of a white solid (yield=14%).

m.p.=172° C.

EXAMPLE 212

2-[[5-Chloro-1-[(4-methoxyphenyl)sulfonyl]-1H-pyrrolo[3,2-b]pyrid-2-yl]methoxy]-2-methylpropanoic acid, methyl ester By working in a manner similar to that of Example 42, starting with the compound according to Preparation XXV, the expected compound is obtained in the form of a yellow paste (yield=27%).

$^1$H NMR (250 MHz, DMSO-d$_6$) δ: 8.41 (d, 1H); 7.96 (d, 2H); 7.40 (d, 1H); 7.10 (d, 2H); 6.88 (s, 1H); 4.87 (s, 2H); 3.81 (s, 3H); 3.67 (s, 3H); 1.47 (s, 6H).

EXAMPLE 213

2-[[5-Chloro-1-[(4-methoxyphenyl)sulfonyl]-1H-pyrrolo[3,2-b]pyrid-2-yl]methoxy]-2-methylpropanoic acid By working in a manner similar to that of Example 43, starting with the ester obtained according to Example 212, the expected compound is obtained in the form of a white solid (yield=57%).

m.p.=199° C.

EXAMPLE 214

2-[[5-Chloro-1-[(2,3-dichlorophenyl)sulfonyl]-1H-pyrrolo[3,2-b]pyrid-2-yl]methoxy]-2-methylpropanoic acid, methyl ester By working in a manner similar to that of Example 42, starting with the compound according to Preparation XXVI, the expected compound is obtained in the form of a colorless paste (yield=41%)

$^1$H NMR (300 MHz, DMSO-d$_6$) δ: 8.20 (d, 1H); 8.06 (dd, 1H); 7.72 (dd, 1H); 7.62 (t, 1H); 7.41 (d, 1H); 7.01 (s, 1H); 4.75 (s, 2H); 3.61 (s, 3H); 1.24 (s, 6H).

EXAMPLE 215

2-[[5-Chloro-1-[(2,3-dichlorophenyl)sulfonyl]-1H-pyrrolo[3,2-b]pyrid-2-yl]methoxy]-2-methylpropanoic acid By working in a manner similar to that of Example 43, starting with the ester obtained according to Example 214, the expected compound is obtained in the form of a yellow solid (yield=16%).

m.p.=174° C.

EXAMPLE 216

2-[[5-Chloro-1-[[4-(1-methylethyl)phenyl]sulfonyl]-1H-pyrrolo[3,2-b]pyrid-2-yl]methoxy]-2-methylpropanoic acid, methyl ester By working in a manner similar to that of Example 42, starting with the compound according to Preparation XXVII, the expected compound is obtained in the form of a white solid (yield=87%).

m.p.=120° C.

EXAMPLE 217

2-[[5-Chloro-1-[[4-(1-methylethyl)phenyl]sulfonyl]-1H-pyrrolo[3,2-b]pyrid-2-yl]methoxy]-2-methylpropanoic acid By working in a manner similar to that of Example 43, starting with the ester obtained according to Example 216, the expected compound is obtained in the form of a yellow solid (yield=39%).
m.p.=190° C.

EXAMPLE 218

2-[[5-Chloro-1-(1-naphtalenylsulfonyl)-1H-pyrrolo[3,2-b]pyrid-2-yl]methoxy]-2-methylpropanoic acid, methyl ester By working in a manner similar to that of Example 42, starting with the compound according to Preparation XXVIII, the expected compound is obtained in the form of a white solid (yield=54%).
m.p.=108° C.

EXAMPLE 219

2-[[5-Chloro-1-(1-naphtalenylsulfonyl)-1H-pyrrolo[3,2-b]pyrid-2-yl]methoxy]-2-methylpropanoic acid By working in a manner similar to that of Example 43, starting with the ester obtained according to Example 218, the expected compound is obtained in the form of a bluish solid (yield=36%).
m.p.=209° C.

EXAMPLE 220

2-[[5-Chloro-1-(8-quinolylsulfonyl)-1H-pyrrolo[3,2-b]pyrid-2-yl]-methoxy]-2-methylpropanoic acid, methyl ester By working in a manner similar to that of Example 42, starting with the compound according to Preparation XXIX, the expected compound is obtained in the form of a brown foam (yield=66%).
$^1$H NMR (250 MHz, DMSO-$d_6$) δ: 8.77 (dd, 1H); 8.67 (dd, 1H); 8.51 (dd, 1H); 8.42 (dd, 1H); 8.24 (d, 1H); 7.65 (t, 1H); 7.28 (m, 1H); 7.20 (d, 1H); 6.76 (s, 1H); 5.11 (s, 2H); 3.63 (s, 3H); 1.39 (s, 6H).

EXAMPLE 221

2-[[5-Chloro-1-(8-quinolylsulfonyl)-1H-pyrrolo[3,2-b]pyrid-2-yl]-methoxy]-2-methylpropanoic acid By working in a manner similar to that of Example 43, starting with the ester obtained according to Example 220, the expected compound is obtained in the form of a beige-colored solid (yield=14%).
m.p.=22-3° C.

EXAMPLE 222

2-[[5-Chloro-1-[(2,5-dimethoxyphenyl)sulfonyl]-1H-pyrrolo[3,2-b]pyrid-2-yl]methoxy]-2-methylpropanoic acid, methyl ester By working in a manner similar to that of Example 42, starting with the compound according to Preparation XXX, the expected compound is obtained in the form of a brown oil (yield=37%).
$^1$H NMR (250 MHz, DMSO-$d_6$) δ: 8.20 (d, 1H); 7.52 (d, 1H); 7.36 (d, 1H); 7.32 (dd, 1H); 7.14 (d, 1H); 6.81 (s, 1H); 4.77 (s, 2H); 3.82 (s, 3H); 3.64 (s, 3H); 3.48 (s, 3H); 1.37 (s, 6H).

EXAMPLE 223

2-[[5-Chloro-1-[(2,5-dimethoxyphenyl)sulfonyl]-1H-pyrrolo[3,2-b]pyrid-2-yl]methoxy]-2-methylpropanoic acid By working in a manner similar to that of Example 43, starting with the ester obtained according to Example 222, the expected compound is obtained in the form of a beige-colored solid (yield=23%).
m.p.=200° C.

EXAMPLE 224

2-[[1-(1,3-Benzodioxol-5-ylsulfonyl)-5-chloro-1H-pyrrolo[3,2-b]pyrid-2-yl]methoxy]-2-methylpropanoic acid, methyl ester By working in a manner similar to that of Example 42, starting with the compound according to Preparation XXXI, the expected compound is obtained in the form of a white solid (yield=99%).
m.p.=131° C.

EXAMPLE 225

2-[[1-(1,3-Benzodioxol-5-ylsulfonyl)-5-chloro-1H-pyrrolo[3,2-b]pyrid-2-yl]methoxy]-2-methylpropanoic acid By working in a manner similar to that of Example 43, starting with the ester obtained according to Example 224, the expected compound is obtained in the form of a white solid (yield=39%).
m.p.=172° C.

EXAMPLE 226

2-[[5-Chloro-1-[(2,3-dihydro-1,4-benzodioxin-6-yl)sulfonyl]-1H-pyrrolo[3,2-b]pyrid-2-yl]methoxy]-2-methylpropanoic acid, methyl ester By working in a manner similar to that of Example 42, starting with the compound according to Preparation XXXII, the expected compound is obtained in the form of a brown oil (yield=91%).
$^1$H NMR (500 MHz, DMSO-$d_6$) δ: 8.41 (d, 1H); 7.58 (m, 2H); 7.41 (d, 1H); 7.13 (d, 1H); 6.87 (s, 1H); 4.87 (s, 2H); 4.30 (m, 4H); 3.67 (s, 3H); 1.47 (s, 6H).

EXAMPLE 227

2-[[5-Chloro-1-[(2,3-dihydro-1,4-benzodioxin-6-yl)sulfonyl]-1H-pyrrolo[3,2-b]pyrid-2-yl]methoxy]-2-methylpropanoic acid By working in a manner similar to that of Example 43, starting with the ester obtained according to Example 226, the expected compound is obtained in the form of a beige-colored solid (yield=59%).
m.p.=213° C.

EXAMPLE 228

2-[[5-Chloro-1-(2,3-dihydro-5-benzofuransulfonyl)-1H-pyrrolo[3,2-b]pyrid-2-yl]methoxy]-2-methylpropanoic acid, methyl ester By working in a manner similar to that of Example 42, starting with the compound according to Preparation XXXIII, the expected compound is obtained in the form of a yellow oil (yield=99%).

$^1$H NMR (300 MHz, DMSO-d$_6$) δ: 8.40 (d, 1H); 7.91 (d, 1H); 7.83 (dd, 1H); 7.40 (d, 1H); 6.93 (d, 1H); 6.87 (s, 1H); 4.89 (s, 2H); 4.62 (t, 2H); 3.67 (s, 3H); 3.20 (t, 2H); 1.47 (s, 6H).

EXAMPLE 229

2-[[5-Chloro-1-(2,3-dihydro-5-benzofuransulfonyl)-1H-pyrrolo[3,2-b]pyrid-2-yl]methoxy]-2-methylpropanoic acid By working in a manner similar to that of Example 43, starting with the ester obtained according to Example 228, the expected compound is obtained in the form of a beige-colored solid (yield=26%).

m.p.=169° C.

EXAMPLE 230

2-[[5-Chloro-1-[(3,5-dimethylphenyl)sulfonyl]-1H-pyrrolo[3,2-b]pyrid-2-yl]methoxy]-2-methylpropanoic acid, methyl ester By working in a manner similar to that of Example 42, starting with the compound according to Preparation XXXIV, the expected compound is obtained in the form of a brown oil (yield=99%).

$^1$H NMR (300 MHz, DMSO-d$_6$) δ: 8.40 (d, 1H); 7.64 (s, 2H); 7.40 (d, 1H); 7.38 (s, 1H); 6.89 (s, 1H); 4.90 (s, 2H); 3.66 (s, 3H); 2.31 (s, 6H); 1.45 (s, 6H).

EXAMPLE 231

2-[[5-Chloro-1-[(3,5-dimethylphenyl)sulfonyl]-1H-pyrrolo[3,2-b]pyrid-2-yl]methoxy]-2-methylpropanoic acid By working in a manner similar to that of Example 43, starting with the ester obtained according to Example 230, the expected compound is obtained in the form of a beige-colored solid (yield=40%).

m.p.=154° C.

EXAMPLE 232

2-[[5-Chloro-1-[(3,4-dihydro-4-methyl-2H-1,4-benzoxazin-7-yl)-sulfonyl]-1H-pyrrolo[3,2-b]pyrid-2-yl]methoxy]-2-methylpropanoic acid, methyl ester By working in a manner similar to that of Example 42, starting with the compound according to Preparation XXXV, the expected compound is obtained in the form of a brown oil (yield=99%).

$^1$H NMR (300 MHz, DMSO-d$_6$) δ: 8.44 (d, 1H); 7.39 (d, 1H); 7.15 (dd, 1H); 6.98 (d, 1H); 6.82 (m, 2H); 4.87 (s, 2H); 4.25 (t, 2H); 3.66 (s, 3H); 3.26 (t, 2H); 2.83 (s, 3H); 1.45 (s, 6H).

EXAMPLE 233

2-[[5-Chloro-1-[(3,4-dihydro-4-methyl-2H-1,4-benzoxazin-7-yl)sulfonyl]-1H-pyrrolo[3,2-b]pyrid-2-yl]methoxy]-2-methylpropanoic acid By working in a manner similar to that of Example 43, starting with the ester obtained according to Example 232, the expected compound is obtained in the form of a pink solid (yield=37%).

m.p.=229° C.

EXAMPLE 234

(2S)-2-[[5-Chloro-1-(phenylsulfonyl)-1H-pyrrolo[3,2-b]pyrid-2-yl]methoxy]propanoic acid, ethyl ester a)—Ethyl ester of (2S)-2-(2-propynyloxy)propanoic acid: this compound is obtained, in a yield of 24%, by reacting propargyl bromide with the ethyl ester of (S)-(−)-lactic acid sodium-treated beforehand with sodium hydride in THF (colorless liquid; b.p.=70-73° C. at 13 hPa).

b)—By working in a manner similar to that of Example 1, starting with the ester obtained in a) above, the expected compound is obtained in the form of a yellow oil (yield=19%).

$^1$H NMR (300 MHz, DMSO-d$_6$) δ: 8.42 (d, 1H); 8.02 (d, 2H); 7.74 (m, 1H); 7.60 (m, 2H); 7.43 (d, 1H); 6.95 (s, 1H); 5.04 (d, 1H); 4.92 (d, 1H); 4.23 (q, 1H); 4.12 (q, 2H); 1.31 (d, 3H); 1.16 (t, 3H)

EXAMPLE 235

(2S)-2-[[5-Chloro-1-(phenylsulfonyl)-1H-pyrrolo[3,2-b]pyrid-2-yl]methoxy]propanoic acid By working in a manner similar to that of Example 2, starting with the ester obtained according to Example 234, the expected compound is obtained in the form of a pink solid (yield=33%).

m.p.=154° C.

[α]$_D$=−50° (c=0.39; MeOH).

EXAMPLE 236

(2R)-2-[[5-Chloro-1-(phenylsulfonyl)-1H-pyrrolo[3,2-b]pyrid-2-yl]methoxy]propanoic acid, methyl ester By working in a manner similar to that of Example 234, starting with the methyl ester of (R)-(+)-lactic acid, the following are obtained:

a)—Methyl ester of (2R)-2-(2-propynyloxy)propanoic acid: (colorless liquid; b.p.=81-88° C. at atmospheric pressure).

b)—The expected compound in the form of a yellow oil (yield=73%).

$^1$H NMR (300 MHz, DMSO-d$_6$) δ: 8.42 (d, 1H); 8.01 (dd, 2H); 7.73 (m, 1H); 7.63 (m, 2H); 7.43 (d, 1H); 6.96 (s, 1H); 5.05 (d, 1H); 4.92 (d, 1H); 4.26 (q, 1H); 3.66 (s, 3H); 1.31 (d, 3H).

EXAMPLE 237

(2R)-2-[[5-Chloro-1-(phenylsulfonyl)-1H-pyrrolo[3,2-b]pyrid-2-yl]-methoxy]propanoic acid By working in a manner similar to that of Example 2, starting with the ester obtained according to Example 236, the expected compound is obtained in the form of a white solid (yield=58%).

m.p.=150° C.

$[\alpha]_D$=+50° (c=0.375; MeOH).

EXAMPLE 238

(2S)-2-[[1-(Phenylsulfonyl)-5-(trifluoromethyl)-1H-pyrrolo[3,2-b]pyrid-2-yl]-methoxy]propanoic acid, ethyl ester By working in a manner similar to that of Example 234, starting with the compound according to Preparation VII, the expected compound is obtained in the form of a yellow oil (yield=91%).

$^1$H NMR (300 MHz, DMSO-$d_6$) δ: 8.63 (d, 1H); 8.06 (dd, 2H); 7.84 (d, 1H); 7.74 (m, 1H); 7.62 (m, 2H); 7.12 (s, 1H); 5.10 (d, 1H); 4.97 (d, 1H); 4.26 (q, 1H); 4.15 (q, 2H); 1.31 (d, 3H); 1.18 (t, 3H).

EXAMPLE 239

(2S)-2-[[1-(Phenylsulfonyl)-5-(trifluoromethyl)-1H-pyrrolo[3,2-b]pyrid-2-yl]-methoxy]propanoic acid By working in a manner similar to that of Example 2, starting with the ester obtained according to Example 238, the expected compound is obtained in the form of a beige-colored solid (yield=60%).

m.p.=142° C.

$[\alpha]_D$=−46° (c=0.52; MeOH).

EXAMPLE 240

(2R)-2-[[1-(Phenylsulfonyl)-5-(trifluoromethyl)-1H-pyrrolo[3,2-b]pyrid-2-yl]-methoxy]propanoic acid, methyl ester By working in a manner similar to that of Example 236, starting with the compound according to Preparation VII, the expected compound is obtained in the form of a yellow oil (yield=88%).

$^1$H NMR (300 MHz, DMSO-$d_6$) δ: 8.63 (d, 1H); 8.06 (d, 2H); 7.83 (d, 1H); 7.75 (m, 1H); 7.62 (t, 2H); 7.13 (s, 1H); 5.10 (d, 1H); 4.96 (d, 1H); 4.28 (q, 1H); 3.66 (s, 3H); 1.31 (d, 3H).

EXAMPLE 241

(2R)-2-[[1-(Phenylsulfonyl)-5-(trifluoromethyl)-1H-pyrrolo[3,2-b]pyrid-2-yl]-methoxy]propanoic acid By working in a manner similar to that of Example 2, starting with the ester obtained according to Example 240, the expected compound is obtained in the form of a beige-colored solid (yield=78%).

m.p.=140° C.

$[\alpha]_D$=+39° (c=0.39; MeOH).

EXAMPLE 242

5-Methyl-1-(phenylsulfonyl)-1H-pyrrolo[3,2-b]pyridine-2-propanoic acid, methyl ester By working in a manner similar to that of Example 1, starting with the compound according to Preparation XXXVI, the expected compound is obtained in the form of a brown solid (yield=56%).

m.p.=98-115° C.

EXAMPLE 243

5-Methyl-1-(phenylsulfonyl)-1H-pyrrolo[3,2-b]pyridine-2-propanoic acid

By working in a manner similar to that of Example 2, starting with the ester obtained according to Example 242, the expected compound is obtained in the form of a yellow solid (yield=21%).

m.p.=88-92° C.

EXAMPLE 244

5-Methoxy-1-(phenylsulfonyl)-1H-pyrrolo[3,2-b]pyridine-2-propanoic acid, methyl ester By working in a manner similar to that of Example 1, starting with the compound according to Preparation XXXVIII, the expected compound is obtained in the form of a white solid (yield=63%).

m.p.=145-150° C.

EXAMPLE 245

5-Methoxy-1-(phenylsulfonyl)-1H-pyrrolo[3,2-b]pyridine-2-propa-noic acid

By working in a manner similar to that of Example 2, starting with the ester obtained according to Example 244, the expected compound is obtained in the form of a beige-colored solid (yield=75%).

m.p.=136-139° C.

EXAMPLE 246

5-Methoxy-1-(phenylsulfonyl)-1H-pyrrolo[3,2-b]pyridine-2-butanoic acid, methyl ester By working in a manner similar to that of Example 1, starting with the compound according to Preparation XL, the expected compound is obtained in the form of a yellow solid (yield=86%).

m.p.=113-114° C.

EXAMPLE 247

5-Methoxy-1-(phenylsulfonyl)-1H-pyrrolo[3,2-b]pyridine-2-butanoic acid

By working in a manner similar to that of Example 2, starting with the ester obtained according to Example 246, the expected compound is obtained in the form of a beige-colored solid (yield=34%).

m.p.=190-198° C.

EXAMPLE 248

5-Methyl-1-(phenylsulfonyl)-1H-pyrrolo[3,2-b]pyridine-2-butanoic acid, methyl ester By working in a manner similar to that of Example 242, starting with the methyl ester of 5-hexynoic acid, the expected compound is obtained in the form of a yellow solid (yield=92%).
m.p.=91-94° C.

EXAMPLE 249

5-Methyl-1-(phenylsulfonyl)-1H-pyrrolo[3,2-b]pyridine-2-butanoic acid

By working in a manner similar to that of Example 2, starting with the ester obtained according to Example 248, the expected compound is obtained in the form of a yellow solid (yield 38%).
m.p.=172-180° C.

EXAMPLE 250

1-(6-Benzothiazolylsulfonyl)-5-methyl-1H-pyrrolo[3,2-b]pyridine-2-butanoic acid, methyl ester By working in a manner similar to that of Example 248, starting with the compound according to Preparation XLI, the expected compound is obtained in the form of a yellow solid (yield=76%).
$^1$H NMR (300 MHz, DMSO-$d_6$) δ: 9.65 (s, 1H); 8.97 (d, 1H); 8.29 (d, 1H); 8.20 (d, 1H); 7.85 (dd, 1H); 7.17 (d, 1H); 6.66 (s, 1H); 3.58 (s, 3H); 3.10 (t, 2H); 2.49 (s, 3H); 2.41 (t, 2H); 1.99 (quint., 2H).

EXAMPLE 251

1-(6-Benzothiazolylsulfonyl)-5-methyl-1H-pyrrolo[3,2-b]pyridine-2-butanoic acid

By working in a manner similar to that of Example 2, starting with the ester obtained according to Example 250, the expected compound is obtained in the form of a violet-colored solid (yield=14%).
m.p.=67-70° C.

EXAMPLE 252

5-Chloro-1-(3-pyridylsulfonyl)-1H-pyrrolo[3,2-b]pyridine-2-butanoic acid, methyl ester By working in a manner similar to that of Example 248, starting with the compound according to Preparation XLII, the expected compound is obtained in the form of a white solid (yield=57%).
m.p.=119° C.

EXAMPLE 253

5-Chloro-1-(3-pyridylsulfonyl)-1H-pyrrolo[3,2-b]pyridine-2-butanoic acid

By working in a manner similar to that of Example 2, starting with the ester obtained according to Example 252, the expected compound is obtained in the form of a white solid (yield=73%).
m.p.=181° C.

EXAMPLE 254

5-Chloro-1-(6-quinolylsulfonyl)-1H-pyrrolo[3,2-b]pyridine-2-butanoic acid, methyl ester By working in a manner similar to that of Example 248, starting with the compound according to Preparation XLIII, the expected compound is obtained in the form of a brown solid (yield=72%).
m.p.=133-141° C.

EXAMPLE 255

5-Chloro-1-(6-quinolylsulfonyl)-1H-pyrrolo[3,2-b]pyridine-2-butanoic acid

By working in a manner similar to that of Example 2, starting with the ester obtained according to Example 254, the expected compound is obtained in the form of a beige-colored solid (yield=40%).
m.p.=153-162° C.

EXAMPLE 256

5-Chloro-1-(phenylsulfonyl)-1H-pyrrolo[3,2-b]pyridine-2-pentanoic acid, methyl ester By working in a manner similar to that of Example 1, starting with the methyl ester of heptynoic acid, the expected compound is obtained in the form of a white solid (yield=37%).
m.p.=73° C.

EXAMPLE 257

5-Chloro-1-(phenylsulfonyl)-1H-pyrrolo[3,2-b]pyridine-2-pentanoic acid

By working in a manner similar to that of Example 2, starting with the ester obtained according to Example 256, the expected compound is obtained in the form of a beige-colored solid (yield=69%).
m.p.=113° C.

EXAMPLE 258

5-Chloro-1-[(3,5-dimethylphenyl)sulfonyl]-1H-pyrrolo[3,2-b]pyridine-2-pentanoic acid, methyl ester By working in a manner similar to that of Example 256, starting with the compound according to Preparation XXXIV, the expected compound is obtained in the form of a beige-colored solid (yield=84%).
m.p.=126° C.

EXAMPLE 259

5-Chloro-1-[(3,5-dimethylphenyl)sulfonyl]-1H-pyrrolo[3,2-b]pyridine-2-pentanoic acid By working in a manner similar to that of Example 2, starting with the ester obtained according to Example 258, the expected compound is obtained in the form of a white solid (yield=84%).
m.p.=160° C.

EXAMPLE 260

5-Chloro-α,α-dimethyl-1-(phenylsulfonyl)-1H-pyrrolo[3,2-b]pyridine-2-butanoic acid, By working in a manner similar to that of Example 1, starting with 2,2-dimethylhexynoic acid, the expected compound is obtained in the form of a beige-colored solid (yield=14%).
m.p.=197° C.

EXAMPLE 261

1-(6-Benzothiazolylsulfonyl)-5-chloro-α,α-dimethyl-1H-pyrrolo[3,2-b]pyridine-2-butanoic acid By working in a manner similar to that of Example 1, starting with 2,2-dimethylhexynoic acid and the compound according to Preparation XLIV, the expected compound is obtained in the form of a beige-colored solid (yield=8%).
m.p.=210° C.

EXAMPLE 262

1-[[4-(1-Methylethyl)phenyl]sulfonyl]-5-(trifluoromethyl)-1H-pyrrolo-[3,2-b]pyridine-2-butanoic acid, methyl ester A solution of 0.263 g (0.92 mM) of the compound according to Preparation XLV in 10 ml of DMF is prepared and 73 mg (1.8 mM) of sodium hydride as a 60% suspension in oil are added at 0° C. The mixture is stirred for 15 minutes at 0° C., and 0.302 g (1.4 mM) of 4-(1-methylethyl)benzenesulfonamide chloride is then added. The reaction medium is stirred for 60 hours at room temperature and then poured into a mixture of crushed ice and ammonium chloride, and extracted with ethyl acetate. The organic phase obtained is dried over magnesium sulfate and concentrated under reduced pressure.

The expected compound is thus obtained in the form of a brown solid (yield=93%).
m.p.=78° C.

EXAMPLE 263

1-[[4-(1-Methylethyl)phenyl]sulfonyl]-5-(trifluoromethyl)-1H-pyrrolo-[3,2-b]pyridine-2-butanoic acid By working in a manner similar to that of Example 2, starting with the ester obtained according to Example 262, the expected compound is obtained in the form of a pale green solid (yield=50%).
m.p.=144° C.

EXAMPLE 264

1-[(4-Chlorophenyl)sulfonyl]-5-(trifluoromethyl)-1H-pyrrolo[3,2-b]pyridine-2-butanoic acid, methyl ester By working in a manner similar to that of Example 262, starting with 4-chlorobenzenesulfonyl chloride, the expected compound is obtained in the form of a white solid (yield=47%).
m.p.=97° C.

EXAMPLE 265

1-[(4-Chlorophenyl)sulfonyl]-5-(trifluoromethyl)-1H-pyrrolo[3,2-b]pyridine-2-butanoic acid By working in a manner similar to that of Example 2, starting with the ester obtained according to Example 264, the expected compound is obtained in the form of a pale green solid (yield=37%).
m.p.=176° C.

EXAMPLE 266

1-[(2-Chlorophenyl)sulfonyl]-5-(trifluoromethyl)-1H-pyrrolo[3,2-b]pyridine-2-butanoic acid, methyl ester By working in a manner similar to that of Example 262, starting with 2-chlorobenzenesulfonyl chloride, the expected compound is obtained in the form of a beige-colored solid (yield=71%).
m.p.=88° C.

EXAMPLE 267

1-[(2-Chlorophenyl)sulfonyl]-5-(trifluoromethyl)-1H-pyrrolo[3,2-b]pyridine-2-butanoic acid By working in a manner similar to that of Example 2, starting with the ester obtained according to Example 266, the expected compound is obtained in the form of a pale green solid (yield=50%).
m.p.=171° C.

EXAMPLE 268

1-[[(3-(Trifluoromethoxy)phenyl]sulfonyl]-5-(trifluoromethyl)-1H-pyrrolo[3,2-b]pyridine-2-butanoic acid, methyl ester By working in a manner similar to that of Example 262, starting with 3-(trifluoromethoxy)benzenesulfonyl chloride, the expected compound is obtained in the form of an ochre-colored solid (yield=88%).
m.p.=72° C.

EXAMPLE 269

1-[[(3-(Trifluoromethoxy)phenyl]sulfonyl]-5-(trifluoromethyl)-1H-pyrrolo[3,2-b]pyridine-2-butanoic acid By working in a manner similar to that of Example 2, starting with the ester obtained according to Example 268, the expected compound is obtained in the form of a beige-colored solid (yield=27%).
m.p.=164° C.

EXAMPLE 270

1-[(4-Bromophenyl)sulfonyl]-5-chloro-1H-pyrrolo[3,2-b]pyridine-2-butanoic acid, methyl ester By working in a manner similar to that of Example 52, starting with the ester according to Preparation V and 4-bromobenzenesulfonamide chloride, the expected compound is obtained in the form of a white solid (yield=97%).
m.p.=102° C.

EXAMPLE 271

5-Chloro-1-[[4-(4-morpholinyl)phenyl]sulfonyl]-1H-pyrrolo[3,2-b]pyridine-2-butanoic acid, methyl ester 1.5 mg of tris(benzylideneacetone)dipalladium, 2 mg of di(t-butyl)([1,1'-biphenyl]2-yl)phosphine, 48 mg (0.22 mM) of potassium phosphate, 75 mg (0.159 mM) of the compound obtained according to Example 270 and 0.16 ml of DME are placed in a reactor tube adapted for heating by microwave, while maintaining under an argon atmosphere. These compounds are mixed together and 17 mg (0.19 mM) of morpholine and 0.32 ml of DME are added. This reaction mixture is heated by microwave at 110° C. for 2 hours and then concentrated under reduced pressure. The residue is purified by chromatography on silica gel, eluting with a toluene/ethyl acetate mixture (as a gradient from 9/1 to 8/2; v/v). The expected compound is thus obtained in the form of a white solid (yield=80%).

m.p.=110° C.

EXAMPLE 272

5-Chloro-1-[[4-(4-morpholinyl)phenyl]sulfonyl]-1H-pyrrolo[3,2-b]pyridine-2-butanoic acid By working in a manner similar to that of Example 2, starting with the ester obtained according to Example 271, the expected compound is obtained in the form of a white solid (yield=55%).

m.p.=176° C.

EXAMPLE 273

5-Chloro-1-[[4-(1-pyrrolidinyl)phenyl]sulfonyl]-1H-pyrrolo[3,2-b]pyridine-2-butanoic acid, methyl ester By working in a manner similar to that of Example 271, starting with pyrrolidine, the expected compound is obtained in the form of a white solid (yield=63%).

m.p.=121° C.

EXAMPLE 274

5-Chloro-1-[[4-(1-pyrrolidinyl)phenyl]sulfonyl]-1H-pyrrolo[3,2-b]pyridine-2-butanoic acid By working in a manner similar to that of Example 2, starting with the ester obtained according to Example 273, the expected compound is obtained in the form of a white solid (yield=99%).

m.p.=88° C.

EXAMPLE 275

5-Chloro-1-[[4-(dimethylamino)phenyl]sulfonyl]-1H-pyrrolo[3,2-b]pyridine-2-butanoic acid, methyl ester By working in a manner similar to that of Example 271, starting with dimethylamine as a 2 N solution in THF, the expected compound is obtained in the form of a white solid (yield=35%).

m.p.=188° C.

EXAMPLE 276

5-Chloro-1-[[4-(dimethylamino)phenyl]sulfonyl]-1H-pyrrolo[3,2-b]pyridine-2-butanoic acid By working in a manner similar to that of Example 2, starting with the ester obtained according to Example 275, the expected compound is obtained in the form of a white solid (yield=99%).

m.p.=76° C.

EXAMPLE 277

5-Chloro-1-[(3-bromophenyl)sulfonyl]-1H-pyrrolo[3,2-b]pyridine-2-butanoic acid, methyl ester By working in a manner similar to that of Example 52, starting with the ester according to Preparation V and 3-bromobenzenesulfonamide chloride, the expected compound is obtained in the form of a white solid (yield=97%).

m.p.=109° C.

EXAMPLE 278

5-Chloro-1-[[3-(dimethylamino)phenyl]sulfonyl]-1H-pyrrolo[3,2-b]pyridine-2-butanoic acid, methyl ester By working in a manner similar to that of Example 275, starting with dimethylamine as a 2 N solution in THF and the bromo derivative obtained according to Example 277, the expected compound is obtained in the form of a beige-colored solid (yield=6%).

m.p.=96-97° C.

EXAMPLE 279

5-Chloro-1-[(4-iodophenyl)sulfonyl]-1H-pyrrolo[3,2-b]pyridine-2-butanoic acid, methyl ester By working in a manner similar to that of Example 52, starting with the ester according to Preparation V and 4-iodobenzenesulfonamide chloride, the expected compound is obtained in the form of a beige-colored solid (yield=70%).

m.p.=117-118° C.

EXAMPLE 280

5-Chloro-1-[[4-(2-thiazolyl)phenyl]sulfonyl]-1H-pyrrolo[3,2-b]pyridine-2-butanoic acid, methyl ester A solution of 249 mg (0.48 mM) of the compound obtained according to Example 279 in 2.5 ml of toluene is prepared in a reactor tube adapted for heating by microwave, and 110 mg (0.096 mM) of tetrakis(triphenyl)phosphine and then 0.15 ml of 2-(tributylstannyl)thiazole and 0.4 ml of N-methylpyrrolidinone are added. The mixture is then heated at 100° C. by microwave for 1 hour 30 minutes. After cooling, water is added and the resulting mixture is extracted with diethyl ether. The organic phase obtained is washed with water and then dried over magnesium sulfate and concentrated under reduced pressure. The crude product obtained is purified by chromatography on silica gel, eluting with a petroleum ether/diethyl ether mixture (6/4; v/v). The purified compound is recrystallized from a mixture of diethyl ether and petroleum ether. The expected compound is obtained in the form of a yellow solid (yield=57%).

m.p.=101° C.

EXAMPLE 281

5-Chloro-1-[[4-(2-thiazolyl)phenyl]sulfonyl]-1H-pyrrolo[3,2-b]pyridine-2-butanoic acid By working in a manner similar to that of Example 2, starting with the ester obtained according to Example 280, the expected compound is obtained in the form of a white solid (yield=44%).

m.p.=214-215° C.

EXAMPLE 282

5-Chloro-1-[[3-(2-thiazolyl)phenyl]sulfonyl]-1H-pyrrolo[3,2-b]pyridine-2-butanoic acid, methyl ester By working in a manner similar to that of Example 280, starting with the bromo derivative obtained according to Example 277, the expected compound is obtained in the form of a white solid (yield=32%).

m.p.=82-86° C.

EXAMPLE 283

5-Chloro-1-[[3-(2-thiazolyl)phenyl]sulfonyl]-1H-pyrrolo[3,2-b]pyridine-2-butanoic acid By working in a manner similar to that of Example 2, starting with the ester obtained according to Example 282, the expected compound is obtained in the form of a white solid (yield=68%).

m.p.=187-188° C.

EXAMPLE 284

5-Chloro-1-[[3-(5-thiazolyl)phenyl]sulfonyl]-1H-pyrrolo[3,2-b]pyridine-2-butanoic acid, methyl ester By working in a manner similar to that of Example 282, starting with the bromo derivative obtained according to Example 277 and 5-(tributylstannyl)thiazole, the expected compound is obtained in the form of a white solid (yield=71%).

m.p.=147-148° C.

EXAMPLE 285

5-Chloro-1-[[3-(5-thiazolyl)phenyl]sulfonyl]-1H-pyrrolo[3,2-b]pyridine-2-butanoic acid By working in a manner similar to that of Example 2, starting with the ester obtained according to Example 284, the expected compound is obtained in the form of a white solid (yield=45%).

m.p.=157-160° C.

EXAMPLE 286

5-Chloro-1-[[3-(4-thiazolyl)phenyl]sulfonyl]-1H-pyrrolo[3,2-b]pyridine-2-butanoic acid, methyl ester By working in a manner similar to that of Example 282, starting with the bromo derivative obtained according to Example 277 and 4-(tributylstannyl)thiazole, the expected compound is obtained in the form of a white solid (yield=38%).

m.p.=147-148° C.

EXAMPLE 287

5-Chloro-1-[[3-(4-thiazolyl)phenyl]sulfonyl]-1H-pyrrolo[3,2-b]pyridine-2-butanoic acid By working in a manner similar to that of Example 2, starting with the ester obtained according to Example 286, the expected compound is obtained in the form of a white solid (yield=4%).

m.p.=185-186° C.

EXAMPLE 288

5-Chloro-1-[[4-(2-pyridyl)phenyl]sulfonyl]-1H-pyrrolo[3,2-b]pyridine-2-butanoic acid, methyl ester By working in a manner similar to that of Example 280, starting with the bromo derivative obtained according to Example 270 and 2-(tributylstannyl)pyridine, the expected compound is obtained in the form of an orange-colored solid (yield=61%).

m.p.=123-124° C.

EXAMPLE 289

5-Chloro-1-[[4-(2-pyridyl)phenyl]sulfonyl]-1H-pyrrolo[3,2-b]pyridine-2-butanoic acid By working in a manner similar to that of Example 2, starting with the ester obtained according to Example 288, the expected compound is obtained in the form of a beige-colored solid (yield=40%).

m.p.=214-215° C.

EXAMPLE 290

5-Chloro-1-[[4-(3-pyridyl)phenyl]sulfonyl]-1H-pyrrolo[3,2-b]pyridine-2-butanoic acid, methyl ester A mixture of 300 mg (0.63 mM) of the compound obtained according to Example 270, 98 mg (0.80 mM) of 3-pyridineboronic acid and 0.9 ml of a 2 M solution of potassium carbonate in 5 ml of DME is prepared in a reactor tube adapted for heating by microwave, and 6 mg of PdCl$_2$dppf are added. The mixture is then heated at 120° C. by microwave for 1 hour. After cooling, water is added and the resulting mixture is extracted with ethyl acetate. The organic phase obtained is washed with water and then dried over magnesium sulfate and concentrated under reduced pressure. The crude product obtained is purified by chromatography on silica gel, eluting with a cyclohexane/ethyl acetate mixture (80/20 and then 70/30; v/v). The expected compound is thus obtained in the form of a colorless oil (yield=37%).

$^1$H NMR (300 MHz, DMSO-d$_6$) δ: 8.90 (d, 1H); 8.63 (dd, 1H); 8.47 (d, 1H); 8.11 (m, 1H); 7.97 (m, 4H); 7.51 (m, 1H); 7.41 (d, 1H); 6.79 (s, 1H); 3.58 (s, 3H); 3.10 (t, 2H); 2.49 (s, 3H); 2.46 (t, 2H); 1.99 (quint., 2H).

EXAMPLE 291

5-Chloro-1-[[4-(3-pyridyl)phenyl]sulfonyl]-1H-pyrrolo[3,2-b]pyridine-2-butanoic acid By working in a manner similar to that of Example 2, starting with the ester obtained according to Example 290, the expected compound is obtained in the form of a white solid (yield=92%).
m.p.=141° C.

EXAMPLE 292

5-Chloro-1-[[4-(4-pyridyl)phenyl]sulfonyl]-1H-pyrrolo[3,2-b]pyridine-2-butanoic acid, methyl ester By working in a manner similar to that of Example 290, starting with 4-pyridineboronic acid, the expected compound is obtained in the form of a white solid (yield=70%).
m.p.=215° C.

EXAMPLE 293

5-Chloro-1-[[4-(4-pyridyl)phenyl]sulfonyl]-1H-pyrrolo[3,2-b]pyridine-2-butanoic acid By working in a manner similar to that of Example 2, starting with the ester obtained according to Example 292, the expected compound is obtained in the form of a white solid (yield=77%).
m.p.=174° C.

EXAMPLE 294

5-Chloro-1-[(4-fluoro-3-nitrophenyl)sulfonyl]-1H-pyrrolo[3,2-b]pyridine-2-butanoic acid, methyl ester By working in a manner similar to that of Example 3, starting with the ester according to Preparation XLVI, the expected product is obtained in the form of a yellow solid (yield=88%).
m.p.=129-131° C.

EXAMPLE 295

1-[(5-Benzothiazolyl)sulfonyl]-5-chloro-1H-pyrrolo[3,2-b]pyridine-2-butanoic acid, methyl ester A solution of 0.21 g (0.46 mM) of the compound obtained according to Example 294 in 2 ml of pyridine is prepared and 0.323 g (4.37 mM) of sodium hydrogen sulfide monohydrate suspended in 2 ml of ethylene glycol is added, at room temperature, followed by addition of 1 ml of pyridine. The mixture is stirred for 30 minutes at room temperature, and then poured into a mixture of water and ice. The mixture is brought to pH 2 by adding dilute hydrochloric acid, and is extracted with ethyl acetate. The organic phase obtained is washed with N hydrochloric acid solution, and then with water, dried over magnesium sulfate and concentrated under reduced pressure. The crude product obtained is purified by chromatography on silica gel, eluting with a toluene/ethyl acetate mixture (90/10 and then 75/25; v/v). 160 mg of the methyl ester of 5-chloro-1-[(4-mercapto-3-nitrophenyl)sulfonyl]-1H-pyrrolo[3,2-b]pyridine-2-butanoic acid (yellow oil) are thus obtained. This compound is redissolved in 4 ml of acetic acid and 99 mg (1.7 mM) of iron powder are added, with stirring and at room temperature. The reaction mixture is stirred at 70° C. for 2 hours and then concentrated under reduced pressure. The evaporation residue is taken up in water and ethyl acetate. The aqueous phase is separated out and re-extracted with ethyl acetate. The combined organic phases are washed with water, with sodium carbonate solution and then with brine, dried over magnesium sulfate and concentrated under reduced pressure. 150 mg of the methyl ester of 1-[(3-amino-4-mercaptophenyl)sulfonyl]-5-chloro-1H-pyrrolo[3,2-b]pyridine-2-butanoic acid (orange foam, not purified) are thus obtained. This product is taken up in 3 ml of formic acid and 80 mg of zinc powder are added with stirring. The reaction mixture is stirred for 3 hours at 100° C., and then cooled and poured into water. This aqueous phase is brought to pH 4 by adding N sodium hydroxide solution and is extracted with ethyl acetate. The organic phase obtained is washed with sodium bicarbonate solution, with N sodium hydroxide solution and then with water, dried over magnesium sulfate and concentrated under reduced pressure. The crude product obtained is purified by chromatography on silica gel, eluting with a toluene/ethyl acetate mixture (95/5 and then 80/20; v/v). The expected compound is thus obtained in the form of a colorless oil (yield=47%).
$^1$H NMR (500 MHz, DMSO-$d_6$) δ: 9.62 (s, 1H); 8.61 (s, 1H); 8.53 (d, 1H); 8.44 (d, 1H); 7.90 (dd, 1H); 7.40 (d, 1H); 6.78 (s, 1H); 3.59 (s, 3H); 3.13 (t, 2H); 2.46 (t, 2H); 1.99 (quint., 2H).

EXAMPLE 296

5-Chloro-1-[(5-benzothiazolyl)sulfonyl]-1H-pyrrolo[3,2-b]pyridine-2-butanoic acid By working in a manner similar to that of Example 2, starting with the ester obtained according to Example 295, the expected compound is obtained in the form of a white solid (yield=24%).
m.p.=202-206° C.

EXAMPLE 297

1-[(4-Amino-3-nitrophenyl)sulfonyl]-5-chloro-1H-pyrrolo[3,2-b]pyridine-2-butanoic acid, methyl ester A mixture of 400 mg (0.874 mM) of the compound obtained according to Example 294 in 4 ml of dioxane is prepared and 0.31 ml 32% is added cautiously, with stirring. The reaction mixture is kept stirring for one hour, at room temperature, and 20 ml of ethyl acetate are then added. This organic phase is washed with water and then with brine, dried over magnesium sulfate and concentrated under reduced pressure. 375 mg of the expected compound are thus obtained in the form of a yellow solid (yield=95%).
m.p.=154-156° C.

EXAMPLE 298

5-Chloro-1-[(3,4-diaminophenyl)sulfonyl]-1H-pyrrolo[3,2-b]pyridine-2-butanoic acid, methyl ester A solution of 365 mg (0.806 mM) of the compound obtained according to Example 297 in 5 ml of acetic acid is prepared and 225 mg (4.03 mM) of iron powder are added, with stirring and at room temperature. The reaction mixture is stirred at 70° C. for 3 hours and then concentrated under reduced pressure. The evaporation residue is taken up in water and ethyl acetate. The aqueous phase is separated out and re-extracted with ethyl acetate. The combined organic phases are washed with water, with sodium carbonate solution and then with brine, dried over magnesium sulfate and concentrated under reduced pressure. 313 mg of the expected compound are thus obtained in the form of a yellow solid (yield=92%).
m.p.=162-164° C.

EXAMPLE 299

1-[(6-Benzopyrazinyl)sulfonyl]-5-chloro-1H-pyrrolo[3,2-b]pyridine-2-butanoic acid, methyl ester A mixture of 150 mg (0.355 mM) of the compound obtained according to Example 298 in 1.25 ml of acetonitrile is prepared and 0.11 ml (0.95 mM) of glyoxal is added, with stirring. The reaction mixture is kept stirring for 14 hours, at 50° C., and then concentrated under reduced pressure and taken up in 10 ml of ethyl acetate. This organic phase is washed with water and then with brine, dried over magnesium sulfate and concentrated under reduced pressure. The crude product obtained is purified by chromatography on silica gel, eluting with a toluene/ethyl acetate mixture (95/5 and then 80/20; v/v). The expected compound is thus obtained in the form of a yellow solid (yield=58%).

$^1$H NMR (250 MHz, DMSO) δ: 9.12 (m, 2H); 8.65 (d, 1H); 8.53 (d, 1H); 8.28 (d, 1H); 8.09 (dd, 1H); 7.41 (d, 1H); 6.81 (s, 1H); 3.56 (s, 3H); 3.12 (t, 2H); 2.45 (t, 2H); 1.98 (quint., 2H).

EXAMPLE 300

1-[(6-Benzopyrazinyl)sulfonyl]-5-chloro-1H-pyrrolo[3,2-b]pyridine-2-butanoic acid By working in a manner similar to that of Example 2, starting with the ester obtained according to Example 299, the expected compound is obtained in the form of a beige-colored solid (yield=31%).
m.p.=103-106° C.

EXAMPLE 301

5-Chloro-1-[(2,3-dihydro-1H-indol-5-yl)sulfonyl]-1H-pyrrolo[3,2-b]pyridine-2-butanoic acid By working in a manner similar to that of Example 2, starting with the ester obtained according to Example 104, the expected compound is obtained in the form of a beige-colored solid (yield=37%).
m.p.=190° C.

EXAMPLE 302

5-Chloro-1-[(2,3-dihydro-1H-indol-5-yl)sulfonyl]-1H-pyrrolo[3,2-b]pyridine-2-propanoic acid By working in a manner similar to that of Example 2, starting with the ester obtained according to Example 66, the expected compound is obtained in the form of a green solid (yield=19%).
m.p.=79° C.

EXAMPLE 303

1-[(2,1,3-Benzothiadiazol-4-yl)sulfonyl]-5-chloro-1H-pyrrolo[3,2-b]pyridine-2-butanoic acid, methyl ester By working in a manner similar to that of Example 3, starting with the ester according to Preparation XLVII, the expected compound is obtained in the form of a brown solid (yield=70%).
m.p.=112° C.

EXAMPLE 304

1-[(5-Benzopyrazinyl)sulfonyl]-5-chloro-1H-pyrrolo[3,2-b]pyridine-2-butanoic acid, methyl ester A solution of 253 mg (0.56 mM) of the compound obtained according to Example 303 in 17 ml of acetic acid is prepared and 364 mg (5.6 mM) of zinc powder are added, with stirring and at room temperature. The reaction mixture is stirred under gentle reflux for 7 hours and then cooled and filtered through a Whatman filter. The filtrate is concentrated under reduced pressure. The yellow solid obtained (methyl ester of 5-chloro-1-[(2,3-diaminophenyl)sulfonyl]-1H-pyrrolo[3,2-b]pyridine-2-butanoic acid) is taken up in 25 ml of methanol, and 242 mg (1.7 mM) of glyoxal, 0.025 ml of acetic acid and 46 mg (0.56 mM) of sodium acetate are added. The reaction mixture is refluxed for 3 hours 30 minutes and then cooled and diluted with ethyl acetate. The organic phase is washed with water and then with, dried over magnesium sulfate and concentrated under reduced pressure. The crude product obtained is purified by chromatography on silica gel, eluting with a cyclohexane/ethyl acetate mixture (50/50; v/v). The expected compound is thus obtained in the form of a yellow solid (yield=73%).
m.p.=71° C.

EXAMPLE 305

1-[(5-Benzopyrazinyl)sulfonyl]-5-chloro-1H-pyrrolo[3,2-b]pyridine-2-butanoic acid By working in a manner similar to that of Example 2, starting with the ester obtained according to Example 304, the expected compound is obtained in the form of a yellow solid (yield=88%).
m.p.=74° C.

EXAMPLE 306

1-[(4-Bromo-2-chlorophenyl)sulfonyl]-5-chloro-1H-pyrrolo[3,2-b]pyridine-2-butanoic acid, methyl ester By working in a manner similar to that of Example 277, starting with 4-bromo-2-chlorobenzenesulfonamide chloride, the expected compound is obtained in the form of a pale yellow solid (yield=87%).

$^1$H NMR (300 MHz, CDCl$_3$) δ: 8.17 (d, 1H); 7.85 (d, 1H); 7.66 (d, 1H); 7.60 (dd, 1H); 7, 18 (d, 1H); 6.59 (s, 1H); 3.67 (s, 3H); 2.89 (t, 2H); 2.39 (t, 2H); 2.02 (quint., 2H).

EXAMPLE 307

1-[[2-Chloro-4-(dimethylamino)phenyl]sulfonyl]-5-chloro-1H-pyrrolo-[3,2-b]pyridine-2-butanoic acid, methyl ester By working in a manner similar to that of Example 275, starting with the compound obtained according to Example 306, the expected compound is obtained in the form of a white solid (yield=36%).
m.p.=123-124° C.

EXAMPLE 308

1-[[2-Chloro-4-(dimethylamino)phenyl]sulfonyl]-5-chloro-1H-pyrrolo-[3,2-b]pyridine-2-butanoic acid By working in a manner similar to that of Example 2, starting with the ester obtained according to Example 307, the expected compound is obtained in the form of a white solid (yield=67%).
m.p.=208° C.

EXAMPLE 309

1-[(2-Chloro-4-methylphenyl)sulfonyl]-5-chloro-1H-pyrrolo[3,2-b]pyridine-2-butanoic acid, methyl ester By working in a manner similar to that of Example 277, starting with 2-chloro-4-methylbenzenesulfonamide chloride, the expected compound is obtained in the form of a white solid (yield=74%).
m.p.=88-89° C.

EXAMPLE 310

1-[(2-Chloro-4-methylphenyl)sulfonyl]-5-chloro-1H-pyrrolo[3,2-b]pyridine-2-butanoic acid By working in a manner similar to that of Example 2, starting with the ester obtained according to Example 309, the expected compound is obtained in the form of a white solid (yield=82%).
m.p.=168-169° C.

The compounds according to the invention described above are listed in the following table:

TABLE I

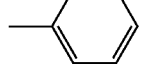

| Ex. | $R_1$ | $X^{(*)}$ | $R_3$ | $R_4$ | n | Ar | R |
|---|---|---|---|---|---|---|---|
| 1 | 5-Cl | 1s | H | H | 1 | 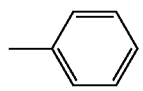 | $CH_3$ |
| 2 | 5-Cl | 1s | H | H | 1 | 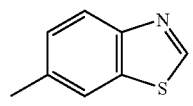 | H |
| 3 | 5-Cl | 1s | H | H | 2 | 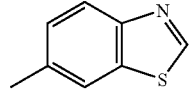 | $CH_3$ |
| 4 | 5-Cl | 1s | H | H | 2 | 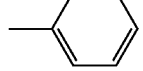 | H |
| 5 | 5-Cl | O | $CH_3$ | H | 1 | 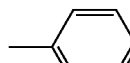 | $C_2H_5$ |
| 6 | 5-Cl | O | $CH_3$ | H | 1 | 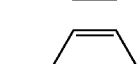 | H |
| 7 | 5-Cl | O | $CH_3$ | $CH_3$ | 1 | 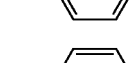 | $CH_3$ |
| 8 | 5-Cl | O | $CH_3$ | $CH_3$ | 1 | 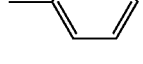 | H |
| 9 | 5-Cl | 1s | H | H | 2 |  | $CH_3$ |

TABLE I-continued
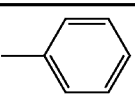
| Ex. | R₁ | X⁽*⁾ | R₃ | R₄ | n | Ar | R |
|---|---|---|---|---|---|---|---|
| 10 | 5-Cl | 1s | H | H | 2 | 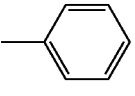 | H |
| 11 | 5-Cl | 1s | CH₃ | CH₃ | 1 | 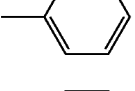 | CH₃ |
| 12 | 5-Cl | 1s | CH₃ | CH₃ | 1 | 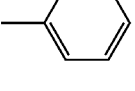 | H |
| 13 | 5-CF₃ | O | CH₃ | H | 1 | 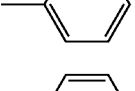 | C₂H₅ |
| 14 | 5-CF₃ | O | CH₃ | H | 1 | 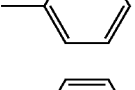 | H |
| 15 | 5-CF₃ | O | CH₃ | CH₃ | 1 | 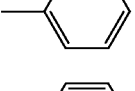 | CH₃ |
| 16 | 5-CF₃ | O | CH₃ | CH₃ | 1 | 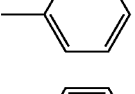 | H |
| 17 | 5-CF₃ | 1s | H | H | 1 | 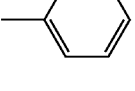 | CH₃ |
| 18 | 5-CF₃ | 1s | H | H | 1 | 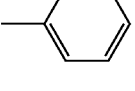 | H |
| 19 | 5-CF₃ | 1s | H | H | 2 | 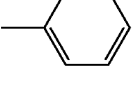 | CH₃ |
| 20 | 5-CF₃ | 1s | H | H | 2 | 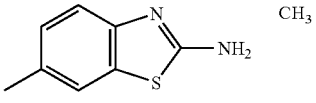 | H |
| 21 | 5-Cl | 1s | H | H | 2 | 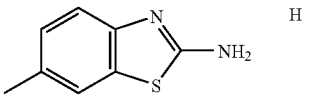 | CH₃ |
| 22 | 5-Cl | 1s | H | H | 2 |  | H |

TABLE I-continued
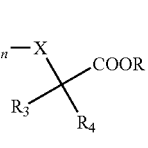
| Ex. | R₁ | X$^{(*)}$ | R₃ | R₄ | n | Ar | R |
|---|---|---|---|---|---|---|---|
| 23 | 5-Cl | 1s | H | H | 2 | 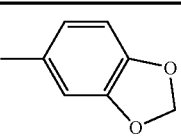 | CH₃ |
| 24 | 5-Cl | 1s | H | H | 2 | 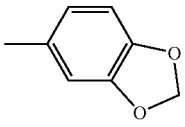 | H |
| 25 | 5-Cl | 1s | H | H | 2 | 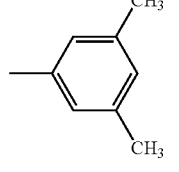 | CH₃ |
| 26 | 5-Cl | 1s | H | H | 2 | 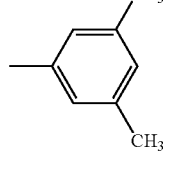 | H |
| 27 | 5-Cl | 1s | H | H | 2 | 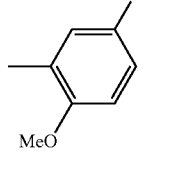 | CH₃ |
| 28 | 5-Cl | 1s | H | H | 2 | 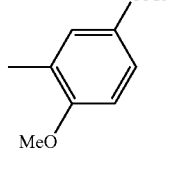 | H |
| 29 | 5-Cl | 1s | H | H | 2 | 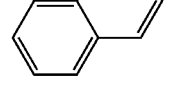 | CH₃ |
| 30 | 5-Cl | 1s | H | H | 2 | 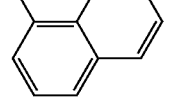 | H |

TABLE I-continued

| Ex. | R₁ | X⁽*⁾ | R₃ | R₄ | n | Ar | R |
|-----|-----|------|-----|-----|---|-----|---|
| 31 | 5-Cl | 1s | H | H | 2 | 6-methyl-4-methyl-3,4-dihydro-2H-benzo[1,4]oxazine | CH₃ |
| 32 | 5-Cl | 1s | H | H | 2 | 6-methyl-4-methyl-3,4-dihydro-2H-benzo[1,4]oxazine | H |
| 33 | 5-Cl | 1s | H | H | 1 | 5-methyl-benzo[1,3]dioxole | CH₃ |
| 34 | 5-Cl | 1s | H | H | 1 | 5-methyl-benzo[1,3]dioxole | H |
| 35 | 5-Cl | 1s | H | H | 1 | 6-methyl-benzothiazole | CH₃ |
| 36 | 5-Cl | 1s | H | H | 1 | 6-methyl-benzothiazole | H |
| 37 | 5-Cl | 1s | H | H | 1 | methylphenyl | Na |
| 38 | 5-Cl | O | CH₃ | H | 1 | 5-methyl-benzo[1,2,5]thiadiazole | C₂H₅ |
| 39 | 5-Cl | O | CH₃ | H | 1 | 5-methyl-benzo[1,2,5]thiadiazole | H |
| 40 | 5-Cl | O | CH₃ | H | 1 | 2,7-dimethyl-benzothiazole | C₂H₅ |

TABLE I-continued

| Ex. | R₁ | X(*) | R₃ | R₄ | n | Ar | R |
|---|---|---|---|---|---|---|---|
| 41 | 5-Cl | O | CH₃ | H | 1 | 7-methyl-2-methyl-benzothiazole | H |
| 42 | 5-Cl | O | CH₃ | CH₃ | 1 | 3-methyl-methoxyphenyl | CH₃ |
| 43 | 5-Cl | O | CH₃ | CH₃ | 1 | 3-methyl-methoxyphenyl | H |
| 44 | 5-Cl | O | CH₃ | H | 1 | 6-methyl-2-NHAc-benzothiazole | C₂H₅ |
| 45 | 5-Cl | O | CH₃ | H | 1 | 6-methyl-2-NHAc-benzothiazole | H |
| 46 | 5-Cl | O | CH₃ | H | 1 | 6-methyl-2-NH₂-benzothiazole | C₂H₅ |
| 47 | 5-Cl | O | CH₃ | H | 1 | 6-methyl-2-NH₂-benzothiazole | H |
| 48 | 5-CF₃ | O | CH₃ | CH₃ | 1 | 6-methyl-benzothiazole | CH₃ |
| 49 | 5-CF₃ | O | CH₃ | CH₃ | 1 | 6-methyl-benzothiazole | H |
| 50 | 5-Cl | O | CH₃ | H | 1 | 6-methyl-benzothiazole | C₂H₅ |
| 51 | 5-Cl | O | CH₃ | H | 1 | 6-methyl-benzothiazole | H |
| 52 | 5-CF₃ | O | CH₃ | H | 1 | 6-methyl-benzothiazole | C₂H₅ |

TABLE I-continued
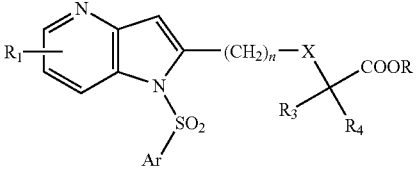
| Ex. | R₁ | X(*) | R₃ | R₄ | n | Ar | R |
|---|---|---|---|---|---|---|---|
| 53 | 5-CF₃ | O | CH₃ | H | 1 |  | H |
| 54 | 5-Cl | 1s | H | H | 1 | 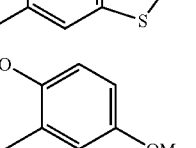 | CH₃ |
| 55 | 5-Cl | Is | H | H | 1 |  | H |
| 56 | 5-Cl | 1s | H | H | 1 | 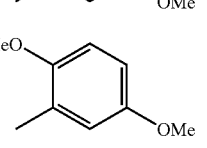 | CH₃ |
| 57 | 5-Cl | 1s | H | H | 1 |  | H |
| 58 | 5-Cl | 1s | H | H | 1 | 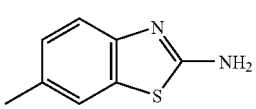 | CH₃ |
| 59 | 5-Cl | 1s | H | H | 1 |  | H |
| 60 | 5-Cl | 1s | H | H | 1 | 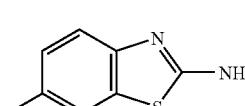 | CH₃ |
| 61 | 5-Cl | 1s | H | H | 1 |  | H |
| 62 | 5-Cl | 1s | H | H | 1 | 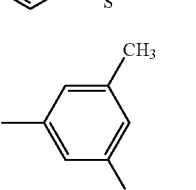 | CH₃ |

TABLE I-continued
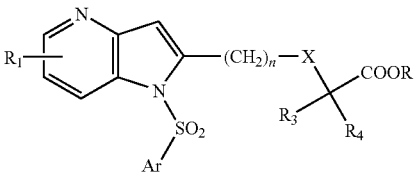
| Ex. | R₁ | X⁽*⁾ | R₃ | R₄ | n | Ar | R |
|---|---|---|---|---|---|---|---|
| 63 | 5-Cl | 1s | H | H | 1 | 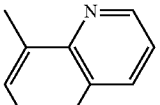 | H |
| 64 | 5-Cl | 1s | H | H | 1 | 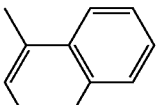 | CH₃ |
| 65 | 5-Cl | 1s | H | H | 1 | 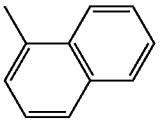 | H |
| 66 | 5-Cl | 1s | H | H | 1 | 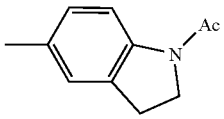 | CH₃ |
| 67 | 5-Cl | 1s | H | H | 1 | 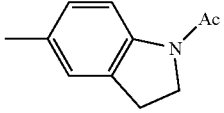 | H |
| 68 | 5-Cl | 1s | H | H | 1 | 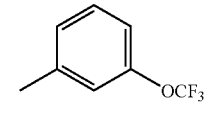 | CH₃ |
| 69 | 5-Cl | 1s | H | H | 1 | 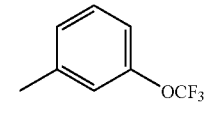 | H |
| 70 | 5-CF₃ | 1s | H | H | 1 | 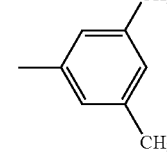 | CH₃ |
| 71 | 5-CF₃ | 1s | H | H | 1 | 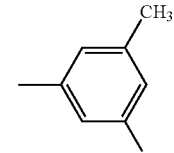 | H |

TABLE I-continued
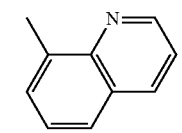
| Ex. | R₁ | X$^{(*)}$ | R₃ | R₄ | n | Ar | R |
|---|---|---|---|---|---|---|---|
| 72 | 5-CF₃ | 1s | H | H | 1 | 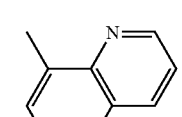 | CH₃ |
| 73 | 5-CF₃ | 1s | H | H | 1 | 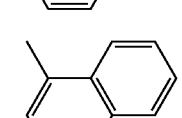 | H |
| 74 | 5-CF₃ | 1s | H | H | 1 | 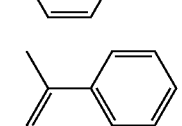 | CH₃ |
| 75 | 5-CF₃ | 1s | H | H | 1 | 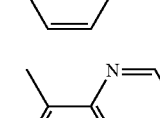 | H |
| 76 | 5-Cl | 1s | H | H | 2 | 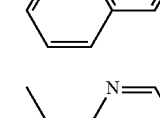 | CH₃ |
| 77 | 5-Cl | 1s | H | H | 2 | 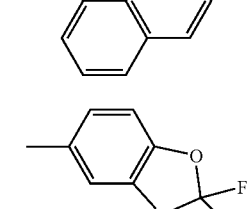 | H |
| 78 | 5-Cl | 1s | H | H | 2 | 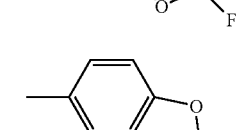 | CH₃ |
| 79 | 5-Cl | 1s | H | H | 2 | 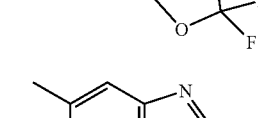 | H |
| 80 | 5-Cl | 1s | H | H | 2 | 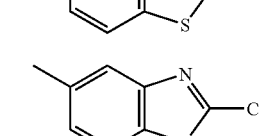 | CH₃ |
| 81 | 5-Cl | 1s | H | H | 2 |  | H |

TABLE I-continued
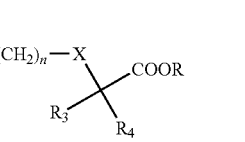
| Ex. | R₁ | X(*) | R₃ | R₄ | n | Ar | R |
|---|---|---|---|---|---|---|---|
| 82 | 5-Cl | 1s | H | H | 2 |  | CH₃ |
| 83 | 5-Cl | 1s | H | H | 2 | 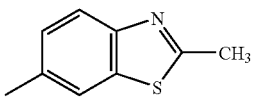 | H |
| 84 | 5-Cl | 1s | H | H | 2 |  | CH₃ |
| 85 | 5-Cl | 1s | H | H | 2 | 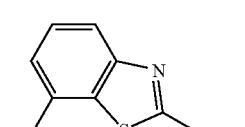 | H |
| 86 | 5-Cl | 1s | H | H | 2 |  | CH₃ |
| 87 | 5-Cl | 1s | H | H | 2 | 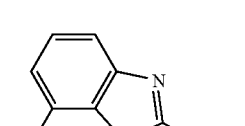 | H |
| 88 | 5-Cl | 1s | H | H | 2 |  | CH₃ |
| 89 | 5-Cl | 1s | H | H | 2 | 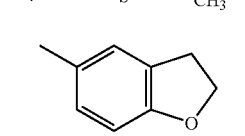 | H |
| 90 | 5-Cl | 1s | H | H | 2 |  | CH₃ |
| 91 | 5-Cl | 1s | H | H | 2 | 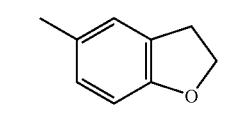 | H |

TABLE I-continued
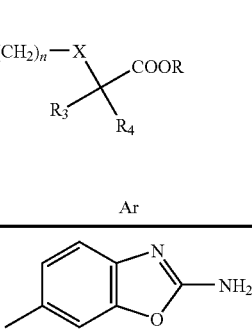
| Ex. | R₁ | X(*) | R₃ | R₄ | n | Ar | R |
|---|---|---|---|---|---|---|---|
| 92 | 5-Cl | 1s | H | H | 2 |  | CH₃ |
| 93 | 5-Cl | 1s | H | H | 2 | 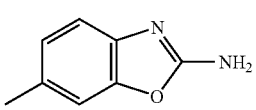 | H |
| 94 | 5-Cl | 1s | H | H | 2 | 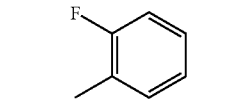 | CH₃ |
| 95 | 5-Cl | 1s | H | H | 2 |  | H |
| 96 | 5-Cl | 1s | H | H | 2 | 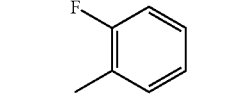 | CH₃ |
| 97 | 5-Cl | 1s | H | H | 2 | 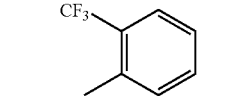 | H |
| 98 | 5-Cl | 1s | H | H | 2 |  | CH₃ |
| 99 | 5-Cl | 1s | H | H | 2 | 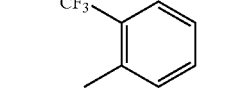 | H |
| 100 | 5-Cl | 1s | H | H | 2 | 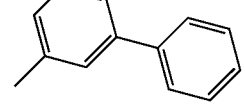 | CH₃ |
| 101 | 5-Cl | 1s | H | H | 2 |  | H |
| 102 | 5-Cl | 1s | H | H | 2 | 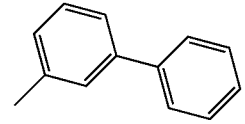 | CH₃ |
| 103 | 5-Cl | 1s | H | H | 2 | 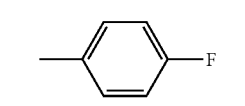 | H |

TABLE I-continued
| Ex. | R₁ | X⁽*⁾ | R₃ | R₄ | n | Ar | R |
|-----|------|------|----|----|---|----|---|
| 104 | 5-Cl | 1s | H | H | 2 | 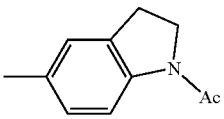 | CH₃ |
| 105 | 5-Cl | 1s | H | H | 2 | 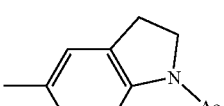 | H |
| 106 | 5-Cl | 1s | H | H | 2 | 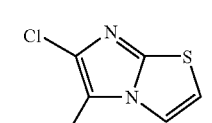 | CH₃ |
| 107 | 5-Cl | 1s | H | H | 2 | 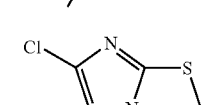 | H |
| 108 | 5-Cl | 1s | H | H | 2 | 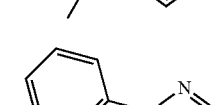 | CH₃ |
| 109 | 5-Cl | 1s | H | H | 2 |  | H |
| 110 | 5-Cl | 1s | H | H | 2 | 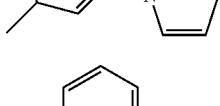 | CH₃ |
| 111 | 5-Cl | 1s | H | H | 2 | 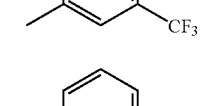 | H |
| 112 | 5-Cl | 1s | H | H | 2 | 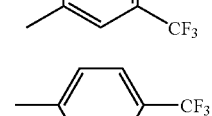 | CH₃ |
| 113 | 5-Cl | 1s | H | H | 2 | 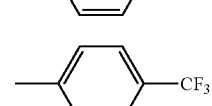 | H |
| 114 | 5-Cl | 1s | H | H | 2 | 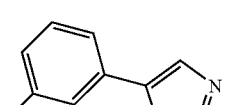 | CH₃ |

TABLE I-continued
| Ex. | R₁ | X⁽*⁾ | R₃ | R₄ | n | Ar | R |
|---|---|---|---|---|---|---|---|
| 115 | 5-Cl | 1s | H | H | 2 | 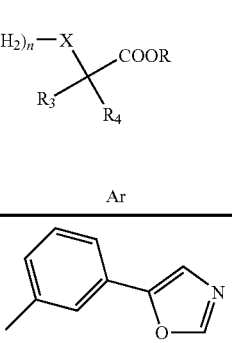 | H |
| 116 | 5-Cl | 1s | H | H | 2 | 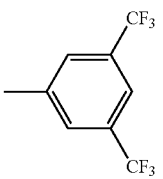 | CH₃ |
| 117 | 5-Cl | 1s | H | H | 2 | 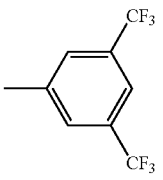 | H |
| 118 | 5-Cl | 1s | H | H | 2 | 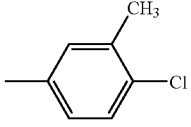 | CH₃ |
| 119 | 5-Cl | 1s | H | H | 2 | 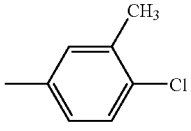 | H |
| 120 | 5-Cl | 1s | H | H | 2 | 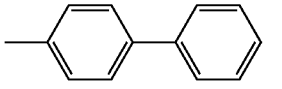 | CH₃ |
| 121 | 5-Cl | 1s | H | H | 2 | 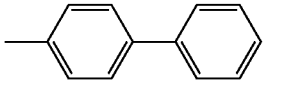 | H |
| 122 | 5-Cl | 1s | H | H | 2 | 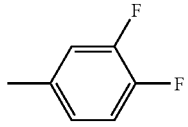 | CH₃ |
| 123 | 5-Cl | 1s | H | H | 2 | 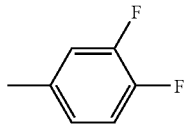 | H |
| 124 | 5-Cl | 1s | H | H | 2 | 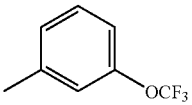 | CH₃ |

TABLE I-continued

| Ex. | R₁ | X⁽*⁾ | R₃ | R₄ | n | Ar | R |
|---|---|---|---|---|---|---|---|
| 125 | 5-Cl | 1s | H | H | 2 | 3-OCF₃-phenyl | H |
| 126 | 5-Cl | 1s | H | H | 2 | benzothiadiazolyl | CH₃ |
| 127 | 5-Cl | 1s | H | H | 2 | benzothiadiazolyl | H |
| 128 | 5-Cl | 1s | H | H | 2 | 4-OCF₃-phenyl | CH₃ |
| 129 | 5-Cl | 1s | H | H | 2 | 4-OCF₃-phenyl | H |
| 130 | 5-Cl | 1s | H | H | 2 | 3-Cl-phenyl | CH₃ |
| 131 | 5-Cl | 1s | H | H | 2 | 3-Cl-phenyl | H |
| 132 | 5-Cl | 1s | H | H | 2 | 4-Cl-phenyl | CH₃ |
| 133 | 5-Cl | 1s | H | H | 2 | 4-Cl-phenyl | H |
| 134 | 5-Cl | 1s | H | H | 2 | 3-OMe-phenyl | CH₃ |
| 135 | 5-Cl | 1s | H | H | 2 | 3-OMe-phenyl | H |
| 136 | 5-Cl | 1s | H | H | 2 | 4-OMe-phenyl | CH₃ |

TABLE I-continued
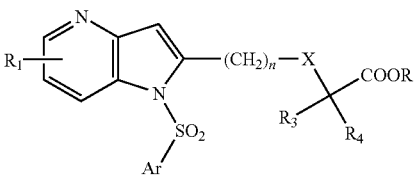
| Ex. | R₁ | X⁽*⁾ | R₃ | R₄ | n | Ar | R |
|---|---|---|---|---|---|---|---|
| 137 | 5-Cl | 1s | H | H | 2 | 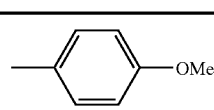 4-OMe-C₆H₄ | H |
| 138 | 5-Cl | 1s | H | H | 2 | 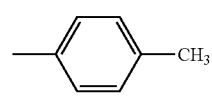 4-CH₃-C₆H₄ | CH₃ |
| 139 | 5-Cl | 1s | H | H | 2 | 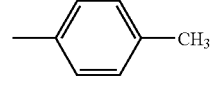 4-CH₃-C₆H₄ | H |
| 140 | 5-Cl | 1s | H | H | 2 | 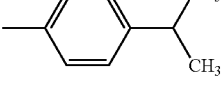 4-iPr-C₆H₄ | CH₃ |
| 141 | 5-Cl | 1s | H | H | 2 | 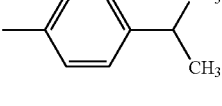 4-iPr-C₆H₄ | H |
| 142 | 5-Cl | 1s | H | H | 2 | 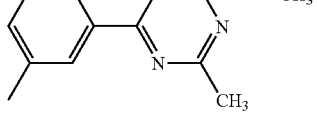 | CH₃ |
| 143 | 5-Cl | 1s | H | H | 2 | 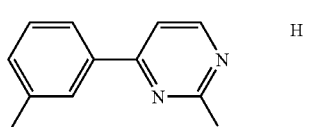 | H |
| 144 | 5-Cl | 1s | H | H | 2 | 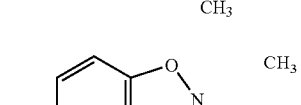 | CH₃ |
| 145 | 5-Cl | 1s | H | H | 2 | 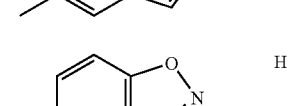 | H |
| 146 | 5-Cl | 1s | H | H | 2 | 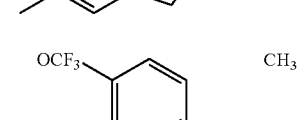 2-OCF₃-C₆H₄ | CH₃ |
| 147 | 5-Cl | 1s | H | H | 2 | 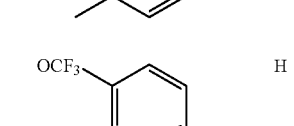 2-OCF₃-C₆H₄ | H |

TABLE I-continued
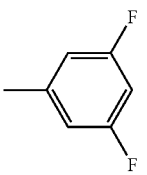
| Ex. | R₁ | X(*) | R₃ | R₄ | n | Ar | R |
|---|---|---|---|---|---|---|---|
| 148 | 5-Cl | 1s | H | H | 2 |  3,5-F₂-C₆H₃ | CH₃ |
| 149 | 5-Cl | 1s | H | H | 2 | 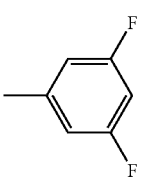 3,5-F₂-C₆H₃ | H |
| 150 | 5-Cl | 1s | H | H | 2 | 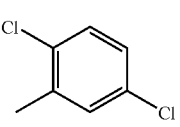 2,5-Cl₂-C₆H₃ | CH₃ |
| 151 | 5-Cl | 1s | H | H | 2 |  2,5-Cl₂-C₆H₃ | H |
| 152 | 5-Cl | 1s | H | H | 2 | 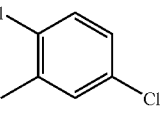 2-Cl-C₆H₄ | CH₃ |
| 153 | 5-Cl | 1s | H | H | 2 | 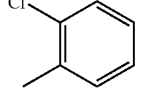 2-Cl-C₆H₄ | H |
| 154 | 5-Cl | 1s | H | H | 2 |  2-CH₃-C₆H₄ | CH₃ |
| 155 | 5-Cl | 1s | H | H | 2 | 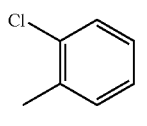 2-CH₃-C₆H₄ | H |
| 156 | 5-Cl | 1s | H | H | 2 | 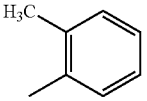 3,5-(CH₃)₂-C₆H₃ | CH₃ |
| 157 | 5-Cl | 1s | H | H | 2 |  3,5-(CH₃)₂-C₆H₃ | H |

TABLE I-continued
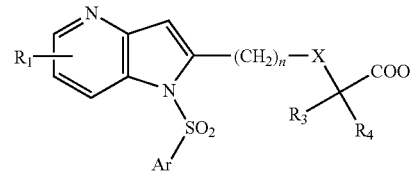
| Ex. | R₁ | X$^{(*)}$ | R₃ | R₄ | n | Ar | R |
|---|---|---|---|---|---|---|---|
| 158 | 5-Cl | 1s | H | H | 2 | 2,6-difluoro-phenyl | CH₃ |
| 159 | 5-Cl | 1s | H | H | 2 | 2,6-difluoro-phenyl | H |
| 160 | 5-Cl | 1s | H | H | 2 | 2,4,6-trifluoro-phenyl | CH₃ |
| 161 | 5-Cl | 1s | H | H | 2 | 2,4,6-trifluoro-phenyl | H |
| 162 | 5-Cl | 1s | H | H | 2 | 2,4-dimethyl-phenyl | CH₃ |
| 163 | 5-Cl | 1s | H | H | 2 | 2,4-dimethyl-phenyl | H |
| 164 | 5-Cl | 1s | H | H | 2 | 3,5-dimethoxy-phenyl | CH₃ |
| 165 | 5-Cl | 1s | H | H | 2 | 3,5-dimethoxy-phenyl | H |

TABLE I-continued

| Ex. | R₁ | X⁽*⁾ | R₃ | R₄ | n | Ar | R |
|---|---|---|---|---|---|---|---|
| 166 | 5-Cl | 1s | H | H | 2 | 4-(isopropoxy)phenyl | CH₃ |
| 167 | 5-Cl | 1s | H | H | 2 | 4-(isopropoxy)phenyl | H |
| 168 | 5-Cl | 1s | H | H | 2 | 2-methoxy-6-methylphenyl | CH₃ |
| 169 | 5-Cl | 1s | H | H | 2 | 2-methoxy-6-methylphenyl | H |
| 170 | 5-Cl | 1s | H | H | 2 | 2-chloro-3,6-dimethylphenyl | CH₃ |
| 171 | 5-Cl | 1s | H | H | 2 | 2-chloro-3,6-dimethylphenyl | H |
| 172 | 5-Cl | 1s | H | H | 2 | 2,4-difluorophenyl | CH₃ |
| 173 | 5-Cl | 1s | H | H | 2 | 2,4-difluorophenyl | H |
| 174 | 5-Cl | 1s | H | H | 2 | 2-chloro-4-methoxyphenyl | CH₃ |
| 175 | 5-Cl | 1s | H | H | 2 | 2-chloro-4-methoxyphenyl | H |
| 176 | 5-Cl | 1s | H | H | 2 | 4-(thiazol-4-yl)phenyl | CH₃ |

TABLE I-continued

| Ex. | R₁ | X(*) | R₃ | R₄ | n | Ar | R |
|---|---|---|---|---|---|---|---|
| 177 | 5-Cl | 1s | H | H | 2 | 4-(thiazol-4-yl)phenyl | H |
| 178 | 5-Cl | 1s | H | H | 2 | 4-tert-butylphenyl | CH₃ |
| 179 | 5-Cl | 1s | H | H | 2 | 4-tert-butylphenyl | H |
| 180 | 5-Cl | 1s | H | H | 2 | 2,3-dihydro-1,4-benzodioxin-6-yl | CH₃ |
| 181 | 5-Cl | 1s | H | H | 2 | 2,3-dihydro-1,4-benzodioxin-6-yl | H |
| 182 | 5-Cl | 1s | H | H | 2 | pyridin-2-yl | CH₃ |
| 183 | 5-Cl | 1s | H | H | 2 | pyridin-2-yl | H |
| 184 | 5-Cl | 1s | H | H | 2 | 3-isopropylphenyl | CH₃ |
| 185 | 5-Cl | 1s | H | H | 2 | 3-isopropylphenyl | H |
| 186 | 5-Cl | 1s | H | H | 2 | 1,4-dimethylnaphth-2-yl | CH₃ |
| 187 | 5-Cl | 1s | H | H | 2 | 1,4-dimethylnaphth-2-yl | H |

TABLE I-continued

| Ex. | $R_1$ | $X^{(*)}$ | $R_3$ | $R_4$ | n | Ar | R |
|---|---|---|---|---|---|---|---|
| 188 | 5-$CF_3$ | 1s | H | H | 2 | 3,5-dimethylphenyl | $CH_3$ |
| 189 | 5-$CF_3$ | 1s | H | H | 2 | 3,5-dimethylphenyl | H |
| 190 | 5-Cl | 1s | H | H | 2 | 2,4-dichlorophenyl | $CH_3$ |
| 191 | 5-Cl | 1s | H | H | 2 | 2,4-dichlorophenyl | H |
| 192 | 5-Cl | 1s | H | H | 2 | 2,3-dichlorophenyl | $CH_3$ |
| 193 | 5-Cl | 1s | H | H | 2 | 2,3-dichlorophenyl | H |
| 194 | 5-Cl | 1s | H | H | 2 | 3-chloro-2-methylphenyl | $CH_3$ |
| 195 | 5-Cl | 1s | H | H | 2 | 3-chloro-2-methylphenyl | H |
| 196 | 5-Cl | 1s | H | H | 2 | 4-methoxy-2-methylphenyl | $CH_3$ |

TABLE I-continued

| Ex. | R₁ | X(*) | R₃ | R₄ | n | Ar | R |
|---|---|---|---|---|---|---|---|
| 197 | 5-Cl | 1s | H | H | 2 | 2-methyl-5-methoxy-4-methylphenyl (H₃C, OMe) | H |
| 198 | 5-CF₃ | 1s | H | H | 2 | 8-methylnaphthalen-1-yl | CH₃ |
| 199 | 5-CF₃ | 1s | H | H | 2 | 8-methylnaphthalen-1-yl | H |
| 200 | 5-CF₃ | 1s | H | H | 2 | 6-methylbenzo[d][1,3]dioxol-5-yl | CH₃ |
| 201 | 5-CF₃ | 1s | H | H | 2 | 6-methylbenzo[d][1,3]dioxol-5-yl | H |
| 202 | 5-CF₃ | 1s | H | H | 2 | 4,7-dimethyl-3,4-dihydro-2H-benzo[b][1,4]oxazin-6-yl | CH₃ |
| 203 | 5-CF₃ | 1s | H | H | 2 | 4,7-dimethyl-3,4-dihydro-2H-benzo[b][1,4]oxazin-6-yl | H |
| 204 | 5-CF₃ | 1s | H | H | 2 | 2,7-dimethylbenzo[d]thiazol-6-yl | CH₃ |
| 205 | 5-CF₃ | 1s | H | H | 2 | 2,7-dimethylbenzo[d]thiazol-6-yl | H |
| 206 | 5-CF₃ | 1s | H | H | 2 | 7-methyl-2,3-dihydrobenzo[b][1,4]dioxin-6-yl | CH₃ |

TABLE I-continued

| Ex. | R₁ | X(*) | R₃ | R₄ | n | Ar | R |
|---|---|---|---|---|---|---|---|
| 207 | 5-CF₃ | 1s | H | H | 2 | 2,3-dihydro-benzo[1,4]dioxin-6-yl | H |
| 208 | 5-Cl | 1s | H | H | 3 | benzothiazol-6-yl | CH₃ |
| 209 | 5-Cl | 1s | H | H | 3 | benzothiazol-6-yl | H |
| 210 | 5-Cl | O | CH₃ | CH₃ | 1 | 4-ethylphenyl | CH₃ |
| 211 | 5-Cl | O | CH₃ | CH₃ | 1 | 4-ethylphenyl | H |
| 212 | 5-Cl | O | CH₃ | CH₃ | 1 | 4-methoxyphenyl | CH₃ |
| 213 | 5-Cl | O | CH₃ | CH₃ | 1 | 4-methoxyphenyl | H |
| 214 | 5-Cl | O | CH₃ | CH₃ | 1 | 2,3-dichlorophenyl | CH₃ |
| 215 | 5-Cl | O | CH₃ | CH₃ | 1 | 2,3-dichlorophenyl | H |
| 216 | 5-Cl | O | CH₃ | CH₃ | 1 | 4-isopropylphenyl | CH₃ |
| 217 | 5-Cl | O | CH₃ | CH₃ | 1 | 4-isopropylphenyl | H |
| 218 | 5-Cl | O | CH₃ | CH₃ | 1 | naphthalen-1-yl | CH₃ |

TABLE I-continued
| Ex. | R₁ | X(*) | R₃ | R₄ | n | Ar | R |
|---|---|---|---|---|---|---|---|
| 219 | 5-Cl | O | CH₃ | CH₃ | 1 | 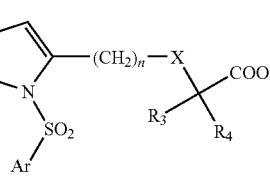 | H |
| 220 | 5-Cl | O | CH₃ | CH₃ | 1 | 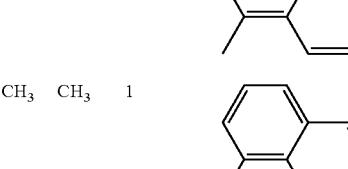 | CH₃ |
| 221 | 5-Cl | O | CH₃ | CH₃ | 1 | 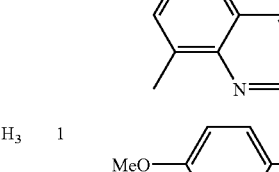 | H |
| 222 | 5-Cl | O | CH₃ | CH₃ | 1 | 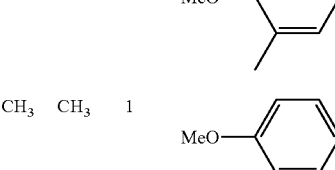 | CH₃ |
| 223 | 5-Cl | O | CH₃ | CH₃ | 1 | 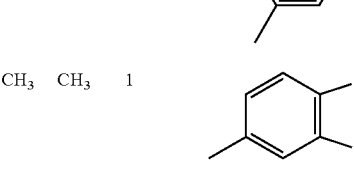 | H |
| 224 | 5-Cl | O | CH₃ | CH₃ | 1 | 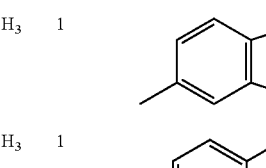 | CH₃ |
| 225 | 5-Cl | O | CH₃ | CH₃ | 1 | 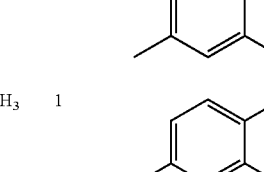 | H |
| 226 | 5-Cl | O | CH₃ | CH₃ | 1 | 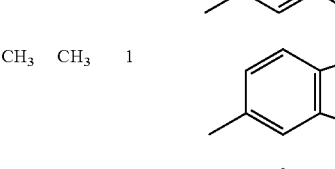 | CH₃ |
| 227 | 5-Cl | O | CH₃ | CH₃ | 1 | 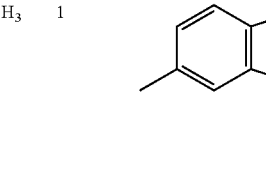 | H |
| 228 | 5-Cl | O | CH₃ | CH₃ | 1 |  | CH₃ |
| 229 | 5-Cl | O | CH₃ | CH₃ | 1 |  | H |

TABLE I-continued

| Ex. | R₁ | X(*) | R₃ | R₄ | n | Ar | R |
|---|---|---|---|---|---|---|---|
| 230 | 5-Cl | O | CH₃ | CH₃ | 1 | 3,5-dimethylphenyl | CH₃ |
| 231 | 5-Cl | O | CH₃ | CH₃ | 1 | 3,5-dimethylphenyl | H |
| 232 | 5-Cl | O | CH₃ | CH₃ | 1 | 4-methyl-3,4-dihydro-2H-benzo[1,4]oxazin-7-yl | CH₃ |
| 233 | 5-Cl | O | CH₃ | CH₃ | 1 | 4-methyl-3,4-dihydro-2H-benzo[1,4]oxazin-7-yl | H |
| 234 | 5-Cl | O | CH₃ (S) | H | 1 | phenyl | C₂H₅ |
| 235 | 5-Cl | O | CH₃ (S) | H | 1 | phenyl | H |
| 236 | 5-Cl | O | CH₃ (R) | H | 1 | phenyl | CH₃ |
| 237 | 5-Cl | O | CH₃ (R) | H | 1 | phenyl | H |
| 238 | 5-CF₃ | O | CH₃ (S) | H | 1 | phenyl | C₂H₅ |
| 239 | 5-CF₃ | O | CH₃ (S) | H | 1 | phenyl | H |
| 240 | 5-CF₃ | O | CH₃ (R) | H | 1 | phenyl | CH₃ |

TABLE I-continued
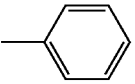
| Ex. | R₁ | X(*) | R₃ | R₄ | n | Ar | R |
|---|---|---|---|---|---|---|---|
| 241 | 5-CF₃ | O | CH₃ (R) | H | 1 | 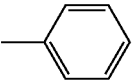 | H |
| 242 | 5-CH₃ | 1s | H | H | 1 | 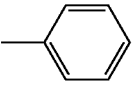 | CH₃ |
| 243 | 5-CH₃ | 1s | H | H | 1 | 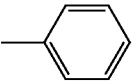 | H |
| 244 | 5-OMe | 1s | H | H | 1 | 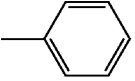 | CH₃ |
| 245 | 5-OMe | 1s | H | H | 1 | 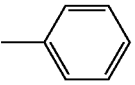 | H |
| 246 | 5-OMe | 1s | H | H | 2 | 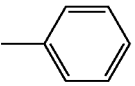 | CH₃ |
| 247 | 5-OMe | 1s | H | H | 2 | 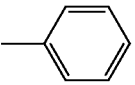 | H |
| 248 | 5-CH₃ | 1s | H | H | 2 | 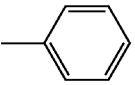 | CH₃ |
| 249 | 5-CH₃ | 1s | H | H | 2 | 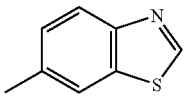 | H |
| 250 | 5-CH₃ | 1s | H | H | 2 | 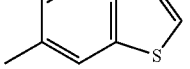 | CH₃ |
| 251 | 5-CH₃ | 1s | H | H | 2 | 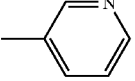 | H |
| 252 | 5-Cl | 1s | H | H | 2 | 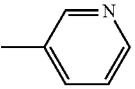 | CH₃ |
| 253 | 5-Cl | 1s | H | H | 2 | 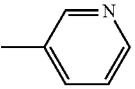 | H |

TABLE I-continued
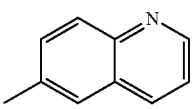
| Ex. | R₁ | X⁽*⁾ | R₃ | R₄ | n | Ar | R |
|---|---|---|---|---|---|---|---|
| 254 | 5-Cl | 1s | H | H | 2 | 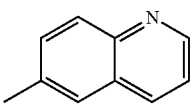 | CH₃ |
| 255 | 5-Cl | 1s | H | H | 2 | 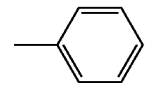 | H |
| 256 | 5-Cl | 1s | H | H | 3 | 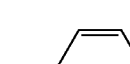 | CH₃ |
| 257 | 5-Cl | 1s | H | H | 3 | 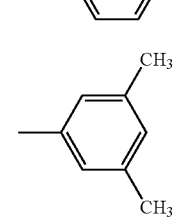 | H |
| 258 | 5-Cl | 1s | H | H | 3 | 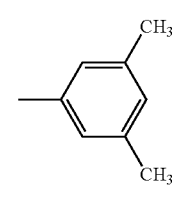 | CH₃ |
| 259 | 5-Cl | 1s | H | H | 3 | 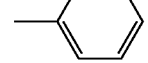 | H |
| 260 | 5-Cl | 1s | CH₃ | CH₃ | 2 | 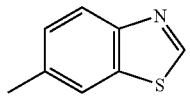 | H |
| 261 | 5-Cl | 1s | CH₃ | CH₃ | 2 | 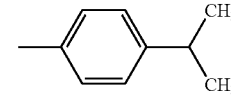 | H |
| 262 | 5-CF₃ | 1s | H | H | 2 | 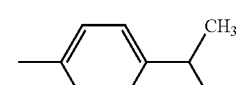 | CH₃ |
| 263 | 5-CF₃ | 1s | H | H | 2 | 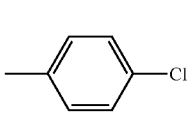 | H |
| 264 | 5-CF₃ | 1s | H | H | 2 |  | CH₃ |

TABLE I-continued

| Ex. | R₁ | X(*) | R₃ | R₄ | n | Ar | R |
|-----|------|------|-----|-----|---|-----|------|
| 265 | 5-CF₃ | 1s | H | H | 2 | 4-Cl-C₆H₄ | H |
| 266 | 5-CF₃ | 1s | H | H | 2 | 2-Cl-C₆H₄ | CH₃ |
| 267 | 5-CF₃ | 1s | H | H | 2 | 2-Cl-C₆H₄ | H |
| 268 | 5-CF₃ | 1s | H | H | 2 | 3-OCF₃-C₆H₄ | CH₃ |
| 269 | 5-CF₃ | 1s | H | H | 2 | 3-OCF₃-C₆H₄ | H |
| 270 | 5-Cl | 1s | H | H | 2 | 4-Br-C₆H₄ | CH₃ |
| 271 | 5-Cl | 1s | H | H | 2 | 4-morpholino-C₆H₄ | CH₃ |
| 272 | 5-Cl | 1s | H | H | 2 | 4-morpholino-C₆H₄ | H |
| 273 | 5-Cl | 1s | H | H | 2 | 4-pyrrolidino-C₆H₄ | CH₃ |
| 274 | 5-Cl | 1s | H | H | 2 | 4-pyrrolidino-C₆H₄ | H |
| 275 | 5-Cl | 1s | H | H | 2 | 4-N(CH₃)₂-C₆H₄ | CH₃ |
| 276 | 5-Cl | 1s | H | H | 2 | 4-N(CH₃)₂-C₆H₄ | H |

TABLE I-continued

| Ex. | R₁ | X(*) | R₃ | R₄ | n | Ar | R |
|---|---|---|---|---|---|---|---|
| 277 | 5-Cl | 1s | H | H | 2 | 3-bromophenyl | CH₃ |
| 278 | 5-Cl | 1s | H | H | 2 | 3-(N,N-dimethylamino)phenyl | CH₃ |
| 279 | 5-Cl | 1s | H | H | 2 | 4-iodophenyl | CH₃ |
| 280 | 5-Cl | 1s | H | H | 2 | 4-(thiazol-2-yl)phenyl | CH₃ |
| 281 | 5-Cl | 1s | H | H | 2 | 4-(thiazol-2-yl)phenyl | H |
| 282 | 5-Cl | 1s | H | H | 2 | 3-(thiazol-2-yl)phenyl | CH₃ |
| 283 | 5-Cl | 1s | H | H | 2 | 3-(thiazol-2-yl)phenyl | H |
| 284 | 5-Cl | 1s | H | H | 2 | 3-(thiazol-5-yl)phenyl | CH₃ |
| 285 | 5-Cl | 1s | H | H | 2 | 3-(thiazol-5-yl)phenyl | H |
| 286 | 5-Cl | 1s | H | H | 2 | 3-(thiazol-4-yl)phenyl | CH₃ |
| 287 | 5-Cl | 1s | H | H | 2 | 3-(thiazol-4-yl)phenyl | H |

TABLE I-continued
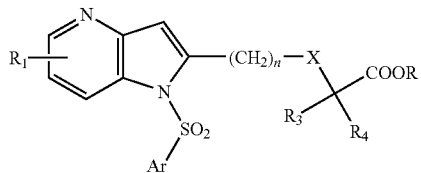
| Ex. | R₁ | X(*) | R₃ | R₄ | n | Ar | R |
|---|---|---|---|---|---|---|---|
| 288 | 5-Cl | 1s | H | H | 2 | -C₆H₄-2-pyridyl | CH₃ |
| 289 | 5-Cl | 1s | H | H | 2 | -C₆H₄-2-pyridyl | H |
| 290 | 5-Cl | 1s | H | H | 2 | -C₆H₄-3-pyridyl | CH₃ |
| 291 | 5-Cl | 1s | H | H | 2 | -C₆H₄-3-pyridyl | H |
| 292 | 5-Cl | 1s | H | H | 2 | -C₆H₄-4-pyridyl | CH₃ |
| 293 | 5-Cl | 1s | H | H | 2 | -C₆H₄-4-pyridyl | H |
| 294 | 5-Cl | 1s | H | H | 2 | 4-F-3-NO₂-C₆H₃- | CH₃ |
| 295 | 5-Cl | 1s | H | H | 2 | benzothiazol-6-yl | CH₃ |
| 296 | 5-Cl | 1s | H | H | 2 | benzothiazol-6-yl | H |
| 297 | 5-Cl | 1s | H | H | 2 | 4-NH₂-3-NO₂-C₆H₃- | CH₃ |
| 298 | 5-Cl | 1s | H | H | 2 | 3,4-diNH₂-C₆H₃- | CH₃ |
| 299 | 5-Cl | 1s | H | H | 2 | quinoxalin-6-yl | CH₃ |

TABLE I-continued
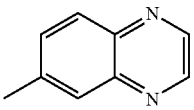
| Ex. | R₁ | X⁽*⁾ | R₃ | R₄ | n | Ar | R |
|---|---|---|---|---|---|---|---|
| 300 | 5-Cl | 1s | H | H | 2 |  | H |
| 301 | 5-Cl | 1s | H | H | 2 | 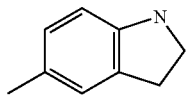 | H |
| 302 | 5-Cl | 1s | H | H | 1 |  | H |
| 303 | 5-Cl | 1s | H | H | 2 | 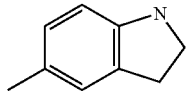 | CH₃ |
| 304 | 5-Cl | 1s | H | H | 2 |  | CH₃ |
| 305 | 5-Cl | 1s | H | H | 2 | 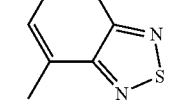 | H |
| 306 | 5-Cl | 1s | H | H | 2 | 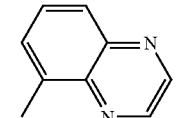 | CH₃ |
| 307 | 5-Cl | 1s | H | H | 2 | 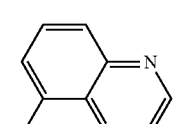 | CH₃ |
| 308 | 5-Cl | 1s | H | H | 2 |  | H |
| 309 | 5-Cl | 1s | H | H | 2 | 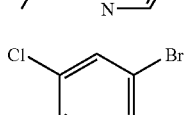 | CH₃ |
| 310 | 5-Cl | 1s | H | H | 2 | 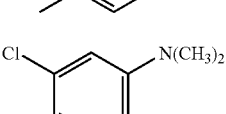 | H |
*"1s" means: single bond, and Ac represents the acetyl group Pharmacological Activity The compounds of the invention were subjected to biological tests so as to evaluate their potential for treating or preventing certain pathologies. In a first stage, the capacity of the compounds to behave as PPAR nuclear receptor activators was measured.

A transactivation test is used as primary screening test. Cos-7 cells are transfected with a plasmid that expresses a construct of a murine or human PPAR-Gal4 receptor (PPARα-Gal4 or PPARδ-Gal4 or PPARγ-Gal4 receptor) and a reporter plasmid 5Gal4pGL3 TK Luc. The transfections are performed using a chemical agent (Jet PEI).

The transfected cells are distributed in 384-well plates and left to stand for 24 hours.

After 24 hours, the culture medium is changed. The test products are added (final concentration of between $10^{-4}$ and $3\times10^{-10}$ M) to the culture medium. After incubating overnight, the luciferase expression is measured after addition of "SteadyGlo" according to the manufacturer's instructions (Promega). Fenofibric acid at $10^{-5}$ M (PPARα agonist), GW501516 at $10^{-8}$ M (PPARδ agonist) and rosiglitazone at $10^{-6}$ M (PPARy agonist) are used as references.

The results are expressed as a level of induction (number of times) compared with the basal level as a percentage of activity of the adequate reference (reference=100%). The effect-concentration curves and the $EC_{50}$ values are calculated using the Assay Explorer software (MDL).

The compounds according to the invention have a level of induction ranging up to 319% (PPARα), 151% (PPARδ) and 114% (PPARγ). The compounds according to the invention have an $EC_{50}$ of between 4 nM and 1500 nM.

A second series of tests was performed with the compounds according to the invention, with the aim of confirming the activity deduced from their affinity for the receptors mentioned previously. This test consists in measuring the β-oxidation on cells of human hepatic origin HuH7 and cells of murine muscle origin C2C12 after differentiation as myotubes.

The cells are inoculated in Petri dishes comprising a central well. The products are added to the culture medium and incubated for 48 hours at different concentrations. After incubation for 22 hours, $^{14}C$-radiolabeled oleate (oleate 1-C14) is added to the culture medium. The β-oxidation reaction is stopped two hours later by adding 40% perchloric acid.

The $CO_2$ released during the oxidation of the oleate is trapped with KOH solution and then counted.

Each test is performed three times.

The results are expressed as a percentage of variation relative to the control dishes (dishes without compounds).

According to this test, the compounds according to the invention increase the β-oxidation by up to +145% at a concentration of 10 μM on HuH7 cells. The β-oxidation is also increased by 70% in the presence, for example, of the compound according to Example 10 used at a concentration of 10 μM during a test on C2C12 cells.

Certain compounds according to the invention were tested on a model of db/db mice in order to confirm their potential as active principle. The test protocol is as follows:

Homozygous male C57BL/Ks-db mice (db/db mice), 11-13 weeks old at the start of the studies, are divided into groups of 9-10 animals. The products are administered orally, once a day for 5 days. A group of mice receives the vehicle alone (methylcellulose solution at 0.5% or 1%). A blood sample is taken from the retro-orbital sinus before treatment and 4 hours after the final gavage.

After centrifugation, the serum is collected and the levels of cholesterol, triglycerides and glucose are measured using a multiparameter analyzer with commercial products.

The results are expressed as a percentage of variation on the final day relative to the control group. By way of example, a number of results obtained with the compounds according to the invention are given in the following table, in comparison with fenofibrate or rosiglitazone:

Pharmacological Activity

| Compound | Assay (mg/kg) | Glucose | Triglycerides | Cholesterol |
|---|---|---|---|---|
| Fenofibrate | 100 | −9 | −7 | +32 |
| Rosiglitazone | 3 | −41 | −52 | −30 |
| Ex. 2 | 10 | −36 | −32 | +41 |
| Ex. 20 | 10 | −72 | −65 | +13 |
| Ex. 4 | 10 | −57 | −45 | +4 |
| Ex. 293 | 10 | −24 | −15 | +16 |
| Ex. 259 | 10 | −51 | −16 | +32 |

These results, which are in accordance with the modifications expected from PPAR nuclear receptor activators, confirm the value of the compounds according to the invention for their use as active principles of medicaments for human use for preventing or treating hypertriglyceridemia, hypercholesterolemia and obesity, and, more generally, for re-establishing normal parameters during a disruption in lipid and carbohydrate metabolism. The compounds according to the invention also find their use in the case of treating endothelial dysfunction, inflammatory diseases or neurodegenerative diseases.

The invention also relates to pharmaceutical compositions for preventing or treating the diseases mentioned above, when they contain, as active principle, at least one of the compounds of formula I according to the invention.

These pharmaceutical compositions may be prepared in a conventional manner, using pharmaceutically acceptable excipients, so as to obtain forms that may preferably be administered orally, for example tablets or gel capsules.

In practice, in the case of oral administration of the compound, the daily dosage in man will preferably be between 5 and 500 mg.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A pyrrolopyridine compound corresponding to formula I:

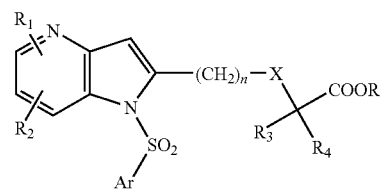

(I)

wherein
R$_1$ and R$_2$ each independently represent hydrogen, halogen, C$_1$-C$_3$ alkyl, C$_1$-C$_4$ alkoxy or CF$_3$;
R$_3$ and R$_4$ each independently represent hydrogen or C$_1$-C$_4$ alkyl;
R represents hydrogen or C$_1$-C$_3$ alkyl;
n represents 1, 2 or 3;
X represents a single bond or an oxygen atom, and
Ar represents an aromatic or heteroaromatic nucleus selected from the group consisting of phenyl, pyrazolyl, imidazolyl, thiazolyl, oxazolyl, isoxazolyl, furyl, thienyl, pyrrolyl, pyridyl, biphenyl, naphthyl, 1,2,3,4-tetrahydronaphthyl, quinolyl, isoquinolyl, 1,2,3,4-tetrahydroquinolyl, benzimidazolyl, benzopyrazinyl, indolyl, 2,3-dihydroindolyl, benzofuryl, 2,3-dihydrobenzofuryl, benzothiazolyl, benzothiadiazolyl, benzisoxazolyl, 3,4-dihydro-1,4-benzoxazinyl, 1,3-benzodioxolyl, 2,3-dihydrobenzodioxinyl, imidazothiazolyl and benzoxazolyl groups, optionally substituted with one or more substituents selected from the group consisting of halogen, $C_1$-$C_6$ alkyl, $C_1$-$C_4$ alkoxy, trifluoromethyl, trifluoromethoxy, nitro, acetyl, acetylamino, dialkylamino, amino, oxazolyl, thiazolyl, pyrazolyl, pyrrolidinyl, pyridyl, pyrimidinyl, methylpyrimidinyl and morpholinyl, or a pharmaceutically acceptable salt thereof.

2. A compound as claimed in claim 1, wherein Ar represents an aromatic or heteroaromatic nucleus selected from the group consisting of phenyl, pyridyl, biphenyl, naphthyl, quinolyl, benzopyrazinyl, indolyl, 2,3-dihydroindolyl, benzofuryl, 2,3-dihydrobenzofuryl, benzothiazolyl, benzothiadiazolyl, benzisoxazolyl, 3,4-dihydro-1,4-benzoxazinyl, 1,3-benzodioxolyl, 2,3-dihydrobenzodioxinyl, imidazothiazolyl and benzoxazolyl groups, optionally substituted with one or more substituents selected from the group consisting of halogen, $C_1$-$C_6$ alkyl, $C_1$-$C_4$ alkoxy, trifluoromethyl, trifluoromethoxy, nitro, acetyl, acetylamino, dialkylamino, amino, oxazolyl, thiazolyl, pyrazolyl, pyrrolidinyl, pyridyl, pyrimidinyl, methylpyrimidinyl or morpholinyl.

3. A compound as claimed in claim 1, wherein $R_1$ represents chlorine or trifluoromethyl.

4. A pharmaceutical composition comprising a compound as claimed in claim 1 and at least one pharmaceutically acceptable carrier or adjuvant.

5. A method of treating a condition selected from the group consisting of hypertriglyceridemia, hyperlipidemia, hypercholesterolemia, dyslipidemia, insulin resistance, type 2 diabetes, obesity, rheumatoid arthritis and Parkinson's disease in a subject in need thereof, said method comprising administering to said subject a pharmacologically effective amount of a compound as claimed in claim 1.

6. A method as claimed in claim 5, wherein said condition is selected from the group consisting of hypertriglyceridemia, hyperlipidemia, hypercholesterolemia, dyslipidemia, insulin resistance, type 2 diabetes and obesity.

7. A process for preparing a compound as claimed in claim 1, said process comprising:

a) halogenating an aminopyridine of formula II:

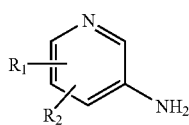

(II)

wherein $R_1$ and $R_2$ each independently represent hydrogen, fluorine, bromine, chlorine, $C_1$-$C_4$ alkyl, $C_1$-$C_4$ alkoxy or trifluoromethyl;

using a halogenating agent in a solvent at room temperature for 5 to 24 hours to obtain a compound of formula III:

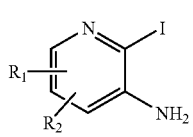

(III)

in which:

$R_1$ and $R_2$ have the meanings given above;

b) reacting the compound of formula III according to the Sonogashira reaction with an acetylenic compound of formula IV:

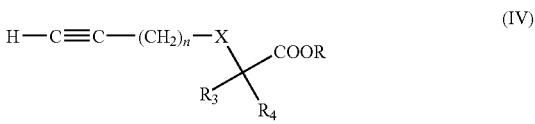

(IV)

in which:

n represents 1, 2 or 3;

$R_3$ and $R_4$ each independently represent hydrogen or $C_1$-$C_4$ alkyl;

R represents $C_1$-$C_3$ alkyl;

X represents a single bond or an oxygen atom;

in the presence of cuprous iodide, a palladium-based catalyst and an organic base in a solvent at a temperature between 0 and 60° C. for 2 to 24 hours to obtain a compound of formula V:

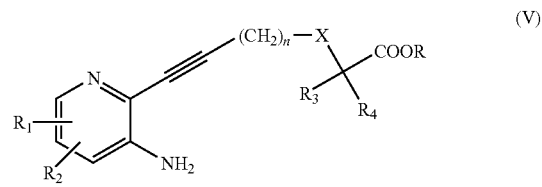

(V)

in which:

$R_1$, $R_2$, n, X, $R_3$, $R_4$ and R have the meanings given above;

c) reacting the compound of formula V with an arylsulfonyl chloride of formula VI:

(VI)

in which:

Ar represents an aromatic or heteroaromatic nucleus selected from the group consisting of phenyl, pyrazolyl, imidazolyl, thiazolyl, oxazolyl, isoxazolyl, furyl, thienyl, pyrrolyl, pyridyl, biphenyl, naphthyl, 1,2,3, 4-tetrahydronaphthyl, quinolyl, isoquinolyl, 1,2,3,4-tetrahydroquinolyl, benzimidazolyl, benzopyrazinyl, indolyl, 2,3-dihydroindolyl, benzofuryl, 2, 3-dihydrobenzofuryl, benzothiazolyl, benzothiadiazolyl, benzisoxazolyl, 3, 4-dihydro-1,4-benzoxazinyl, 1,3-benzodioxolyl, 2,3-dihydrobenzodioxinyl, imidazothiazolyl and benzoxazolyl, optionally substituted with one or more substituents selected from the group consisting of halogen, $C_1$-$C_6$ alkyl, $C_1$-$C_4$ alkoxy, trifluoromethyl, trifluoromethoxy, nitro, acetyl, acetylamino, dialkylamino, amino, oxazolyl, thiazolyl, pyrazolyl, pyrrolidinyl, pyridyl, pyrimidinyl, methylpyrimidinyl and morpholinyl;

in the presence of pyridine, optionally in a solvent, at room temperature for 10 to 120 minutes to obtain a compound of formula VII:

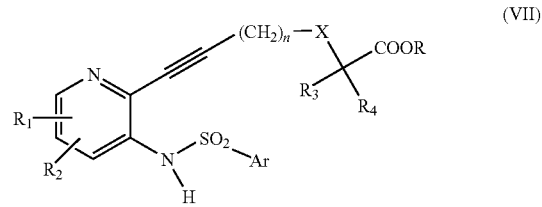

(VII)

in which:

$R_1$, $R_2$, n, X, $R_3$, $R_4$, R and Ar have the meanings given above;

d) cyclizing the compound of formula VII to obtain a compound of formula Ia

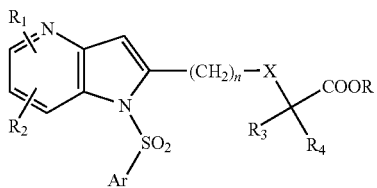
(Ia)

in which:
R₁, R₂, n, X, R₃, R₄, R and Ar have the meanings given above; and e) optionally hydrolyzing an ester function of the compound of formula Ia, and treating with acid to obtain a compound of formula I in the form of a free acid of formula Ib:

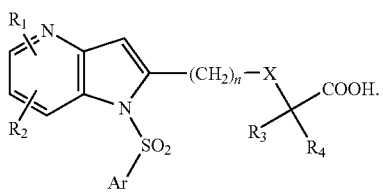
(Ib)

8. A process as claimed in claim 7, wherein the halogenation reaction is an iodination reaction carried out using iodine in the presence of silver sulfate or benzyltrimethylammonium dichloroiodate; the palladium-based catalyst is tetrakis(triphenylphosphine)palladium or dichlorobis(triphenylphosphine)palladium; cyclization is effected via the action of copper II acetate in a solvent at a temperature close to the reflux temperature of the solvent for 4 to 24 hours, and if optional hydrolyzing is carried out, the hydrolyzing reaction is effected with a mineral base.

9. A process for preparing a compound as claimed in claim 1, said process comprising:
a) reacting a compound of formula III:

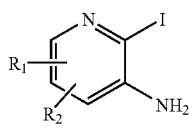
(III)

in which
R₁ and R₂ each independently represent hydrogen, chlorine, fluorine, C₁-C₄ alkyl, C₁-C₄ alkoxy or trifluoromethyl,
with an arylsulfonyl chloride of formula VI:

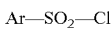
Ar—SO₂—Cl  (VI)

in which:
Ar represents an aromatic or heteroaromatic nucleus selected from the group consisting of phenyl, pyrazolyl, imidazolyl, thiazolyl, oxazolyl, isoxazolyl, furyl, thienyl, pyrrolyl, pyridyl, biphenyl, naphthyl, 1,2,3, 4-tetrahydronaphthyl, quinolyl, isoquinolyl, 1,2,3,4-tetrahydroquinolyl, benzimidazolyl, benzopyrazinyl, indolyl, 2,3-dihydroindolyl, benzofuryl, 2, 3-dihydrobenzofuryl, benzothiazolyl, benzothiadiazolyl, benzisoxazolyl, 3, 4-dihydro-1,4-benzoxazinyl, 1,3-benzodioxolyl, 2,3-dihydrobenzodioxinyl, imidazothiazolyl and benzoxazolyl, optionally substituted with one or more substituents selected from the group consisting of halogen, C₁-C₆ alkyl, C₁-C₄ alkoxy, trifluoromethyl, trifluoromethoxy, nitro, acetyl, acetylamino, dialkylamino, amino, oxazolyl, thiazolyl, pyrazolyl, pyrrolidinyl, pyridyl, pyrimidinyl, methylpyrimidinyl and morpholinyl;
in a solvent at room temperature for 1 to 12 hours to obtain a compound of formula VIII:

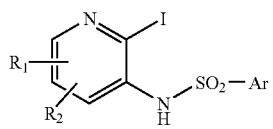
(VIII)

in which:
R₁, R₂ and Ar have the meanings given above;
b) reacting the compound of formula VIII with an acetylenic compound of formula III:

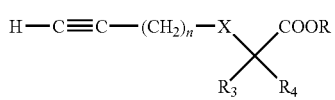
(III)

in which:
n represents 1, 2 or 3;
R₃ and R₄ each independently represent hydrogen or C₁-C₄ alkyl;
R represents C₁-C₃ alkyl;
X represents a single bond or an oxygen atom;
in the presence of cuprous iodide, a palladium-based catalyst and an organic base in a solvent at a temperature between 0 and 60° C. for 2 to 24 hours to obtain a compound of formula Ia:

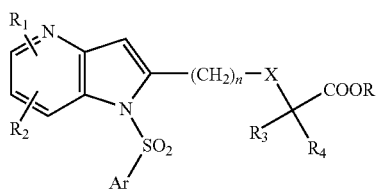
(Ia)

in which
R₁, R₂, n, X, R₃, R₄, R and Ar have the meanings given above; and c) optionally hydrolyzing an ester function of the compound of formula Ia and treating with an acid to obtain a compound of formula I in the form of a free acid:

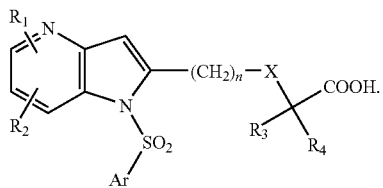

10. A process as claimed in claim 9, wherein if optional hydrolyzing is carried out, the hydrolyzing reaction is effected with a mineral base.

* * * * *